(12) United States Patent
Haraguchi et al.

(10) Patent No.: US 10,389,921 B2
(45) Date of Patent: Aug. 20, 2019

(54) ENDOSCOPE

(71) Applicant: PANASONIC CORPORATION, Osaka (JP)

(72) Inventors: Naoyuki Haraguchi, Saga (JP); Takafumi Sanada, Fukuoka (JP); Nobuhiro Tsuchihashi, Fukuoka (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

(21) Appl. No.: 15/710,364

(22) Filed: Sep. 20, 2017

(65) Prior Publication Data

US 2018/0020134 A1    Jan. 18, 2018

Related U.S. Application Data

(63) Continuation of application No. 15/240,751, filed on Aug. 18, 2016, now Pat. No. 9,838,576.

(30) Foreign Application Priority Data

Aug. 31, 2015    (JP) ................................. 2015-171550
Aug. 31, 2015    (JP) ................................. 2015-171551

(Continued)

(51) Int. Cl.
     *A61B 1/00*        (2006.01)
     *H04N 5/225*      (2006.01)
     (Continued)

(52) U.S. Cl.
     CPC ......... *H04N 5/2252* (2013.01); *A61B 1/0011* (2013.01); *A61B 1/00096* (2013.01);
     (Continued)

(58) Field of Classification Search
     CPC ... A61B 1/0011; A61B 1/00163; A61B 1/055; A61B 1/051; A61B 1/05; A61B 1/00096;
     (Continued)

(56) References Cited

U.S. PATENT DOCUMENTS 4,788,967 A     12/1988   Ueda
5,601,525 A *   2/1997    Okada .................... A61B 1/002
                                                           359/435

(Continued)

FOREIGN PATENT DOCUMENTS

CN          101043842 A     9/2007
CN          104105440 A1    10/2014
                               (Continued)

OTHER PUBLICATIONS

First Action Interview Pilot Program Pre-Interview Communication, dated Dec. 21, 2018, for the corresponding U.S. Appl. No. 15/710,378, 7 pages.

(Continued)

*Primary Examiner* — Timothy J Neal
(74) *Attorney, Agent, or Firm* — Seed IP Law Group LLP

(57) ABSTRACT

An endoscope includes at least one lens having a circular exterior shape in a direction perpendicular to an optical axis, an image sensor that has a square exterior shape in the direction perpendicular to the optical axis, and has one side whose length is same as length of a diameter of the lens, a sensor cover that has a square exterior shape in the direction perpendicular to the optical axis, and has one side whose length is same as one side length of the image sensor, a bonding resin portion that fixes the sensor cover to the lens, the optical axis of the lens coinciding with a center of the imaging area.

8 Claims, 34 Drawing Sheets

(30) Foreign Application Priority Data

| Aug. 31, 2015 | (JP) | 2015-171552 |
|---|---|---|
| Aug. 31, 2015 | (JP) | 2015-171554 |
| Apr. 5, 2016 | (JP) | 2016-076172 |

(51) Int. Cl.

| A61B 1/05 | (2006.01) |
|---|---|
| A61B 1/06 | (2006.01) |
| G02B 23/24 | (2006.01) |
| H04N 5/369 | (2011.01) |
| H04N 5/232 | (2006.01) |

(52) U.S. Cl.
CPC ...... *A61B 1/00114* (2013.01); *A61B 1/00135* (2013.01); *A61B 1/00137* (2013.01); *A61B 1/051* (2013.01); *A61B 1/0607* (2013.01); *G02B 23/243* (2013.01); *G02B 23/2476* (2013.01); *H04N 5/2253* (2013.01); *H04N 5/2254* (2013.01); *H04N 5/2256* (2013.01); *G02B 23/2469* (2013.01); *H04N 5/23293* (2013.01); *H04N 5/369* (2013.01); *H04N 2005/2255* (2013.01)

(58) Field of Classification Search
CPC . G02B 23/2423; G02B 23/2476; G02B 7/025
See application file for complete search history.

(56) References Cited

U.S. PATENT DOCUMENTS

| 5,632,718 | A | * | 5/1997 | Igarashi | A61B 1/002 |
|---|---|---|---|---|---|
| | | | | | 359/434 |
| 5,951,464 | A | | 9/1999 | Takahashi et al. | |
| 5,960,145 | A | | 9/1999 | Sanchez | |
| 6,142,930 | A | * | 11/2000 | Ito | A61B 1/00096 |
| | | | | | 348/76 |
| 6,350,231 | B1 | | 2/2002 | Ailinger et al. | |
| 6,425,418 | B1 | | 7/2002 | Maeda et al. | |
| 6,530,881 | B1 | | 3/2003 | Ailinger et al. | |
| 2002/0013511 | A1 | | 1/2002 | Ailinger et al. | |
| 2004/0257665 | A1 | * | 12/2004 | Lei | G02B 3/00 |
| | | | | | 359/642 |
| 2007/0182842 | A1 | | 8/2007 | Sonnenschein et al. | |
| 2008/0021281 | A1 | | 1/2008 | Fujimori | |
| 2009/0010140 | A1 | | 1/2009 | Ishii et al. | |
| 2009/0173875 | A1 | | 7/2009 | Ichimura et al. | |
| 2010/0085466 | A1 | | 4/2010 | Fujimori et al. | |
| 2011/0034769 | A1 | * | 2/2011 | Adair | H04N 5/3765 |
| | | | | | 600/110 |
| 2012/0265094 | A1 | | 10/2012 | Goldfarb et al. | |
| 2013/0162789 | A1 | | 6/2013 | Chou et al. | |
| 2013/0165752 | A1 | | 6/2013 | Chou | |
| 2013/0172678 | A1 | | 7/2013 | Kennedy, II et al. | |
| 2013/0329026 | A1 | * | 12/2013 | Hida | A61B 1/04 |
| | | | | | 348/65 |
| 2014/0107421 | A1 | | 4/2014 | Nakatate et al. | |
| 2014/0275786 | A1 | | 9/2014 | Goto et al. | |
| 2014/0346322 | A1 | | 11/2014 | Fujimori et al. | |
| 2015/0182205 | A1 | | 7/2015 | Millard et al. | |
| 2015/0238069 | A1 | | 8/2015 | Osada et al. | |
| 2015/0365571 | A1 | | 12/2015 | Wada et al. | |
| 2017/0049304 | A1 | | 2/2017 | Karaki et al. | |
| 2017/0055817 | A1 | | 3/2017 | Dybiec et al. | |

FOREIGN PATENT DOCUMENTS

| CN | 106455911 A | 2/2017 |
|---|---|---|
| DE | 600 10 430 T2 | 9/2004 |
| EP | 1 721 564 A2 | 11/2006 |
| EP | 2 680 059 A1 | 1/2014 |
| JP | 07-184843 A | 7/1995 |
| JP | 7-333408 A | 12/1995 |
| JP | 09-262207 A | 10/1997 |
| JP | 2010-091986 A | 4/2010 |
| JP | 2010-164718 A | 7/2010 |
| JP | 2012-213441 A | 11/2012 |
| JP | 2014-087483 A | 5/2014 |
| JP | 2014-155526 A | 8/2014 |
| JP | 2014-188170 A | 10/2014 |
| JP | 2014-230638 A | 12/2014 |
| JP | 2015-047278 A | 3/2015 |
| JP | 2015-073540 A | 4/2015 |
| JP | 2015-080646 A | 4/2015 |
| JP | 2015-127741 A | 7/2015 |
| WO | 2008/035470 A1 | 3/2008 |
| WO | 2011/105201 A1 | 9/2011 |
| WO | 2013/031276 A1 | 3/2013 |
| WO | 2013/146091 A1 | 10/2013 |
| WO | 201/126144 A1 | 8/2014 |
| WO | 2014192510 A1 | 12/2014 |

OTHER PUBLICATIONS

First Action Interview Pilot Program Pre-Interview Communication, dated Dec. 21, 2018, for the corresponding U.S. Appl. No. 15/710,349, 7 pages.

Non-final rejection, mailed from the United States Patent and Trademark Office dated Mar. 12, 2019, for U.S. Appl. No. 15/710,349, Naoyuki Haraguchi et al., "Endoscope,".

Final Office Action, dated Jun. 4, 2019, for U.S. Appl. No. 15/710,378, Haraguchi, "Endoscope," 23 pages.

* cited by examiner

FIG. 10

| | NOT ADDED | 1 WT% ADDED | 5 WT% ADDED |
|---|---|---|---|
| RESISTANCE VALUE Ω/cm | $1.8 \sim 5.0 \times 10^{13}$ | $2.5 \sim 3.0 \times 10^{13}$ | $3.5 \sim 5.0 \times 10^{10}$ |
| LIGHT SHIELDING COEFFICIENT (THICKNESS: 50 μm) | --- | 95% OR GREATER | 99% OR GREATER |

FIG. 13

| SURFACE | RADIUS OF CURVATURE (mm) | CONIC COEFFICIENT | THICKNESS (mm) | EFFECTIVE DIAMETER (mm) | REFRACTIVE INDEX | ABBE NUMBER |
|---|---|---|---|---|---|---|
| L1R1 | -1.911 | -6.528 | 0.565 | 0.8 | 1.59 | 59.8 |
| L1R2 | 0.599 | -3.381 | 0 | 0.5 | — | — |
| APERTURE STOP | ∞ | — | 0.050 | 0.2 | — | — |
| L2R1 | 0.513 | 0 | 0.416 | 0.25 | 1.80 | 40 |
| L2R2 | -0.493 | 0 | 0 | 0.7 | — | — |
| L3R1 | -1.629 | 0 | 0.398 | 0.8 | 1.68 | 31 |
| L3R2 | -214.043 | -54.512 | 0.460 | 0.8 | — | — |
| BONDING LAYER | — | — | 0.050 | 0.8 | 1.52 | 43 |

*FIG. 17A*
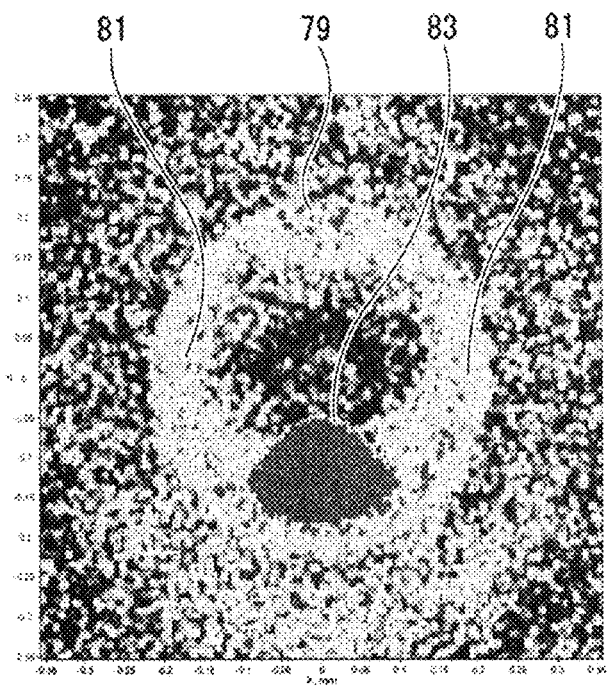
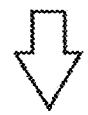
*FIG. 17B*
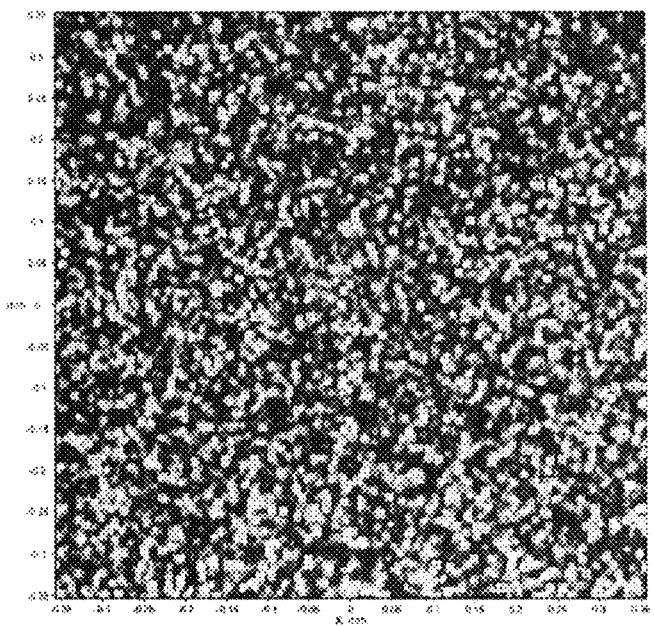

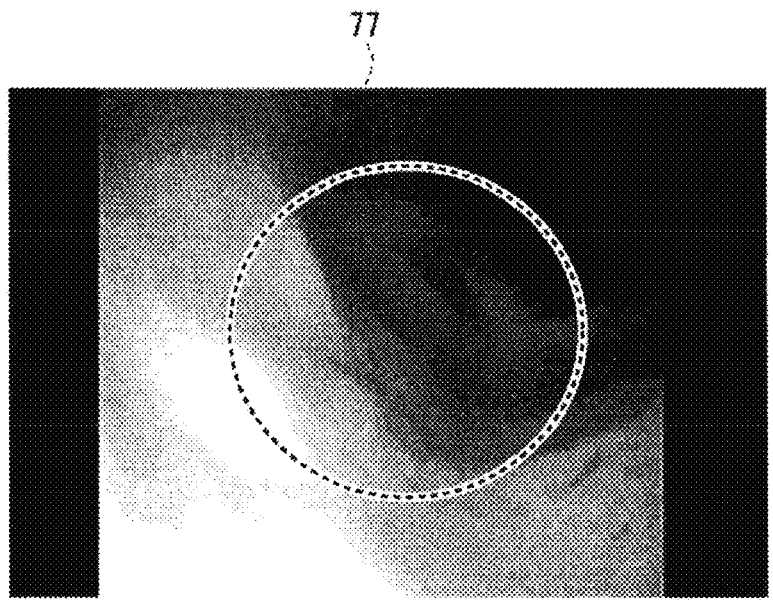
*FIG. 18A*
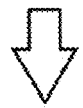
*FIG. 18B*

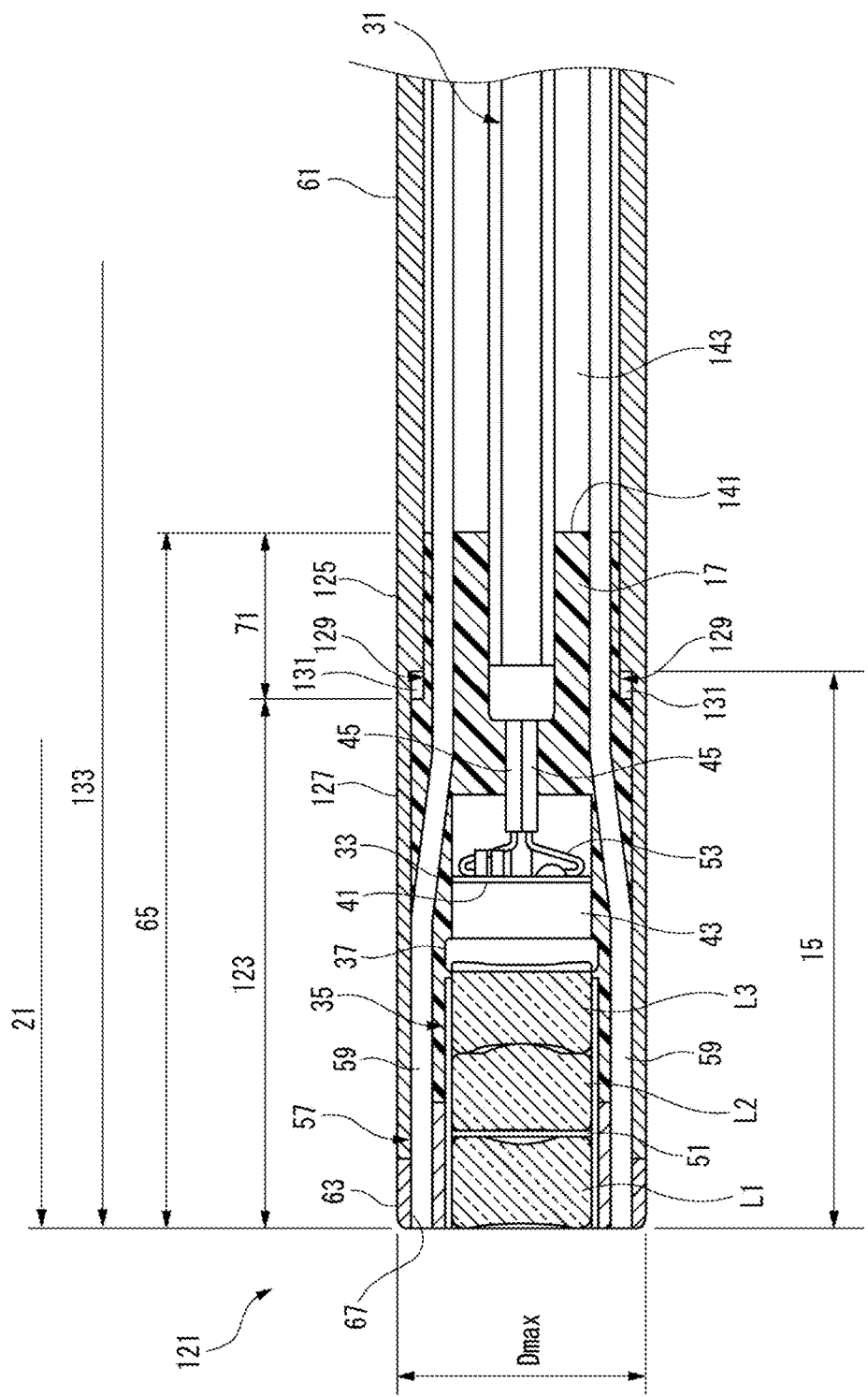

FIG. 31

|  | DISTAL END | CONNECTION PORTION | OTHER PORTION |
|---|---|---|---|
| SHORE D HARDNESS | 25~55 | 40~65 | 60~75 |

ENDOSCOPE

BACKGROUND

Technical Field

The present invention relates to an endoscope.

Description of the Related Art

In the related art, an endoscope, which captures an image of an internal organ of a patient's body or an inside of equipment or a structure, comes into wide use in the medical field or the industrial field. Light from an imaged site is imaged on a light-receiving area of an image sensor in an insertion part of this type of endoscope, which is inserted into an observed object, by an objective lens system. The endoscope converts the image forming light into electrical signals, and transmits the electrical signals, which are video signals, to an external image processing apparatus or the like via a signal cable.

In an endoscope used in the medical field, it becomes important that a thinner outer diameter of a distal insertion part inserted into the body of a patient is required so as to reduce a burden on the patient. In the related art, typically, the maximum outer diameter of a peroral endoscope is approximately 8 mm to approximately 9 mm. For this reason, during insertion, the peroral endoscope may be likely to come into contact with a tongue root, or may cause a patient to feel nausea or dyspnea. In recent years, a thin nasal endoscope quickly comes into wide use. The maximum outer diameter of the thin nasal endoscope is approximately one half of that of the peroral endoscope, that is, is approximately 5 mm to approximately 6 mm. For this reason, the thin nasal endoscope can be inserted into the nose. In many cases, since the maximum outer diameter is approximately 5 mm, which is thin, the thin nasal endoscope less causes vomiting reflex, and the insertion of the thin nasal endoscope does not matter much.

An electronic endoscopic system 501 disclosed in WO2013/031276 and illustrated in FIG. 33 mainly includes an endoscope 503; a light source device 505; a video processor 507; and a monitor 509. The endoscope 503 is configured to include a long and elongated insertion part 511; an operation unit 513; and a universal cable 515 which is an electric cable. The insertion part 511 of the endoscope 503 is configured to include a distal portion 517, a curved portion 519, and a flexible tubular portion 521 which are disposed sequentially from a distal side inserted into a patient. The operation unit 513 is configured to include an operation unit body 523, and a treatment tool channel insertion portion 525 through which various treatment tools are inserted into the insertion part 511. A curve operation knob 527 is disposed in the operation unit body 523 so as to curve the curved portion 519. The curve operation knob 527 includes a UD curve operation knob 529 that curves the curved portion 519 in an upward and downward direction, and an RL curve operation knob 531 that curves the curved portion 519 in a rightward and leftward direction.

An endoscope 533 disclosed in WO2013/146091 and illustrated in FIG. 34 includes an outer barrel 535 in a distal portion. An image mechanism 539 is provided on the outer barrel 535, and is covered with a filling light shielding material 537. The image mechanism 539 includes an image sensor 543 including a light-receiving portion 541 on one surface thereof; a cover member 545 that covers the surface on which the light-receiving portion 541 of the image sensor 543 is provided; a lens unit 547 that is optically combined to the light-receiving portion 541 of the image sensor 543; and a flexible printed wiring board 549. The lens unit 547 includes an objective cover member 551; an aperture stop 553; a plano-convex lens 555; a plan-convex lens 557; and a lens barrel 559 that fixes together these components which are disposed sequentially from an objective side. The plano-convex lens 557 is fixed to the cover member 545 with a bonding agent 561.

A further reduction in the outer diameter of an endoscope (for example, the thinning of the outer diameter of the distal insertion part disclosed in WO2013/031276, or of an insertion part on the objective side disclosed in WO2013/146091) is required. The further reduction in the outer diameter is based on such a medial demand that an operator desires to insert an endoscope into a site (for example, a very thin duct or hole such as a blood vessel) of the body of a patient into which it is difficult to insert existing thin nasal endoscopes including the aforementioned existing thin nasal endoscopes, and to observe the inside of the site in detail.

It is estimated from the exterior of the endoscope 503 (for example, a so-called flexible endoscope in which the insertion part 511 is flexible such that the insertion part 511 can be inserted into a digestive organ in the upper or lower part of a living body) illustrated in FIG. 1 and description of application examples in WO2013/031276 that the endoscope 503 disclosed in WO2013/031276 is an endoscope which is inserted into mainly a digestive tract of a human body. For this reason, it is difficult to insert the endoscope 503 into a very thin duct or hole such as a blood vessel of a human body, and to observe the inside of the duct or hole via the endoscope 503.

In the endoscope 533 disclosed in WO2013/146091, the sizes of the image sensor 543 and the flexible printed wiring board 549 of the image mechanism 539 are larger in a radial direction than the outer diameter of the lens barrel 559. In addition, the endoscope 533 is configured such that the outer barrel 535 accommodates the image mechanism 539 including these members, and the image mechanism 539 is covered with the light shielding material 537 with which the outer barrel 535 is filled. For this reason, a protrusion distance of the image sensor 543 and the flexible printed wiring board 549 which protrude outward from the lens barrel 559 in the radial direction, and the thickness of the outer barrel 535 are disadvantageous to a reduction of the size of the endoscope 533. Since the outer barrel 535 is required, the number of components increases, and the cost increases.

BRIEF SUMMARY

The present invention has an object to provide an endoscope with a reduced size (for example, the thinning of the outer diameter of a distal insertion part) and a reduced cost.

According to an aspect of the present invention, there is provided an endoscope including: at least one lens having a circular exterior shape in a direction perpendicular to an optical axis; an image sensor that has a square exterior shape in the direction perpendicular to the optical axis, and has one side whose length is same as length of a diameter of the lens; a sensor cover that covers an imaging area of the image sensor, has a square exterior shape in the direction perpendicular to the optical axis, and has one side whose length is same as one side length of the image sensor; a bonding resin portion that fixes the sensor cover to the lens, the optical axis of the lens coinciding with a center of the imaging area; a transmission cable connected to the image sensor; an illuminator provided along the lens and the transmission cable; a tubular sheath that covers a portion of the illuminator and the transmission cable; and a cover tube that covers the lens, the image sensor, and a portion of the illuminator, is coaxially connected to the tubular sheath in a state that outer circumferential surface is flush and continuous with outer circumferential surface of the tubular sheath, and forms a distal portion. The cover tube is smaller in thickness than the tubular sheath, and the distal portion including the lens, the illuminator, and the cover tube has a maximum outer diameter of 1.8 mm.

According to an aspect of the present invention, there is provided an endoscope including a single lens having a square exterior shape in a direction perpendicular to an optical axis; an image sensor that has an exterior shape which is same as an exterior shape of the single lens, in the direction perpendicular to the optical axis; a sensor cover that covers an imaging area of the image sensor, and has an exterior shape which is same as the exterior shape of the single lens, in the direction perpendicular to the optical axis; a bonding resin portion that fixes the sensor cover to the single lens, the optical axis of the lens coinciding with a center of the imaging area; a transmission cable connected to the image sensor; an illuminator provided along the single lens and the transmission cable; a tubular sheath that covers a portion of the illuminator and the transmission cable; and a molded portion that covers and fixes the single lens, the image sensor, and a portion of the illuminator, and forms a distal portion. The molded portion is coaxially and continuously connected to the tubular sheath, and the distal portion including the single lens, the illuminator, and the molded portion has a maximum outer diameter of 1.0 mm.

According to the present invention, it is possible to reduce the size and the cost of an endoscope.

BRIEF DESCRIPTION OF THE SEVERAL VIEWS OF THE DRAWINGS

FIG. 10 is a table illustrating an example of a relationship between the amount of addition of the additive to the molded part and the resistance value and the light shielding coefficient of the molded part.

FIG. 13 is a table illustrating lens data which indicates the optical characteristics of the lens unit illustrated in FIG. 12.

FIGS. 17A and 17B show measurement images obtained via illuminance distribution simulation which illustrates whether or not stray light is eliminated by providing a rough surface portion.

FIGS. 18A and 18B illustrate an example of captured images of an actual measurement result in which stray light is reduced by providing the rough surface portion.

FIG. 26 is a sectional view illustrating an example of a distal portion of an endoscope of a third embodiment.

FIG. 31 is a table illustrating an example of hardness values at positions on an insertion part.

DETAILED DESCRIPTION

Hereinafter, specific embodiments of an endoscope of the present invention will be suitably described in detail with reference to the accompanying drawings. Unnecessary detailed description may be omitted. For example, detailed description of already well-known items or duplicated description of substantially the same configuration elements may be omitted. The reason for this is to avoid that the following description becomes unnecessarily lengthy, and to help persons skilled in the art easily understand this disclosure. The accompanying drawings and the following description are provided to help persons skilled in the art fully understand this disclosure, and are not intended to limit the concept described in the claims.

First, a basic configuration example common to the endoscopes of the embodiments will be described. A configuration example illustrates configuration elements that the endoscope of the present invention may include. It is not excluded that the endoscope of the present invention has a configuration which is a combination of the following configuration examples.
(First Embodiment)
<Basic Configuration Example>

Figure 1:
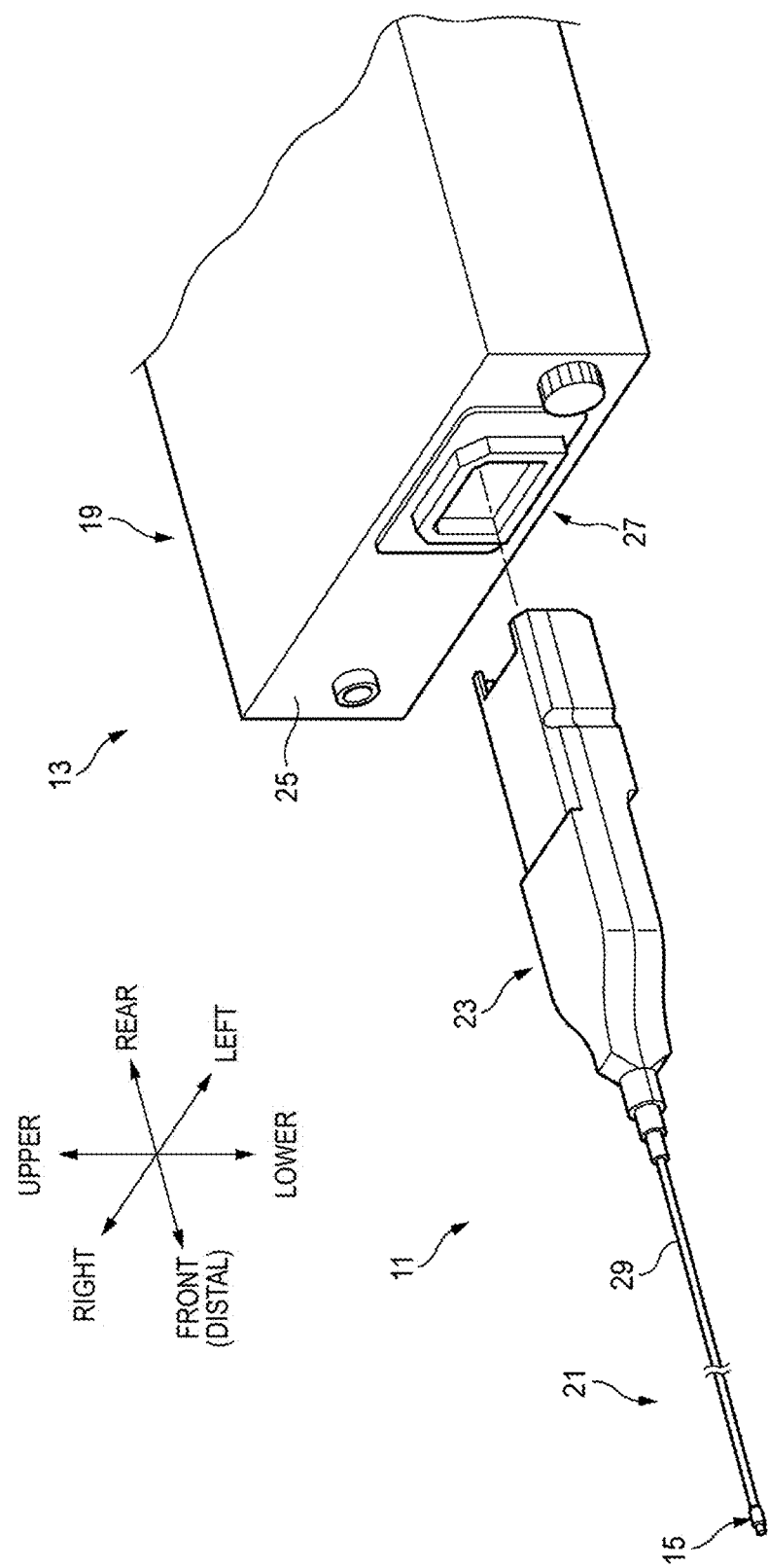
FIG. 1 is a view illustrating an example of the entire configuration of an endoscopic system including an endoscope of each embodiment.

FIG. 1 is a view illustrating an example of the entire configuration of an endoscopic system including the endoscope of each embodiment. FIG. 1 is a perspective view illustrating the entire configuration of an endoscopic system 13 including an endoscope 11 and a video processor 19.

Directions referred in the description of the specification are as defined in each drawing. An "upper side" and a "lower side" respectively correspond to upper and lower sides of the video processor 19 placed on a horizontal surface. A "front (distal)" and a "rear side" respectively correspond to a distal side of an insertion part 21 and a proximal side (in other words, video processor 19 side) of a plug portion 23 of an endoscope body (hereinafter, referred to as the "endoscope 11").

As illustrated in FIG. 1, the endoscopic system 13 includes the endoscope 11 which is a medical flexible endoscope, and the video processor 19 that performs well-known image processing on captured still or moving images of the inside (for example, blood vessel of a human body) of an observed object.

The endoscope 11 extends substantially in a forward and rearward direction. The endoscope 11 includes the insertion part 21 inserted into the observed object, and the plug portion 23 connected to a rear portion of the insertion part 21.

The video processor 19 includes a socket portion 27 that opens in a front wall 25. A rear portion of the plug portion 23 of the endoscope 11 is inserted into the socket portion 27 such that the endoscope 11 is capable of transmitting to and receiving electric power and various signals (video signals, control signals, and the like) from the video processor 19.

The electric power and the various signals are guided from the plug portion 23 to a soft portion 29 via a transmission cable 31 (refer to FIG. 3 or 4) inserted into the soft portion 29. Image data, which is output from an image sensor 33 provided in a distal portion 15, is transmitted from the plug portion 23 to the video processor 19 via the transmission cable 31. The video processor 19 performs well-known image processing such as color correction and gradation correction on the image data transmitted from the plug portion 23, and outputs the processed image data to a display apparatus (not illustrated). The display apparatus is a monitor apparatus including a display device such as a liquid crystal display panel. The display apparatus displays an image (for example, image data illustrating the inner status of a blood vessel of a human which is a subject) of a subject captured by the endoscope 11.

The insertion part 21 includes the flexible soft portion 29, the rear end of which is connected to the plug portion 23, and the distal portion 15 that is continuous with a distal end of the soft portion 29. The soft portion 29 has a length suitable for coping with various endoscopic examinations, various endoscopic surgeries, and the like. The soft portion 29 is configured by covering an outer circumference of a spirally wound thin metal plate with a net, and applying a coating to the outer circumference covered with the net. The soft portion 29 is formed to have sufficient flexibility. The distal portion 15 is connected to the plug portion 23 via the soft portion 29.

Since the endoscope 11 and an endoscope 111 of each embodiment to be described below are formed to be thin, the endoscope 11 or 111 can be inserted into a thin body cavity. The thin body cavity is not limited to a blood vessel of a human body. The examples of the thin body cavity include the ureter, the pancreatic duct, the bile duct, and a bronchiole. That is, the endoscope 11 or 111 can be inserted into a blood vessel, the ureter, the pancreatic duct, the bile duct, and a bronchiole of a human body. In other words, the endoscopes 11 and 111 can be used to observe lesions inside a blood vessel. The endoscopes 11 and 111 are effective in identifying atherosclerotic plaque. The endoscopes 11 and 111 can also be applied to cardiac catheterization via an endoscopic observation. In addition, the endoscopes 11 and 111 are effective in detecting a thrombus or atherosclerotic yellow plaque. The color tone (white, light yellow, or yellow) or the surface (smooth or irregular surface) of an atherosclerotic lesion is observed. The color tone (red, white, dark red, yellow, brown, or mixed color) of a thrombus is observed.

The endoscopes 11 and 111 can be used in the diagnosis and treatment of the renal pelvis and ureter cancer or idiopathic renal bleeding. In this case, an operator can observe the inside of a ureter and the renal pelvis by inserting the endoscope 11 or 111 into the bladder from the urethra, and moving the endoscope 11 or 111 forward to the ureter.

The endoscope 11 or 111 can be inserted into the papilla of Vater which opens in the duodenum. Bile is produced in the liver, and is discharged from the papilla of Vater in the duodenum via the bile duct. Pancreatic juice is produced in the pancreas, and is discharged from the papilla of Vater in the duodenum via the pancreatic duct. An operator can observe the bile duct or the pancreatic duct by inserting the endoscope 11 or 111 via the papilla of Vater which is an opening portion of the bile duct and the pancreatic duct.

In addition, the endoscope 11 or 111 can be inserted into the bronchus. The endoscope 11 or 111 is inserted via the oral cavity or the nasal cavity of a clinical specimen (that is, patient) in a supine position. An operator inserts the endoscope 11 or 111 to the trachea through the pharynx and the larynx while viewing the vocal cords. The bronchus becomes thin whenever the bronchus is bifurcated. An operator can confirm the lumen of a subsegmental bronchus via the endoscopes 11 and 111 having a maximum outer diameter Dmax of 2 mm or less.

Hereinafter, various configuration examples of the endoscope of a first embodiment will be described. The endoscope 11 of each embodiment may have any configuration of first to twenty-sixth configuration examples.

Figure 2:
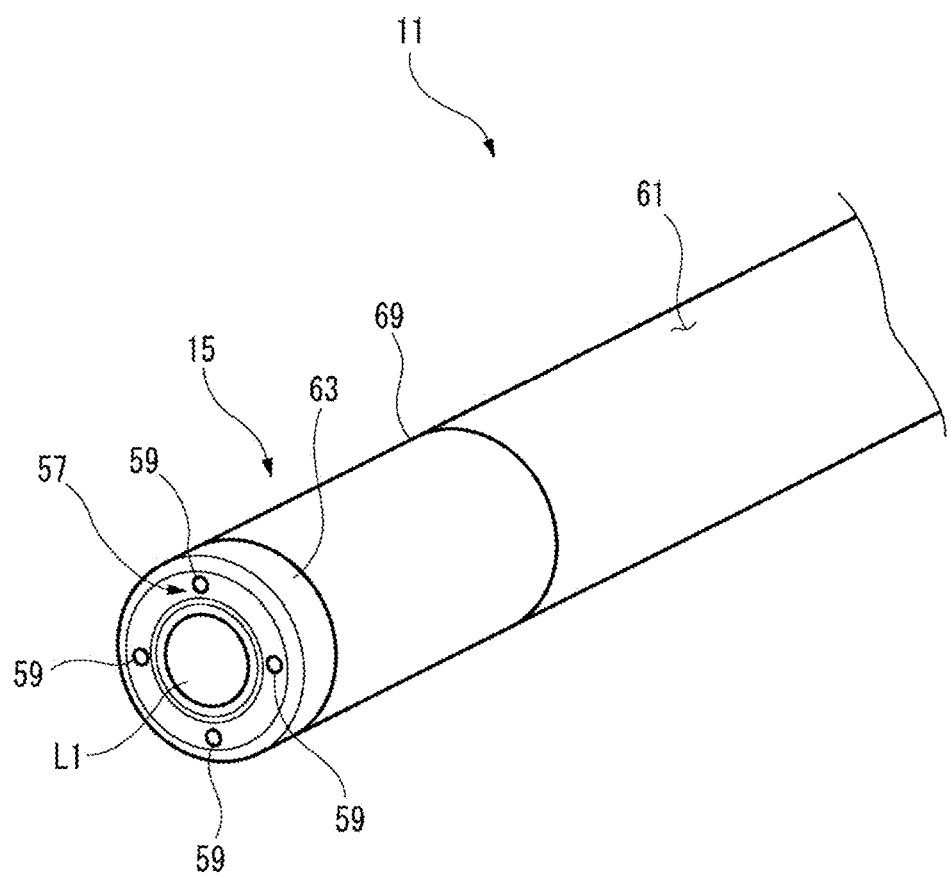
FIG. 2 is a perspective view of a distal portion of an endoscope of a first embodiment which is viewed from the front side.
Figure 3:
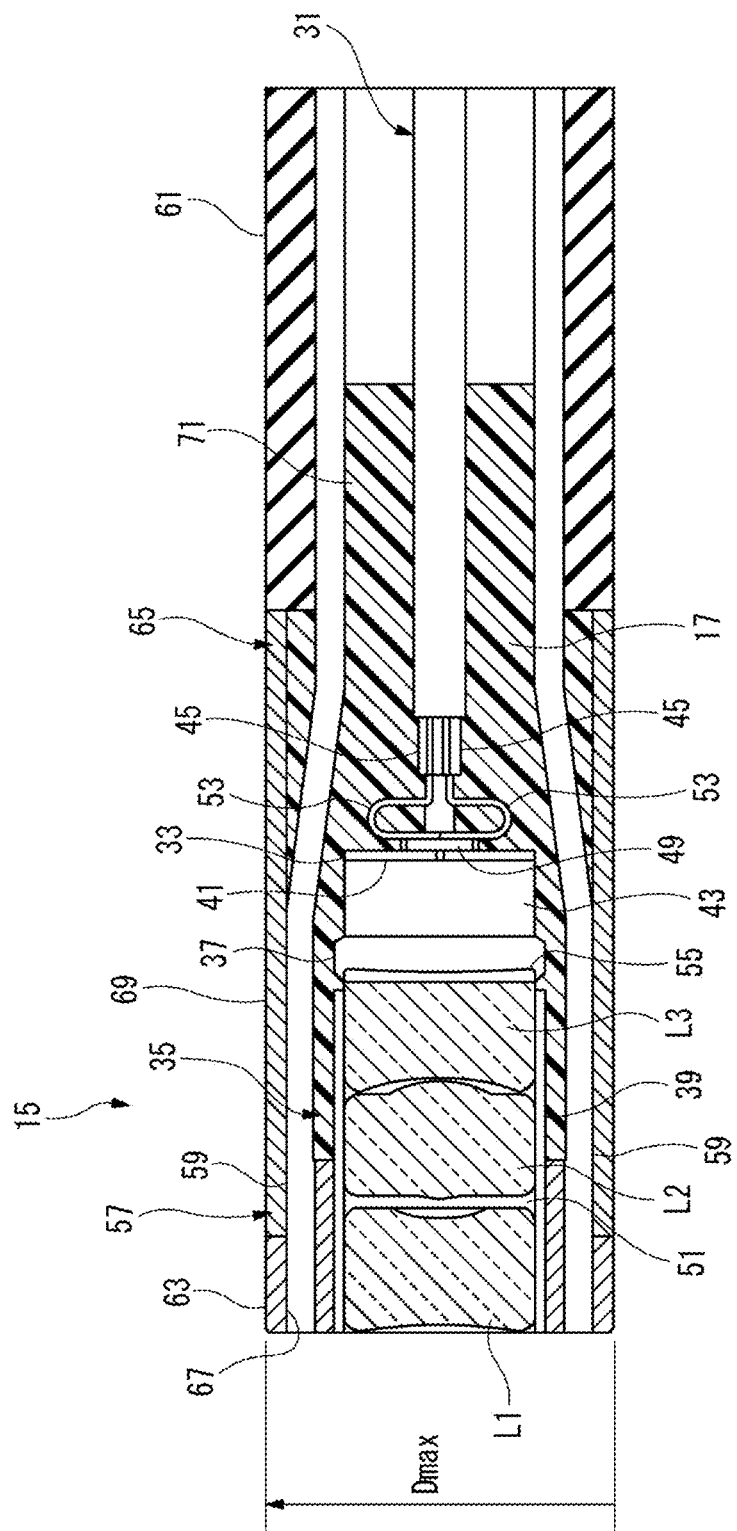
FIG. 3 is a sectional view illustrating an example of the distal portion of the endoscope of the first embodiment.
Figure 4:
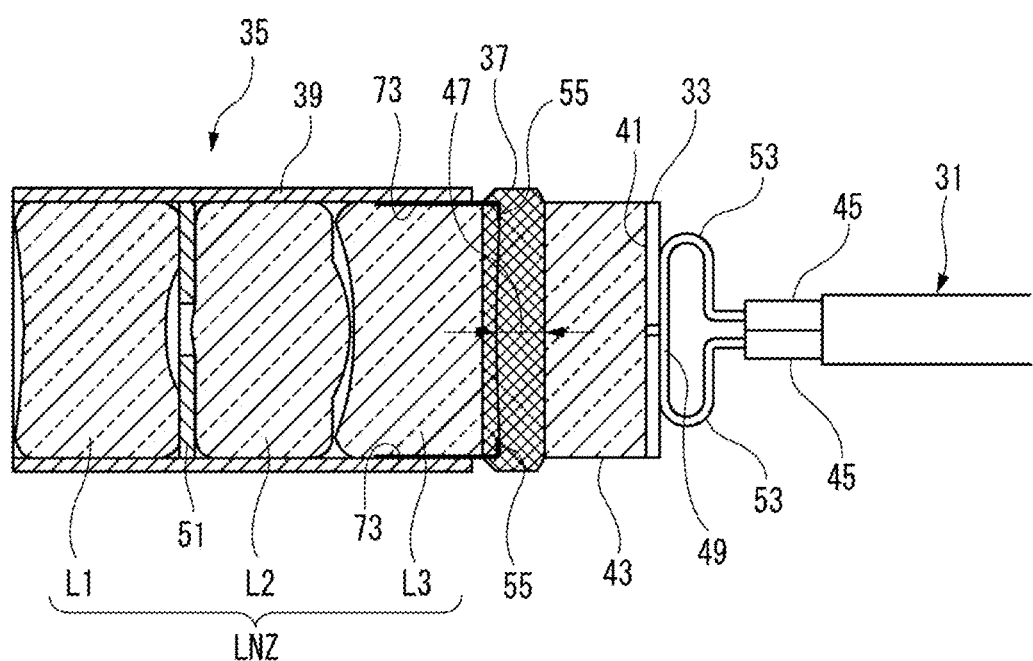
FIG. 4 is a sectional view illustrating an example of a configuration in which a separation part of the endoscope of the first embodiment is filled with bonding resin.
Figure 5:
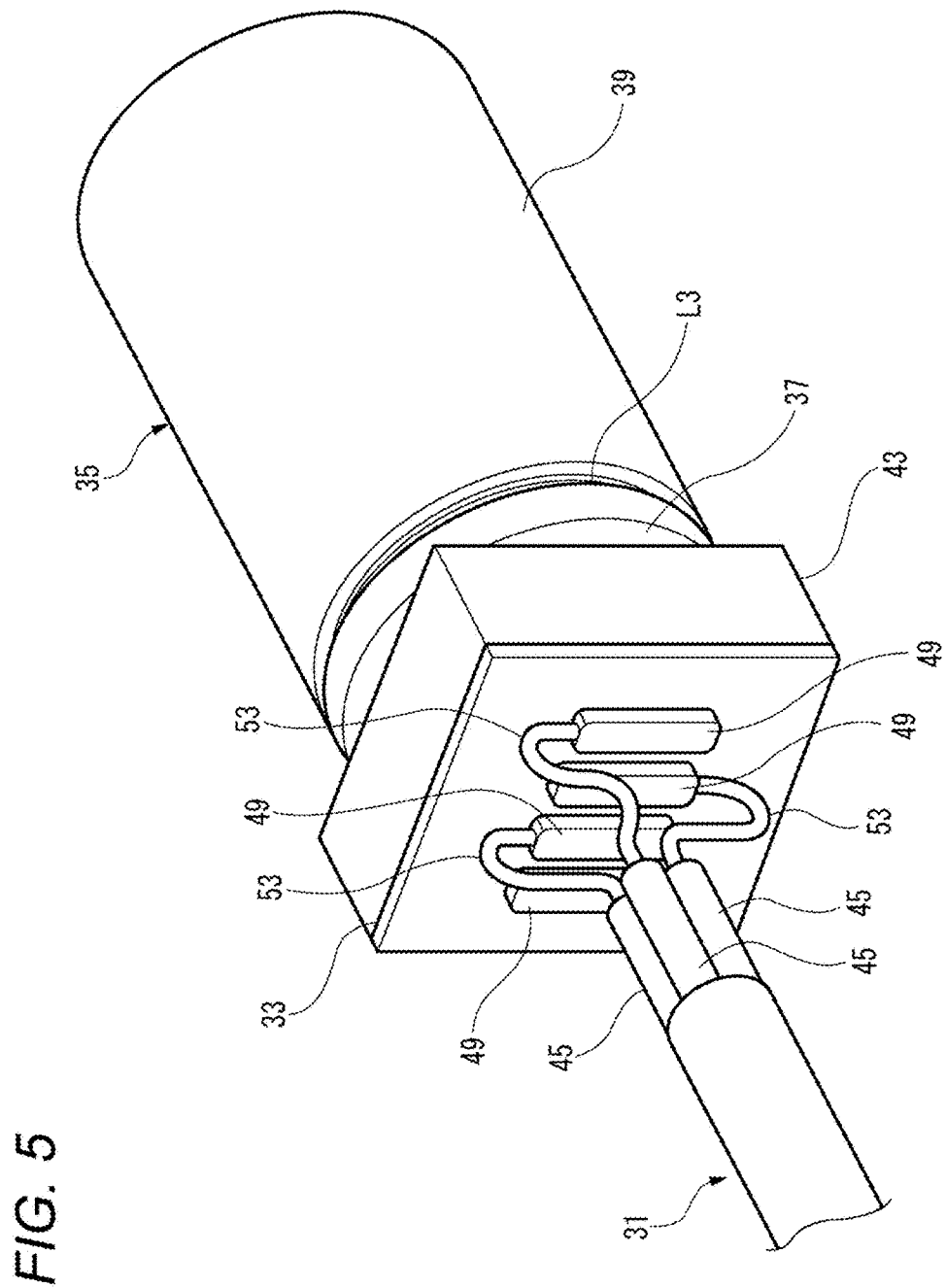
FIG. 5 is a perspective view of an image sensor which is viewed from the rear side, which illustrates a state in which a transmission cable is connected to a conductor connection part of the endoscope of the first embodiment.

FIG. 2 is a perspective view of the distal portion 15 of the endoscope 11 of the first embodiment which is viewed from the front side. FIG. 3 is a sectional view illustrating an example of the distal portion 15 of the endoscope 11 of the first embodiment. FIG. 4 is a sectional view illustrating an example of a configuration in which a separation part 47 of the endoscope 11 of the first embodiment is filled with bonding resin 37. FIG. 5 is a perspective view of the image sensor 33 which is viewed from the rear side, which illustrates a state in which the transmission cable 31 is connected to a conductor connection part 49 of the endoscope 11 of the first embodiment.

FIG. 2 is a perspective view illustrating a configuration of the distal portion 15 of the endoscope 11 illustrated in FIG. 1. FIG. 3 is a sectional view illustrating the configuration of the distal portion 15 illustrated in FIG. 2. FIG. 4 is a sectional view illustrating the configuration of the distal portion 15 illustrated in FIG. 2 from which molded resin 17 is removed. FIG. 5 is a perspective view illustrating the configuration of the image sensor 33 illustrated in FIG. 4 which is viewed from an opposite side of a lens unit 35.

<First Configuration Example>

The endoscope 11 of the first configuration example includes the lens unit 35 in which lenses are accommodated in a lens support member 39; the image sensor 33, the imaging area of which is covered with sensor cover glass 43; the bonding resin 37 with which the lens unit 35 is fixed to the sensor cover glass 43 in a state where the optical axes of the lenses coincide with the center of the imaging area; and the transmission cable 31 including four electric cables 45 which are respectively connected to four conductor connection parts 49 provided on a surface opposite to the imaging area of (surface on the rear side of) the image sensor 33.

Multiple (three in the illustrated example) lenses L1 to L3 formed of an optical material (for example, glass or resin) and an aperture stop 51 interposed between the lenses L1 and L2 are assembled into the lens support member 39 while being proximate to each other in the direction of the optical axis. The aperture stop 51 is provided so as to adjust the amount of light incident to the lens L2 or L3. Only light passing through the aperture stop 51 can be incident to the lens L2 or L3. The proximity means that one lens and the other lens are slightly separated from each other so as to avoid scratches caused by contact between the lenses. The entire circumferences of the lenses L1 to L3 are fixed to an inner circumferential surface of the lens support member 39 with a bonding agent.

The term "bonding agent" in the following description does not represent only a substance used to bond together surfaces of solid objects in a strict sense, but also, in a wide sense, represents a substance capable of joining together two objects, or a substance that acts as a sealing material if the hardened bonding agent has high barrier properties against gas and liquid.

A front end and a rear end of the lens support member 39 are respectively blocked (sealed) by the lens L1 and lens L3 such that air, moisture, or the like is not allowed to infiltrate into the lens support member 39. As a result, air or the like is not capable of escaping from one end to the other end of the lens support member 39. In the following description, the lenses L1 to L3 are collectively referred to as an optical lens group LNZ.

For example, nickel is used as the metal material of the lens support member 39. Since nickel has a relatively high modulus of rigidity and high corrosion resistance, nickel is suitable as the material of the distal portion 15. In an examination or a surgery using the endoscope 11, preferably, the circumference of the lens support member 39 is uniformly coated with the molded resin 17, and a biocompatible coating is applied to the distal portion 15 before the examination or the surgery such that nickel of the lens support member 39 is not directly exposed from the distal portion 15. Instead of using nickel, for example, a copper nickel alloy may be used. Since a copper nickel alloy has high corrosion resistance, the copper nickel alloy is suitable as the material of the distal portion 15. The metal material of the lens support member 39 is preferably selected from materials which can be manufactured via electroforming (electroplating). The reason for the use of electroforming is that a member manufactured via electroforming has a dimensional accuracy of 1 μm or less (so-called submicron accuracy), which is a very high accuracy, and a variation in the dimensions of a large number of manufactured members is small. Stainless steel (for example, SUS316) may be used as the metal material of the lens support member 39. Stainless steel (also referred to as a SUS tube) has high biocompatibility. It is considered that stainless steel is suitable as the material of an endoscope inserted into a thin site such as a blood vessel of a human body. The lens support member 39 is a very small member. Errors in inner and outer diameter dimensions affect the optical performance (that is, image quality of a captured image) of the endoscope 11. If the lens support member 39 is configured of a electroformed nickel tube, it is possible to ensure a high dimensional accuracy in spite of a fact that the lens support member 39 has a small diameter. As a result, it is possible to obtain the endoscope 11 capable of capturing high quality images.

The lens support member 39 may be made of a sheet material other than metal. The lens support member 39 may be positioned when the optical axes of the lenses of the lens unit 35 coincide with each other. If the lens unit 35 is covered with the molded resin 17, the positions of the lenses relative to each other are fixed. For this reason, the lens support member 39 may be made of a material having low strength, a thin thickness, and a light weight compared to those of the material of a barrel used to support multiple lenses in the related art. As a result, this material is capable of contributing to the thinning of the distal portion 15 of the endoscope 11. It is not ruled out that the same metallic barrel as that in the related art is used as the lens support member 39.

As illustrated in FIG. 5, the image sensor 33 is configured as an image device such as a small charge coupled device (CCD) or a small complementary metal-oxide semiconductor (CMOS) which has a square shape when the image device is seen from the forward and rearward direction. Light incident from the outside is imaged on an imaging area 41 of the image sensor 33 by the optical lens group LNZ inside the lens support member 39. The imaging area 41 of the image sensor 33 is covered with the sensor cover glass 43.

For example, the bonding resin 37 is configured of UV and thermosetting resin. The bonding resin 37 preferably has light transmitting properties, and a refractive index close to that of air. If UV and thermosetting resin is used as the bonding resin 37, it is possible to harden an exterior surface portion of the bonding resin 37 via ultraviolet light irradiation, and it is possible to harden the inside of the filling bonding agent, which cannot be irradiated with ultraviolet light, via a heat treatment. In a state where the optical axes of the lenses coincide with the center of the imaging area 41, the lens unit 35 is fixed to the sensor cover glass 43 with the bonding resin 37. As a result, the lens unit 35 is directly bonded and fixed to the image sensor 33 with the bonding resin 37, that is, the lens unit 35 is directly attached to the image sensor 33 via the bonding resin 37. The bonding resin 37 is a bonding agent, the heat treatment of which is required so as to obtain a final hardness, and the hardening of which progresses to a certain degree of hardness via only ultraviolet light irradiation.

If a light emitting surface of the lens facing the sensor cover glass 43 is a convex surface, in the endoscope 11, an edge portion 55, which is an annular end surface on the circumference of the lens, is bonded to the sensor cover glass 43. In this case, outer circumferences of the lenses and an outer circumference of the lens support member 39 may be simultaneously fixed with the bonding resin 37. If the edge portion 55 of the lens is bonded to the sensor cover glass 43, an air layer is provided between the lenses and the image sensor 33. Since the air layer is provided between the lenses and the image sensor 33, it is possible to improve the optical performance of the lenses. For example, it is possible to increase a refractive index difference of light emitted from the lenses to the air layer, and it is possible to obtain power for refracting light. Accordingly, optical design such as improving a resolution and increasing an angle of view becomes easy. As a result, the image quality of an image captured by the endoscope 11 improves.

The four conductor connection parts 49 are provided on a back surface side rear portion of the image sensor 33. For example, the conductor connection part 49 may be formed of a land grid array (LGA). The four conductor connection parts 49 are made up of a pair of electric power connection parts and a pair of signal connection parts. The four conductor connection parts 49 are electrically connected to the four electric cables 45 of the transmission cable 31, respectively. The transmission cable 31 includes a pair of electric power cables which are the electric cables 45, and a pair of signal cables which are the electric cables 45. That is, the pair of electric power cables of the transmission cable 31 are respectively connected to the pair of electric power connection parts of the conductor connection part 49. The pair of signal cables of the transmission cable 31 are respectively connected to the pair of signal connection parts of the conductor connection part 49.

As described above, in the endoscope 11 of the first configuration example, the lens unit 35 and the image sensor 33 are fixed together with the bonding resin 37 in a state where a predetermined distance between the lens unit 35 and the image sensor 33 is held. If the lens unit 35 and the image sensor 33 are fixed together, the optical axis of the lens unit 35 is position-aligned with the center of the imaging area 41. The positions of the lens unit 35 and the image sensor 33 relative to each other are aligned at a distance therebetween at which light, which is incident from a subject and passes through the lens unit 35, is focused on the imaging area 41 of the image sensor 33. The lens unit 35 and the image sensor 33 are fixed together after position alignment therebetween.

The separation part 47 (refer to FIG. 4) is formed between the lens unit 35 and the image sensor 33 which are fixed together. If the positions of the lens unit 35 and the image sensor 33 are aligned relative to each other, and are fixed together with the bonding resin 37, the shape of the separation part 47 is determined. That is, the separation part 47 acts as an adjustment gap for position alignment between the lens unit 35 and the image sensor 33. Even if the separation part 47 is filled with the bonding resin 37, the adjustment gap is not lost. In the specific dimensional example, the separation part 47 is adjusted between at least approximately 30 µm and approximately 100 µm. At this time, a tolerance is ±20 µm. Accordingly, in this case, the minimum adjustment gap becomes 10 µm which is the remainder.

After the separation part 47 becomes an adjustment gap, and position alignment between the lens unit 35 and the image sensor 33 is complete, in the endoscope 11, the separation part 47 is used as a fixing space of the bonding resin 37. For this reason, the lens unit 35 can be directly fixed to the image sensor 33. Accordingly, it is not necessary to provide an interposed member such as a frame or a holder which is required to fix the lens unit 35 to the image sensor 33 in the related art. Since a frame, a holder, or the like can be omitted, the number of components is reduced, and a fixing structure becomes simplified. As a result, it is possible to reduce the diameter of the distal portion 15 of the endoscope 11. Also, in a case where a further reduction in the diameter of the distal portion 15 is attempted (for example, the thinning of the outer diameter of a distal insertion part is attempted), it is possible to configure the distal portion 15 with the minimum dimensions. In addition, it is possible to reduce component costs. Since the number of interposed components for fixing the lens unit 35 to the image sensor 33 is small, it is possible to reduce man hours required to perform position alignment and fixing work, and it is possible to easily perform position alignment with high accuracy. It is possible to reduce manufacturing costs, and to improve productivity.

In the endoscope 11, the transmission cable 31 including the four electric cables 45 is connected to the image sensor 33. Since the transmission cable 31 includes the four electric cables 45, it is possible to reduce both the size and the cost of the endoscope 11. For example, the transmission cable 31 may be configured to include less than four (for example, three) electric cables 45 due to a disposition space of the conductor connection parts 49 on the back surface side rear portion of the image sensor 33. In this case, if one signal cable is omitted, a captured image signal or a control signal transmitted from the video processor 19 has to be superimposed on an electric power waveform passing through the electric power cables. In this case, a modulation circuit, a demodulation circuit, or the like is required for signal superimposition, and thus, the number of components increases, and the total cost increases. If signal cables dedicated to transmit and receive various signals (captured image signal, control signal, and the like) are used, it is easy to configure a circuit, but the dedicated signal cables are disadvantageous to the thinning of the endoscope. In contrast, if the transmission cable 31 is configured to include more than four (for example, five) electric cables 45, a disposition space of each of the conductor connection parts 49 on the back surface side rear portion of the image sensor 33 becomes narrow. In a case where the endoscope 11 including the distal portion 15 having the maximum outer diameter of 1.8 mm or less is manufactured which will be described later, it is difficult to perform connection work via soldering, and it is difficult to manufacture the endoscope 11. As described above, since the transmission cable 31 is configured to include the four electric cables 45, this configuration is very effective in reducing both the size and the cost of the endoscope 11.

<Second Configuration Example>

In the endoscope 11 of the second configuration example in the embodiment, the maximum outer diameter Dmax of the distal portion 15 may be set to a range from 1.8 mm to a finite diameter equivalent to the diameter of a circumscribed circle of a substrate of the image sensor 33 which can be obtained via dicing.

In the endoscope 11 of the embodiment, an image sensor, one side of which has a dimension of 1.0 mm is used as the image sensor 33 having a square section in a direction perpendicular to the optical axis. As a result, the image sensor 33 has a diagonal dimension of approximately 1.4 mm, and the maximum outer diameter Dmax of the endoscope 11 including a light guide 57 (for example, having 150 microns φ) as an illuminator may be set to 1.8 mm or less.

As described above, since the maximum outer diameter Dmax is set to less than 1.8 mm, the endoscope 11 of the second configuration example can be easily inserted into a blood vessel of a human body.

<Third Configuration Example>

In the endoscope 11 of the third configuration example in the embodiment, as illustrated in FIG. 5, the substrate of the image sensor 33 is formed into a square shape, and the four conductor connection parts 49 are disposed in a row along one side of the substrate of the image sensor 33. Each one of the conductor connection parts 49 is formed into a rectangular shape. The four conductor connection parts 49 are disposed spaced from each other while long sides of the four conductor connection parts 49 are parallel to each other. The four conductor connection parts 49 are disposed in a central portion of the substrate of the image sensor 33. As a result, the conductor connection parts 49 are spaced from a circumferential edge of the substrate of the image sensor 33.

A conductor of each of the electric power cables and the signal cables, which are the electric cables 45 of the transmission cable 31, is covered with an insulation coating. One transmission cable 31 is formed by disposing two sets of the four electric cables 45 on the right and left sides and in two stages in the upward and downward direction, and binding outer circumferences of the insulation coatings with an outer cover. Each conductor includes a bent portion 53 that is bent in a U shape along a longitudinal direction of the conductor connection part 49. The electric cable 45 is in contact with the conductor connection part 49 in a state where the bent portion 53 is pre-formed. A distal end of the bent portion 53 of the electric cable 45 is connected to the conductor connection part 49 via soldering. The image sensor 33 and the transmission cable 31 are covered with the molded resin 17. As a result, the conductor connection parts 49, the bent portions 53, the electric cables 45, and the outer cover of the transmission cable 31 are embedded in the molded resin 17.

As described above, in the endoscope 11 of the third configuration example, since the four conductor connection parts 49 can be disposed in the central portion of the substrate of the image sensor 33 while being parallel to each other, it is easy to form the conductor connection parts 49. Since the conductors of the electric cables 45 are respectively connected to the four conductor connection parts 49, which are spaced from each other in one direction, via soldering, it is possible to easily perform connection work. Since the conductor connection parts 49 are disposed in the central portion of the substrate of the image sensor 33, it is possible to form the bent portion 53 in each conductor. Since the bent portions 53 are embedded in and fixed to a molded part 65, it is possible to reduce the application of tension, which is applied to the transmission cable 31, to joint portions between the conductors and the conductor connection parts 49 (in such a way as to work as a strain relief). As a result, it is possible to improve connection reliability between the electric cables 45 and the conductor connection parts 49.

<Fourth Configuration Example>

In the endoscope 11 of the fourth configuration example in the embodiment, an illuminator is provided along the lens unit. That is, the endoscope 11 of the fourth configuration example includes the light guide 57 as an example of the illuminator. In the following description, the light guide 57 is exemplified as the illuminator. Alternatively, the illuminator may be an LED directly attached to an insertion distal surface of the distal portion 15. In this case, the light guide 57 is not required.

The light guide 57 is formed of one optical fiber 59. For example, a plastic optical fiber (POF) is preferably used as the optical fiber 59. The material of a plastic optical fiber is silicon resin or acrylic resin, and both a core and a clad of the plastic optical fiber is formed of plastic. The optical fiber 59 may be a bundle fiber that is obtained by bundling together multiple optical fiber strands, and attaching terminal metal fittings to both ends of the optical fiber strands. A distal end of the optical fiber 59 becomes a light emitting end surface of the distal portion 15, and a proximal end of the optical fiber 59 is connected to the plug portion 23. For example, a light source is an LED provided in the socket portion 27 or the like. If the plug portion 23 is connected to the socket portion 27, in the endoscope 11, light from the LED propagates through the optical fiber 59 of the light guide 57, and is emitted from the distal end of the optical fiber 59. In this configuration, the optical fiber 59 may be configured as one optical fiber from the light source to an illumination light emitting end, and it is possible to reduce an optical loss.

As described above, since the endoscope 11 of the fourth configuration example includes the light guide 57, the endoscope 11 alone is capable of capturing an image of a dark site.

<Fifth Configuration Example>

Figure 6:
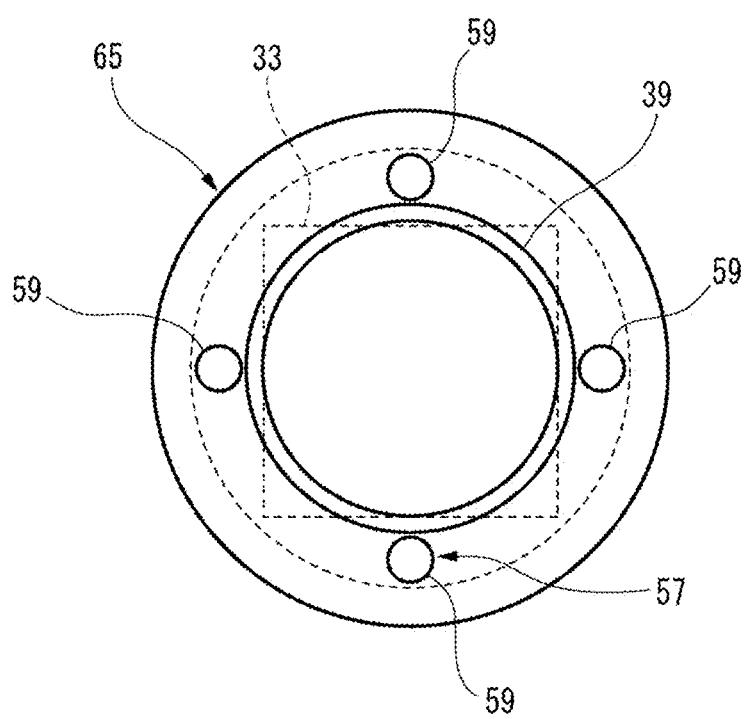
FIG. 6 is a front view illustrating an example of the distal portion in which light guides as an example of a illuminator are disposed.

FIG. 6 is a front view illustrating an example of the distal portion in which the light guides 57 as an example of the illuminator are disposed. The endoscope 11 of the fifth configuration example in the embodiment has a configuration in which multiple light guides 57 as an example of the illuminator are provided in a circumferential direction of the lens unit 35. Four light guides 57 are provided equally spaced from each other in the circumferential direction of the lens unit 35.

As described above, since the four light guides 57 are provided equally spaced from each other in the circumferential direction of the lens unit 35, the endoscope 11 of the fifth configuration example is unlikely to cast a shadow to the upper, lower, right, and left sides of a subject. As a result, the endoscope 11 is capable of capturing a clear image in comparison with that captured by an endoscope including one light guide 57 or two light guides 57.

<Sixth Configuration Example>

In the endoscope 11 of the sixth configuration example in the embodiment, the image sensor 33 is formed into a square shape. The optical fiber 59 of each of the four light guides 57 are disposed at substantially the center of each side portion of the substrate of the image sensor 33 in a space interposed between the substrate of the image sensor 33 and the circumscribed circle of the substrate of the image sensor 33.

As described above, in the endoscope 11 of the sixth configuration example, it is possible to effectively use a space interposed between the square image sensor 33 and the circular molded part 65 substantially circumscribed to the image sensor 33. It is possible to easily dispose multiple (particularly, four) optical fibers 59 without increasing the outer diameter of the distal portion 15. As a result, it is possible to easily manufacture the endoscope 11 without increasing the outer diameter of the distal portion 15. The endoscope 11 is capable of capturing a clear image.

<Seventh Configuration Example>

In the endoscope 11 of the seventh configuration example in the embodiment, at least a portion of the lens unit, the image sensor, a portion of the transmission cable, and a portion of the illuminator are coated with and are fixed by molded resin. The molded part 65 is configured of a molded resin material containing an additive such that light transmittance can be set to 10% or less.

Figure 7:
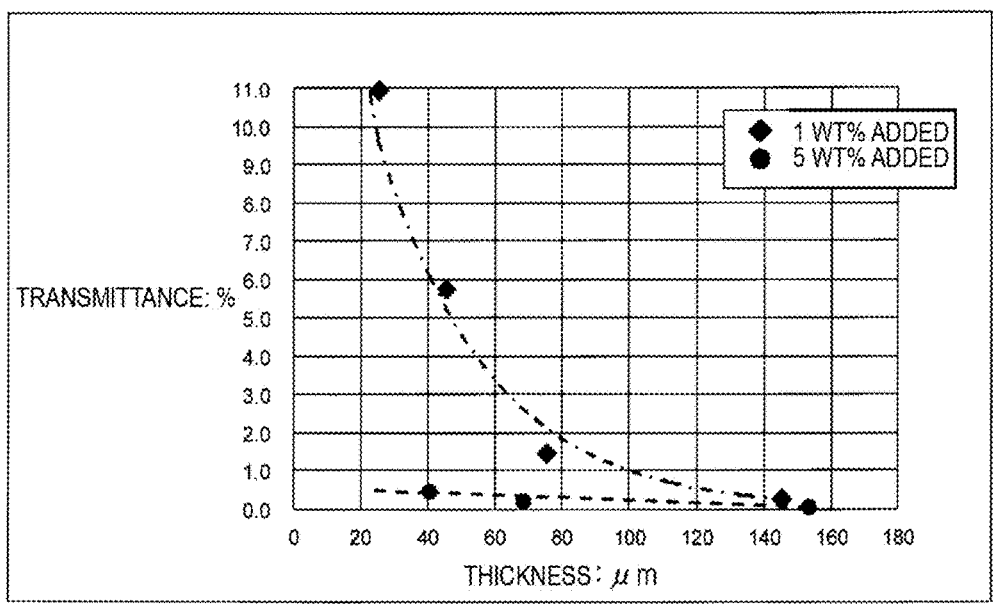
FIG. 7 is a characteristic graph illustrating an example of a relationship between the thickness and the transmittance of a molded part.

FIG. 7 is a characteristic graph illustrating an example of a relationship between the thickness and the transmittance of the molded part 65. FIG. 7 illustrates an example of the measurement of transmittance in a case where carbon black as an additive is added to a molded resin material (epoxy resin). In FIG. 7, a dotted line with black circles illustrates a case in which 5% by weight (wt. %) carbon black is added, and an alternate one lone and two short dashes line with black rhomboids illustrates a case in which 1% by weight (wt. %) carbon black is added.

If 5% by weight carbon black is added, the light transmittance is almost independent of the magnitude of the thickness of the molded part 65. Even if the thickness is 30 μm or less, it is possible to obtain high light shielding performance, that is, a light transmittance of approximately 0.5% (light shielding coefficient of 99.5%). If 1% by weight carbon black is added, the light transmittance increases as the thickness of the molded part 65 decreases. If 1% by weight carbon black is added, and the thickness of the molded part 65 is 30 μm or greater, the light transmittance can be reduced to 8.0% or less. Accordingly, if the thickness T of the molded part 65 is set to 30 μm or greater, a condition of a light transmittance of 10% or less can be fully satisfied. For example, if the thickness of the molded part 65 is set to 50 μm or greater, a light transmittance of 4.5% or less is obtained in a case where 1% by weight carbon black is added, and a light transmittance of 0.5% or less is obtained in a case where 5% by weight carbon black is added. Therefore, the molded part 65 is capable of more reliably shielding light.

If the light transmittance of the molded part 65 is 10% or less, an image unit including the lens unit 35 and the image sensor 33 is capable of capturing a good quality image that is not much affected by stray light. In a case where the light transmittance of the molded part 65 is 6% or less, even if the image sensor 33 has a high sensitivity, it is possible to prevent stray light from affecting the quality of an image. If the light transmittance is greater than 10%, a captured image is affected by stray light, and has a defect.

Figure 8A:
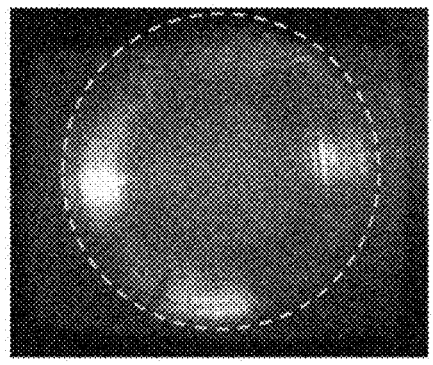
FIG. 8A illustrates an example of a captured image in a case where there is stray light.
Figure 8B:
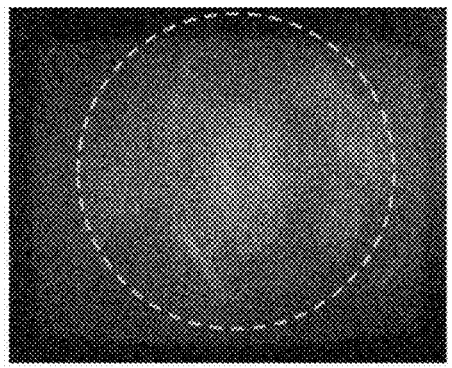
FIG. 8B illustrates an example of a captured image in a case where there is no stray light.

FIG. 8A illustrates an example of a captured image in a case where there is stray light. FIG. 8B illustrates an example of a captured image in a case where there is no stray light. If stray light occurs as illustrated in FIG. 8A, an annular blown out highlight occurs in a captured image due to stray light, and a clear image cannot be obtained. As illustrated in FIG. 8B, it is necessary to prevent the occurrence of stray light in the image unit while the endoscope 11 is used.

If an additive added to the molded part 65, as in the example illustrated in FIG. 7, light shielding performance improves by the extent of an increase in the amount of addition (the content) of the additive, and in contrast, the bonding strength of the molded part 65 decreases. Accordingly, it is necessary to add an adequate amount of the additive to the molded resin material according to the bonding strength characteristic of the additive.

Figure 9:
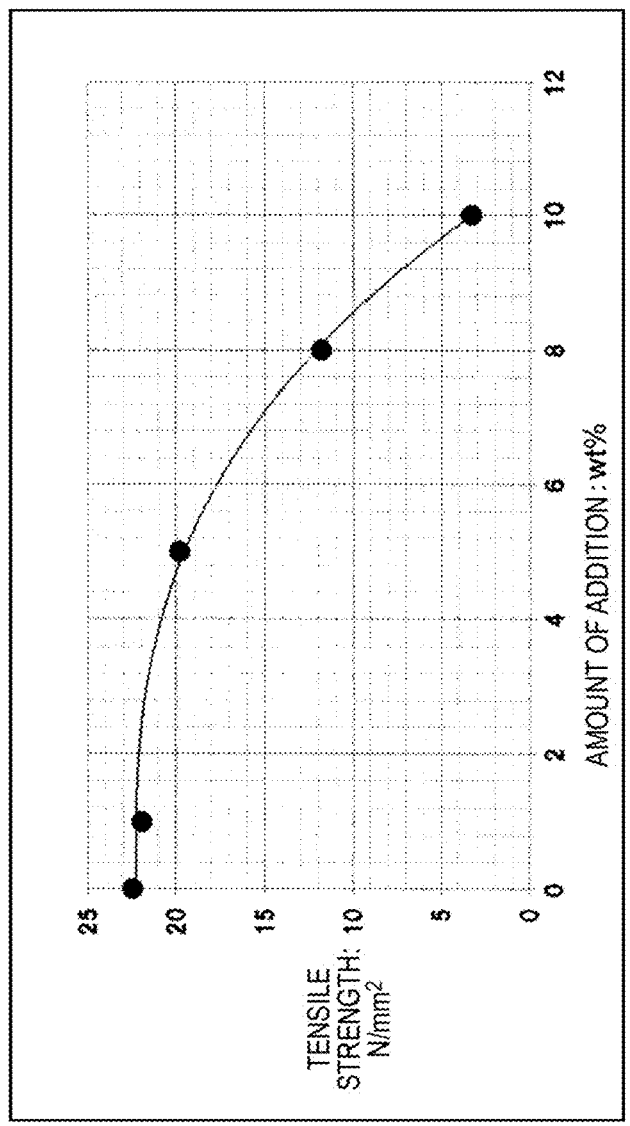
FIG. 9 is a characteristic graph illustrating an example of a relationship between the amount of addition of an additive to the molded part and the tensile strength of the molded part.

FIG. 9 is a characteristic graph illustrating an example of a relationship between the amount of addition of an additive to the molded part 65 and the tensile strength of the molded part 65. FIG. 9 illustrates an example of the measurement of tensile strength in a case where carbon black as an additive is added to a molded resin material (epoxy resin). The tensile strength corresponds to the bonding strength of the molded part 65. As illustrated in FIG. 9, if the amount of addition is 1% by weight, the tensile strength decreases by only approximately 2.5%. If the amount of addition is 5% by weight, the tensile strength decreases by approximately 12%. If the tensile strength decreases by approximately 20%, the bonding strength of the molded member may not be sufficient. For this reason, in a case where carbon black is added, the amount of addition of the carbon black is preferably set to 5% by weight or less.

If a conductive material such as carbon black is used as an additive, electric resistance decreases by the extent of an increase in the amount of addition, and conductivity is added.

FIG. 10 is a table illustrating an example of a relationship between the amount of addition of the additive to the molded part 65 and the resistance value and the light shielding coefficient of the molded part 65. FIG. 10 illustrates an example of the measurement of a resistance value and a light shielding coefficient in a case where carbon black as an additive is added to a molded resin material (epoxy resin). The resistance value and the light shielding coefficient were measured in three cases, that is, a case in which the amount of addition of carbon black is zero (0% by weight), a case in which the amount of addition of carbon black is 1% by weight, and a case in which the amount of addition of carbon black is 5% by weight. The light shielding coefficient of the molded part 65 having a thickness of 50 μm was measured. In a case where no carbon black is added, the resistance value is $1.8 \times 10^{13}$ to $5.0 \times 10^{13}$. In a case where 1% by weight carbon black is added, the resistance value is $2.5 \times 10^{13}$ to $3.0 \times 10^{13}$, and the light shielding coefficient is 95% or greater. In a case where 5% by weight carbon black is added, the resistance value is $3.5 \times 10^{10}$ to $5.0 \times 10^{10}$, and the light shielding coefficient is 99% or greater. The electric resistance value, in a case where 5% by weight carbon black is added, decreases by 1000 times that in a case where 1% by weight carbon black is added. For this reason, it is necessary to add an adequate amount of the additive to the molded resin material according to the conductive characteristic of the additive and the required insulation characteristic of an internal configuration element (electronic circuit or the like) which is a sealed target.

If the electric resistance of the molded part 65 is small, leakage current may occur in the conductor connection parts 49 connected to the image sensor 33 and in the transmission cable 31, and the electric characteristics of the periphery of a signal processing unit of the image unit may deteriorate. In contrast, in a case where static electricity occur in the image unit, it is possible to reduce the impact of electrostatic discharge, to prevent the flowing of excessive current to the image sensor 33, and to prevent the electrostatic destruction of the image sensor 33 by imparting adequate conductivity to the molded part 65. That is, the imparting of adequate conductivity to the molded part 65 can be a countermeasure against a surge of the image unit.

As described above, in the endoscope 11 of the seventh configuration example, since the resin material (the molded resin 17) of the molded part 65 contains an additive, it is possible to set the light transmittance of the molded part 65 to 10% or less, and it is possible to reduce the thickness of the molded part 65. As a result, the image unit of the endoscope 11 is capable of having a satisfactory light shielding characteristic, and it is possible to reduce the size of the image unit.

<Eighth Configuration Example>

As illustrated in FIG. 3, the endoscope 11 of the eighth configuration example in the embodiment includes the lens unit 35 in which lenses are accommodated in the lens support member 39; the image sensor 33, the imaging area 41 of which is covered with the sensor cover glass 43; the bonding resin 37 with which the lens unit 35 is fixed to the sensor cover glass 43 in a state where the optical axes of the lenses coincide with the center of the imaging area 41; the distal portion 15, the maximum outer diameter Dmax of which is set to a range from 1.8 mm to a finite diameter equivalent to the diameter of the circumscribed circle of the substrate of the image sensor 33 which can be obtained via dicing; the molded part 65 in which at least a portion of the lens unit 35 and the image sensor 33 are coated with and are fixed by the molded resin 17; and a tubular sheath 61 that is formed to have the same outer diameter as that of the distal portion 15 and covers at least a portion of the molded part 65.

In the following description, the same reference signs are assigned to the same members or configuration elements, and description thereof will be simplified or omitted. The endoscope 11 (refer to FIG. 3) of the eighth configuration example will be described in comparison with the endoscope 11 (refer to FIG. 11) of the tenth configuration example.

The sheath 61 is made of a resin material having flexibility. For the purpose of imparting strength to the sheath 61, a single cable, multiple cables, a braided tensile strength cable may be provided on the inner circumferential side of the sheath 61. Examples of the tensile strength cable may include an aramid fiber such as a poly-p-phenylene terephthalamide fiber, a polyester fiber such as a polyarylate fiber, a polyparaphenylene benzobisoxazole fiber, a polyethylene terephthalate fiber, a nylon fiber, a thin tungsten cable, and a thin stainless steel cable.

Similar to the endoscope 11 (refer to FIG. 11) of the tenth configuration example which will be described later, in the endoscope 11 of the eighth configuration example, the entirety of the image sensor 33, at least an image sensor 33 side portion of the lens unit 35, a portion of the transmission cable 31, and a portion of the light guides 57 are coated with and are fixed by the molded resin 17. The meaning of "at least" also includes a case in which the entire outer circumference of the lens support member 39 is covered with the molded resin 17. The molded resin 17 covers the image sensor 33 and the lens unit 35, and continuously covers the separation part 47 therebetween. The distal portion 15 of the endoscope 11 of the eighth configuration example may involve a radiopaque marker. As a result, it is possible to easily confirm a distal end position of the endoscope 11 of the eighth configuration example in radioscopy.

Similar to the endoscope 11 (refer to FIG. 11) of the tenth configuration example which will be described later, the endoscope 11 of the eighth configuration example includes a distal flange portion 63 in the distal portion 15. For example, the distal flange portion 63 may be formed of stainless steel. The distal flange portion 63 is formed into a cylindrical shape in which a large-diameter portion larger than a distal side is continuous with a small-diameter portion. The large-diameter portion of the distal flange portion 63 has the maximum outer diameter Dmax (1.8 mm). Insertion holes (not illustrated) for the insertion of the four optical fibers 59 are provided in the large-diameter portion, and the optical fibers 59 are respectively inserted into the insertion holes. An insertion hole (not illustrated) for the insertion of the lens unit 35 is provided in the small-diameter portion, and the lens unit 35 is inserted into the insertion hole. The distal flange portion 63 coaxially holds the lens unit 35. A fiber holding hole 67 for holding a distal side of the optical fiber 59 is drilled in the large-diameter portion of the distal flange portion 63 such that the fiber holding hole 67 is positioned outward from the small-diameter portion. Four fiber holding holes 67 are provided equally spaced from each other in the circumferential direction. The distal side of the optical fiber 59 is inserted into the fiber holding hole 67, and the optical fiber 59 is drawn rearward along the small-diameter portion.

In the endoscope 11 of the eighth configuration example, when the optical fiber 59 is positioned rearward from the distal flange portion 63, the optical fiber 59 is disposed inside a cover tube 69 (refer to FIG. 3). The cover tube 69 is formed to have the same outer diameter as that of the distal flange portion 63. The cover tube 69 is formed of a material such as metal or resin. A distal end of the cover tube 69 is in contact with the large-diameter portion of the distal flange portion 63. The cover tube 69 has the total length such that at least a rear end of the cover tube 69 reaches the transmission cable 31. The inside of the cover tube 69 is filled with the molded resin 17. That is, in the endoscope 11 of the eighth configuration example, the molded part 65 is covered with the cover tube 69. The endoscope 11 of the tenth configuration example has the same configuration as that of the endoscope 11 of the first configuration example, apart from the fact that the cover tube 69 is omitted, and a distal end of the sheath 61 is in contact with and is bonded to a rear end of the distal flange portion 63 with a bonding agent (refer to FIG. 11).

The molded part 65, with which the cover tube 69 is filled, includes a small-diameter extension portion 71 (refer to FIG. 3) that extends rearward from the rear end of the cover tube 69. The small-diameter extension portion 71 is molded into a columnar shape, and the four optical fibers 59 are embedded in the small-diameter extension portion 71. The transmission cable 31 is embedded in the small-diameter extension portion 71 while being positioned inside the four optical fibers 59. An inner diameter side of the sheath 61 is fixed to an outer circumference of the small-diameter extension portion 71 with a bonding agent or the like. That is, in the endoscope 11 of the eighth configuration example illustrated in FIG. 3, the distal flange portion 63, the cover tube 69, and the sheath 61 are coaxially continuous with each other with the maximum outer diameter Dmax set to 1.8 mm. In the endoscope 11 of the tenth configuration example illustrated in FIG. 11, the distal flange portion 63 and the sheath 61 are coaxially continuous with each other while having the maximum outer diameter Dmax of 1.8 mm.

As described above, in the endoscopes 11 of the eighth configuration example and the tenth configuration example, since at least a portion of the lens unit 35, the image sensor 33, and a portion of the transmission cable 31 are coated with and are fixed by the molded resin 17, the number of interposed members required to fix the lens unit 35 to the image sensor 33 is small. Accordingly, it is possible to reduce the diameter of the distal portion 15 of the endoscope 11. Also, in a case where a further thinning of the distal portion 15 is attempted, it is possible to configure the distal portion 15 with the minimum dimensions. In addition, it is possible to reduce component costs. It is possible to realize the endoscope 11 capable of capturing an image of a very thin target lesion such as a blood vessel of a human body. As a result, it is possible to reduce the size and the cost of the endoscope 11.

The molded resin 17 is continuously molded over the image sensor 33 and the lens unit 35, thereby contributing to an increase in fixing strength between the image sensor 33 and the lens unit 35. The molded resin 17 increases the air tightness (that is, there are not many small gaps), the water tightness, and the light shielding properties of the separation part 47. The molded resin 17 also increases the light shielding properties when the optical fibers 59 for the light guides 57 are embedded.

Since the molded resin 17 is molded over the light guides 57, the light guides 57 act as a structural member in the distal portion 15 of the endoscope 11, and it is possible to improve connection strength between the soft portion 29 and the distal portion 15 in the thin endoscope 11. When the distal portion 15 is viewed from an insertion side outermost surface (refer to FIG. 6) of the distal flange portion 63, in the endoscope 11, a gap between the lens unit 35 and the insertion hole (not illustrated) (provided in the distal flange portion 63 in advance) for the lens unit 35 is filled with the bonding resin 37, and gaps between the optical fibers 59 and the four fiber holding holes 67, which are provided in the distal flange portion 63 in advance corresponding to the optical fibers 59 is filled with the bonding resin 37. For this reason, in the endoscope 11, there is no gap between the insertion hole or the fiber holding holes 67 and the members (that is, the lens support member 39 and the optical fibers 59). In the endoscope 11, the distal flange portion 63 is bonded to the cover tube 69, and the cover tube 69 is bonded to the sheath 61, or the distal flange portion 63 is bonded to the sheath 61 with the bonding resin 37, and there is no gap between the distal flange portion 63 and the cover tube 69, between the cover tube 69 and the sheath 61, and between the distal flange portion 63 and the sheath 61 respectively. As a result, when the endoscope 11 is sterilized (that is, is cleaned) after use in an examination or surgery, it is possible to reduce the amount of adherence of cleaning residuals such as unwanted liquid to the endoscope 11, and the endoscope 11 is capable of providing a high level of convenience from the perspective of sanitation when the endoscope 11 will be used in a next examination or surgery.

In the endoscope 533 in the related art disclosed in WO2013/146091, the axial line of the distal portion is offset from the optical axis of the lens unit 547. For this reason, a distance to a subject is likely to change according to the rotational angle of the distal portion, and it is difficult to stably obtain a good quality image. If the axial line of the distal portion is offset from the optical axis of the lens unit 547, the state of interference between a duct inner wall and the distal portion is changed according to the rotational angle of the distal portion, and particularly, when the endoscope 533 is put into a thin hole, operability deteriorates. In contrast, in the endoscope 11 of the eighth configuration example, the distal flange portion 63, the cover tube 69, and the sheath 61 are coaxially continuous with each other, and in the endoscope 11 of the tenth configuration example, the distal flange portion 63 and the sheath 61 are coaxially continuous with each other. As a result, it is possible to easily thin the endoscopes 11, to stably obtain a good quality image, and to improve ease of insertion.

<Ninth Configuration Example>

In the endoscope 11 of the ninth configuration example in the embodiment, the thickness of the sheath 61 can be set to a range from 0.1 mm to 0.3 mm. The thickness of the sheath 61 is the same as the step dimension of a stepped portion between the cover tube 69 and the small-diameter extension portion 71. The small-diameter extension portion 71 is a portion that protrudes toward an opposite side of the lens unit 35 with the image sensor 33 interposed between the small-diameter extension portion 71. That is, one transmission cable 31 is disposed at the center of the small-diameter extension portion 71, and the four optical fibers 59 are disposed outside the transmission cable 31. As a result, it is possible to easily reduce the diameter of the small-diameter extension portion 71 compared to a portion of the molded part 65 in which the image sensor 33 is embedded. That is, since the sheath 61 has the same outer diameter as that of the cover tube 69, the degree of freedom in designing the wall thickness of the sheath 61 improves.

As described above, in the endoscope 11 of the ninth configuration example, since the thickness of the sheath 61 can be set up to 0.3 mm, it is possible to easily increase the tensile strength of the sheath 61.

<Tenth Configuration Example>

Figure 11:
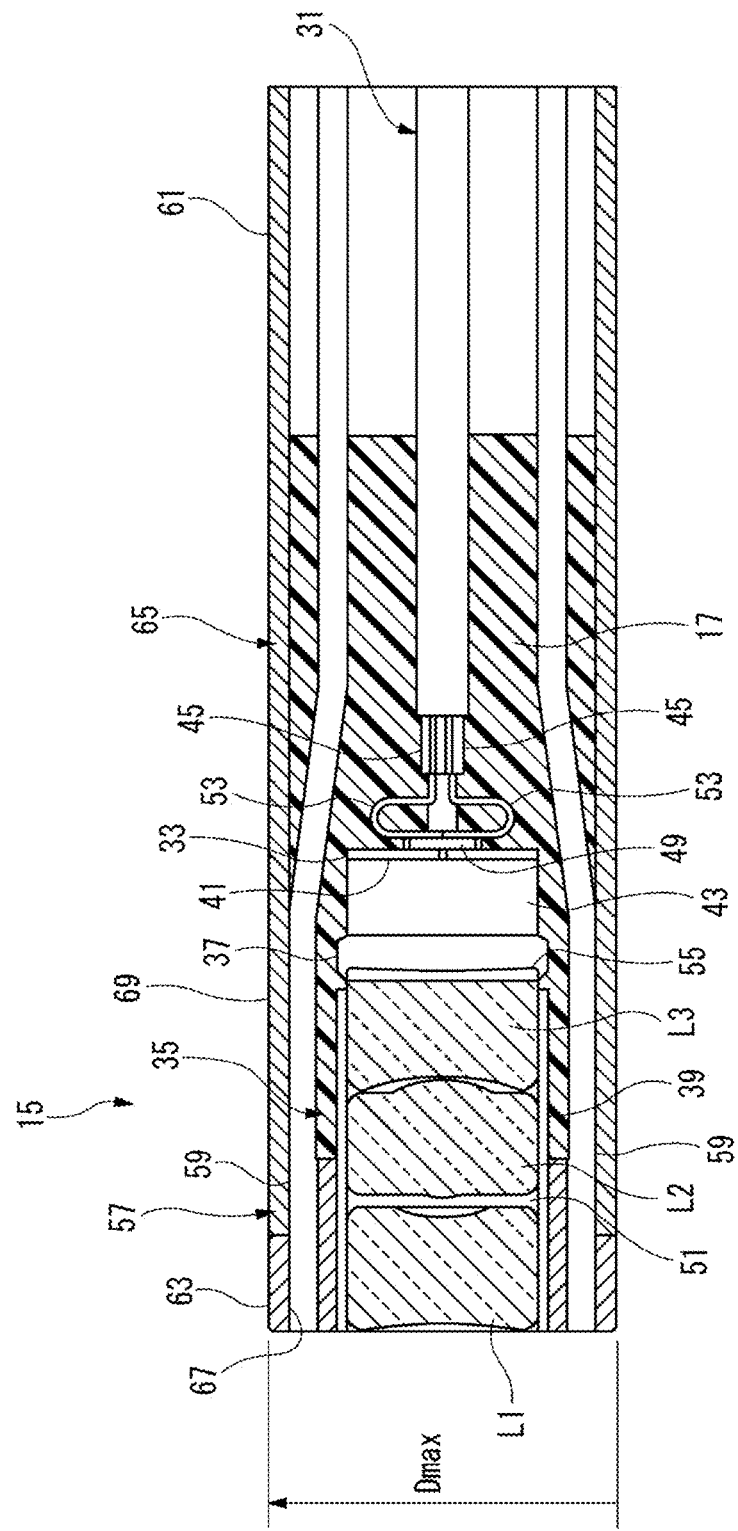
FIG. 11 is a sectional view illustrating an example of a configuration in which a thin wall sheath is connected to the distal portion.

FIG. 11 is a sectional view illustrating an example of a configuration in which a thin-wall sheath is connected to the distal portion.

In the endoscope 11 of the tenth configuration example in the embodiment, the thickness of the sheath 61 can be set to 0.1 mm. If the thickness of the sheath 61 is set to 0.1 mm, the endoscope 11 may not require the cover tube 69 described in the endoscope 11 of the eighth configuration example. That is, in the endoscope 11 of the tenth configuration example, the wall thickness of the sheath 61 is set to substantially the same wall thickness (0.1 mm) of the cover tube 69, and thus, the sheath 61 is capable of covering a portion of molded part 65 in which the image sensor 33 and the lens unit 35 are embedded. In the endoscope 11 of the tenth configuration example, the distal end of the sheath 61 is in contact with and is fixed to a rear end surface of the distal flange portion 63 with a bonding agent or the like. A decrease in the tensile strength of the sheath 61 caused by a thickness reduction can be made up for by providing the aforementioned tensile strength cable or the like in the sheath 61.

As described above, in the endoscope 11 of the tenth configuration example, since the cover tube 69 is omitted, and the sheath 61 can be in direct contact with the distal flange portion 63, it is possible to reduce the number of components.

<Eleventh Configuration Example>

Figure 12:
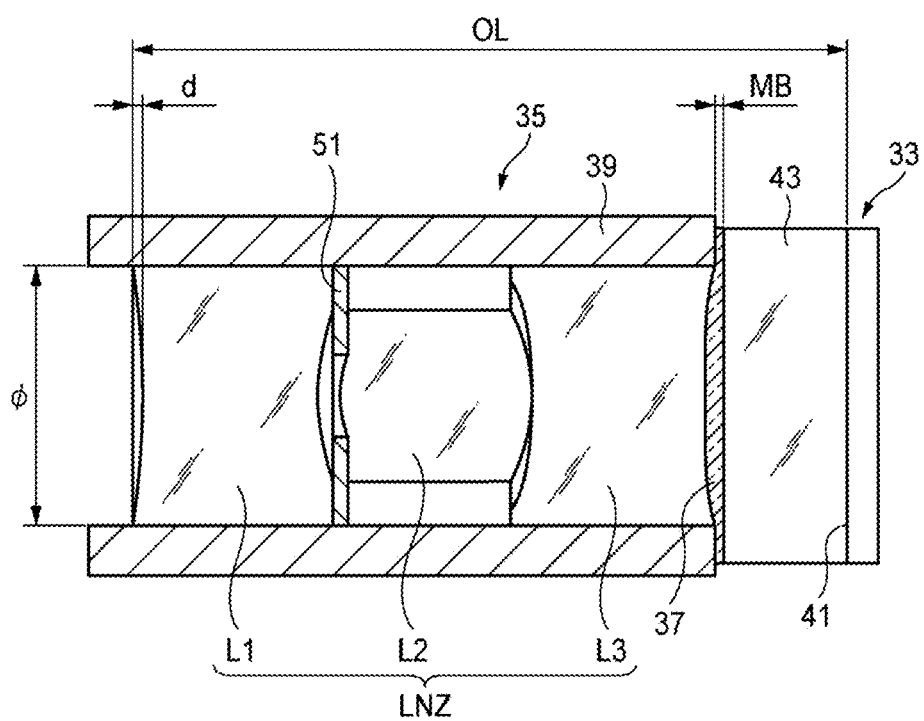
FIG. 12 is a sectional view illustrating an example of the configuration of an optical lens group of a lens unit.

FIG. 12 is a sectional view illustrating an example of the configuration of the optical lens group LNZ of the lens unit.

The endoscope 11 of the eleventh configuration example in the embodiment includes the lens unit 35 including the lens support member 39, a front group lens and a rear group lens which are accommodated in the lens support member 39, and the aperture stop 51 disposed between the front group lens and the rear group lens; the image sensor 33, the imaging area 41 of which is covered with the sensor cover glass 43; a bonding layer made of the bonding resin 37 with which an image side final surface of the rear group lens of the lens unit 35 is fixed to the sensor cover glass 43 of the image sensor 33; and the distal portion 15, the maximum outer diameter Dmax of which is set to a range from 1.8 mm to a finite diameter equivalent to the diameter of the circumscribed circle of the substrate of the image sensor 33 which can be obtained via dicing. The endoscope 11 of the eleventh configuration example has a structure in which the image side final surface of the rear group lens and an image side end surface of the lens support member 39 are fixed to the sensor cover glass 43 via the bonding layer made of the bonding resin 37. A focal length fF of the front group lens, a focal length fB of the rear group lens, a focal length fel of the entire optical system including the front group lens, the rear group lens, the bonding layer made of the bonding resin 37, and the sensor cover glass 43, a total optical length OL equivalent to a distance from a subject side foremost surface of the front group lens to an image side rear end surface of the sensor cover glass 43, and a metal back MB equivalent to a distance from the image side final surface of the rear group lens to a subject side front end surface of the sensor cover glass 43 are capable of satisfying relationships: fel/fF<0, fel/fB>0, and 7.0≤OL/MB≤1200.

In the lens unit 35, the first lens L1 acts as the front group lens, and the second lens L2 and the third lens L3 act as the rear group lens. The first lens L1 is a leading lens of the optical lens group LNZ, and the third lens L3 is a final lens of the optical lens group LNZ. In the lens unit 35, a first surface (foremost surface) L1R1 and a second surface L1R2 of the first lens L1 are concave surfaces, a first surface L2R1 and a second surface L2R2 of the second lens L2 are convex surfaces, and a first surface L3R1 and a second surface L3R2 (final surface) of the third lens L3 are concave surfaces, which are disposed sequentially from a subject side toward an image side.

The aperture stop 51 is provided between the first lens L1 and the second lens L2, that is, between the front group lens and the rear group lens. A gap between the second surface (final surface) (concave surface) L3R2 of third lens L3 and the sensor cover glass 43 of the image sensor 33 is filled with the bonding resin 37, and a bonding layer is formed therebetween.

FIG. 13 is a table illustrating lens data which indicates the optical characteristics of the lens unit illustrated in FIG. 12. In FIG. 13, surfaces respectively correspond to the surfaces L1R1 to L3R2 of the first lens L1 to the third lens L3, the aperture stop 51, and the bonding layer (bonding resin 37), and the radius of curvature (mm), the conic coefficient, and the effective diameter (mm) of each surface are illustrated. The thickness (mm) represents a distance (thickness) between the optical centers of the corresponding surface and the following surface in the direction of the optical axis. The refractive index and the Abbe number represents the refractive index and the Abbe number of an optical member that forms the corresponding surface. The outer diameter (outer diameters of the first lens L1 and the third lens L3) φ of the optical lens group LNZ is approximately 0.9 mm to approximately 1.0 mm. The sensor cover glass 43 of the image sensor 33 has a thickness of 0.4 mm.

The focal length fel of the entire optical lens group LNZ is 0.58 mm. The focal length fF of the front group lens (first lens L1) is −0.714. The focal length fB of the rear group lens (second lens L2 and third lens L3) is 0.481. If the total optical length OL of the optical lens group LNZ is assumed to be a length from the foremost surface (first surface L1R1 of the first lens L1) of the leading lens to the imaging area (image side rear end surface of the sensor cover glass 43 of the image sensor 33), the total optical length OL is 2.287 mm.

If the metal back MB is assumed to be a length from a peripheral portion end surface of the final surface (second surface L3R2 of the third lens L3) to the subject side front end surface of the sensor cover glass 43 of the image sensor 33, the metal back MB is 0.04 mm. The metal back MB may also be referred to as a back focus which indicates the roughness of the final surface of the final lens. The metal back MB is used as a parameter containing the back focus BF, and the metal back MB is collectively described. As illustrated in FIG. 13, the thickness of the bonding layer at the optical center is 0.05 mm, and in contrast, the second surface L3R2 of the third lens L3 is a concave surface. Accordingly, the metal back MB equivalent to the length from the peripheral portion end surface of the second surface L3R2 to the front end surface of the sensor cover glass 43 is shorter than the thickness at the optical center.

fel/fF is −0.812, fel/fB is 1.206, and OL/MB is 38.12.

Relationships, that is, fel/fF<0, fel/fB>0, and 7.0≤OL/MB, are satisfied.

The range of MB is 0.005 mm or greater and 0.250 mm or less.

The range of OL is 2.000 mm or greater and 6.000 mm or less.

Accordingly, 8.0≤OL/BF≤1200 is obtained. If 7.0≤OL/MB is combined with this relationship, 7.0≤OL/BF≤1200 is obtained. The maximum MB is a numeral based on MB=0.005 mm in underwater near point observation, and the minimum MB is a numeral based on MB=0.190 mm in aerial remote point observation.

More specifically, examples of aerial long-range observation include the trachea and the laryngeal part. Examples of aerial short-range observation include a segmental bronchus and a bronchiole. Examples of underwater long-range observation include the inside of the uterus and the stomach. Examples of underwater short-range observation include the bladder, the inside of a coronary artery, a knee joint, and the hip joint.

As described above, the endoscope 11 of the eleventh configuration example can be used for a human blood vessel, it is possible to reduce the metal back MB with respect to the total optical length OL, and it is possible to realize a structure in which the lens unit 35 is directly bonded to and is fixed to the sensor cover glass 43 of the image sensor 33 via the bonding layer. It is possible to obtain a high-strength structure of the image unit which includes a small number of components, it is possible to realize a short focal length of an image lens, and it is possible to reduce the length and the size of the image lens. As a result, it is possible to reduce the size and the cost of the endoscope 11.

<Twelfth Configuration Example>

Similar to the endoscope 11 of the eleventh configuration example, in the endoscope 11 of the twelfth configuration example, the image side final surface of the rear group lens is a curved surface. A refractive index nbe of the image side final lens of the rear group lens is not the same as a refractive index nad of the bonding layer in a case where the rear group lens is fixed via the bonding layer.

As described above, in the endoscope 11 of the twelfth configuration example, since the final surface of the rear group lens is capable of having refractive power by forming the image side final surface of the rear group lens into a curved surface, it is possible to increase the convergence of light beams from a subject which pass through the lens unit 35. As a result, it is possible to reduce an aberration of the lens unit 35, and to improve a resolution. If the image side final surface of the rear group lens is formed into a concave surface, since it is possible to increase the height of an image of a subject in the imaging area 41, it is possible to further reduce the diameters of the lenses.

<Thirteenth Configuration Example>

In the endoscope 11 of the thirteenth configuration example, an Abbe number $\nu$be of the image side final lens of the rear group lens is set to be greater than 25, and the refractive index nbe of the image side final lens of the rear group lens is greater than 1.40 and less than 1.90 in comparison with those in the endoscope 11 of the eleventh configuration example.

As described above, in the endoscope 11 of the thirteenth configuration example, since the Abbe number $\nu$be of the image side final lens of the rear group lens is set to be greater than 25, and the refractive index nbe of the image side final lens of the rear group lens is greater than 1.40 and less than 1.90, it is possible to reduce the chromatic aberration of magnification of the lens unit 35, and it is possible to set the chromatic aberration of magnification to be smaller than the pixel pitch of the image sensor 33. As a result, it is possible to reduce color bleeding in a peripheral portion of a captured image.

<Fourteenth Configuration Example>

Similar to the endoscope 11 of the eleventh configuration example, in the endoscope 11 of the fourteenth configuration example, the subject side foremost surface of the front group lens is a concave surface or convex surface, and the amount of sag d of the concave surface or convex surface and the lens outer diameter $\phi$ of the optical lens group including the front group lens and the rear group lens satisfy a relationship, that is, $-0.1 < d/\phi < 0.1$.

As described above, in the endoscope 11 of the fourteenth configuration example, since the subject side foremost surface of the front group lens is a concave surface or convex surface, and the amount of sag d of the concave surface or convex surface and the lens outer diameter $\phi$ of the optical lens group including the front group lens and the rear group lens satisfy the relationship, that is, $-0.1 < d/\phi < 0.1$, it is possible to shape the foremost surface of the lens unit 35 close to a flat surface, and to reduce the amount of adherence of impurity to the endoscope in use. If the subject side foremost surface of the front group lens is formed into a concave surface, since it is possible to increase the viewing angle (angle of view) of the lens unit 35, it is possible to widen the visual field of a subject, and to further reduce the diameters of the lenses.

<Fifteenth Configuration Example>

The endoscope 11 of the fifteenth configuration example in the embodiment includes the lens unit 35 in which the front group lens and the rear group lens are accommodated in the lens support member 39, and the aperture stop 51 is disposed between the front group lens and the rear group lens; the image sensor 33, the imaging area 41 of which is covered with the sensor cover glass 43; the bonding resin 37 with which the lens unit 35 is fixed to the sensor cover glass 43 in a state where the optical axes of the lenses coincide with the center of the imaging area 41; and a rough surface portion 73 (refer to FIG. 4) that is formed in an outer circumferential surface of the rear group lens and prevents the outer circumferential surface from totally reflecting light propagating through the rear group lens.

Figure 14:
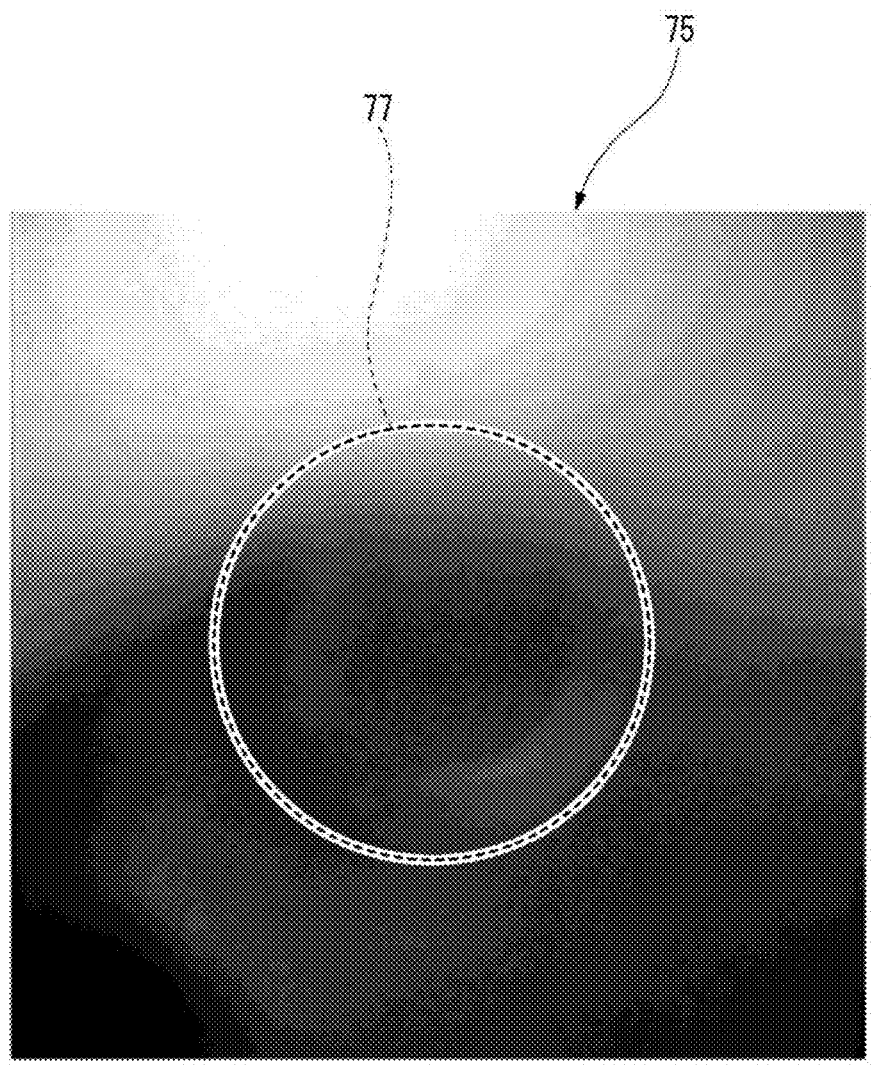
FIG. 14 illustrates an example of a captured image based on an actual measurement result on which ring-shaped stray light appears.

FIG. 14 illustrates an example of a captured image based on an actual measurement result on which ring-shaped stray light appears. FIG. 14 is a captured image 75 that is obtained by a proto endoscope corresponding to the endoscope illustrated in FIG. 4 which is inserted into the bronchus of an animal.

In a result of an actual measurement performed by the endoscope 11 of the fifteenth configuration example, it was confirmed that ring-shaped stray light 77 appeared in the captured image 75. In the process of development of the endoscope 11, it was confirmed that stray light occurred in a case where the number of lenses accommodated in the lens unit was changed from a four-lens configuration (not illustrated) to a three-lens configuration (not illustrated). It was confirmed that the output level of stray light became more prominent (that is, a captured image became blurred) (refer to FIG. 14) in a case where a three-lens configuration was changed to a direct-attached three-lens configuration (refer to FIG. 4) in which the final lens is directly attached to the sensor cover glass 43 of the image sensor 33.

Figure 15:
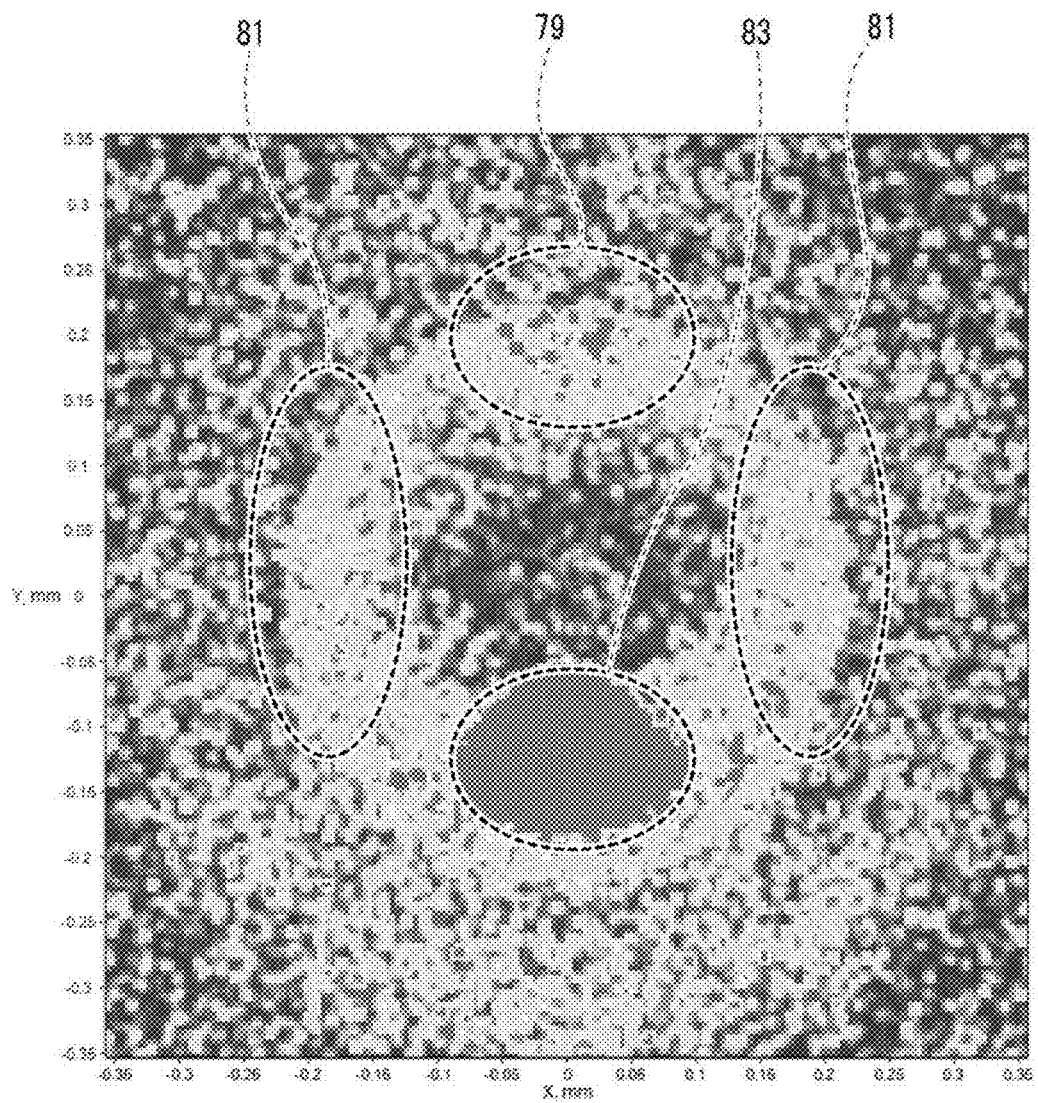
FIG. 15 is a measurement image obtained via simulation, which is a captured image in which multiple beams of stray light appear.

FIG. 15 is a measurement image obtained via simulation, which is a captured image in which multiple beams of stray light appear. According to simulation, it was confirmed that among beams of scattered ring-shaped stray light, ring-shaped upper stray light 79, beams of ring-shaped both side stray light 81, and ring-shaped lower stray light 83 prominently appeared.

Figure 16A:
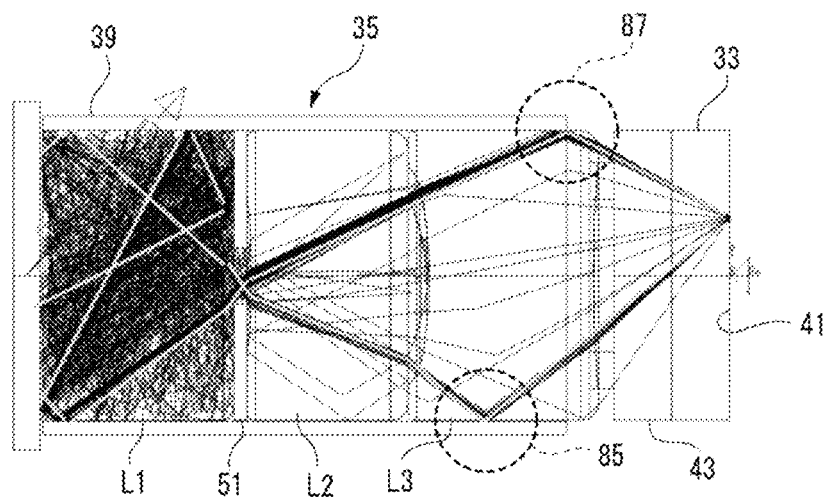
FIG. 16A is a light beam trace diagram of upper stray light among beams of scattered ring-shaped stray light.
Figure 16B:
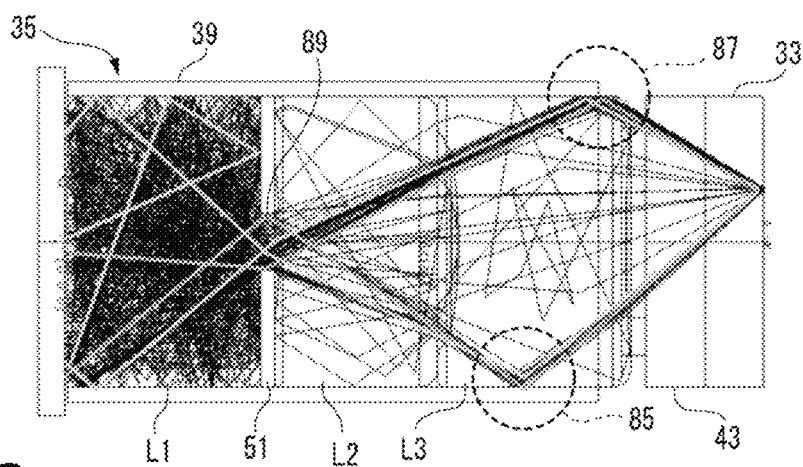
FIG. 16B is a light beam trace diagram of beams of both side stray light among the beams of scattered ring-shaped stray light.
Figure 16C:
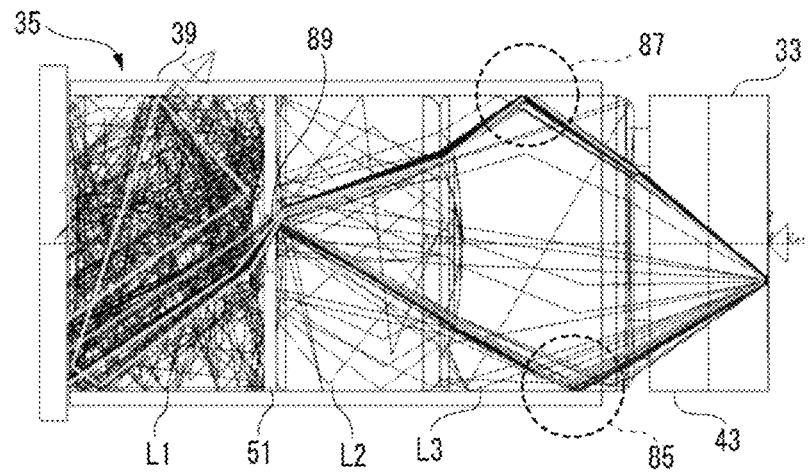
FIG. 16C is a light beam trace diagram of lower stray light among the beams of scattered ring-shaped stray light.

FIG. 16A is a light beam trace diagram of upper stray light among beams of scattered ring-shaped stray light. FIG. 16B is a light beam trace diagram of beams of both side stray light among the beams of scattered ring-shaped stray light. FIG. 16C is a light beam trace diagram of lower stray light among the beams of scattered ring-shaped stray light.

As a result of performing light beam tracing via simulation, as illustrated in FIG. 16A, the upper stray light 79 was prominently affected by reflection of light from a portion 85 of the outer circumferential surface of the lens L3 and reflection of light from a portion 87 of the lens L3 which projected from the lens support member 39.

As a result of performing light beam tracing via simulation, as illustrated in FIG. 16B, the beams of both side stray light 81 were prominently affected by reflection of light from an inner diameter edge 89 of the aperture stop 51, reflection of light from the portion 85 of the outer circumferential surface of the lens L3, and reflection of light from the portion 87 of the lens L3 which projected from the lens support member 39.

As a result of performing light beam tracing via simulation, as illustrated in FIG. 16C, the lower stray light 83 was prominently affected by reflection of light from the inner diameter edge 89 of the aperture stop 51 and reflection of light from the portion 85 of the outer circumferential surface of the lens L3.

According to the simulation illustrated in FIGS. 16A to 16C, almost all light forming stray light is incident to the imaging area 41 of the image sensor 33 by reflection of light from the portion 85 of the outer circumferential surface of the lens L3 and reflection of light from the portion 87 of the lens L3 which projected from the lens support member 39. It was verified that beams of scattered stray light were considerably affected by reflection of light from the portion 85 of the outer circumferential surface of the lens L3 and reflection of light from the portion 87 of the lens L3 which projected from the lens support member 39 (light, which was reflected from the portion 87 of the lens L3 which projected from the lens support member 39, passed through the edge portion 55 which was an annular end surface on the circumference of the lens L3).

The outer circumferential surface of the lens L3 of the proto endoscope was frost-glassed. That is, the rough surface portion 73 (refer to FIG. 4) was provided so as to prevent the outer circumferential surface from totally reflecting light propagating through the rear group lens (lens L3).

FIGS. 17A and 17B show measurement images obtained via illuminance distribution simulation which illustrates whether or not stray light is eliminated by providing the rough surface portion. FIGS. 18A and 18B illustrate an example of captured images of an actual measurement result in which stray light is reduced by providing the rough surface portion.

In the endoscope 11 of the fifteenth configuration example, since the outer circumferential surface of the lens L3 is frost-glassed, light reflected from the portion 85 of the outer circumferential surface of the lens L3 is reduced by a scattering effect of the rough surface portion (frosted glass surface) 73. In the simulation illustrated in FIGS. 17A and 17B and the actual measurement result illustrated in FIGS. 18A and 18B, almost all of the upper stray light 79, the beams of both side stray light 81, and the lower stray light 83 were reduced and eliminated.

As described above, in the endoscope 11 of the fifteenth configuration example, since the rough surface portion 73 is provided on the outer circumferential surface of the lens L3, it is possible to eliminate almost all beams of scattered ring-shaped stray light without adding a separate light shielding member (black painted cylindrical body or the like) on the outer circumference of the lens L3. As a result, it is possible to reduce the size and the cost of the endoscope 11 while preventing the occurrence of stray light.

<Sixteenth Configuration Example>

In the endoscope 11 of the sixteenth configuration example, the surface roughness of the rough surface portion 73 is preferably set to a range of an arithmetic average roughness Ra from 0.1 μm to 10 μm in comparison with the configuration of the endoscope 11 of the fifteenth configuration example. The rough surface portion 73 can be obtained by grinding the outer circumferential surface of the lens L3 with abrasive grains. It was ascertained that if the roughness Ra was 0.1 μm or less, the rough surface portion 73 was close to a mirror surface, and strength of reflected light tended to gradually increase. It was ascertained that if the roughness Ra of the rough surface portion 73 was 10 μm or greater, the ratio of a rough surface to a reflecting surface decreased, and thus, strength of reflected light tended to gradually increase.

As described above, in the endoscope 11 of the sixteenth configuration example, it is possible to prevent the occurrence of stray light without a cost increase by imparting the optimum roughness to the lens L3 without the use of other members.

<Seventeenth Configuration Example>

In the endoscope 11 of the seventeenth configuration example, the rough surface portion 73 may be formed in an end surface (the edge portion 55) surrounding an image light emitting effective surface of the image side final surface of the rear group lens (lens L3) in comparison with the configuration of the endoscope 11 of the sixteenth configuration example. Since the rough surface portion 73 is provided on the outer circumferential surface of the lens L3, it is possible to prevent the occurrence of stray light in the endoscope 11. In addition, since the rough surface portion 73 is also provided in the edge portion 55, in the endoscope 11, it is possible to further prevent the occurrence of the upper stray light 79, the beams of both side stray light 81, and the lower stray light 83 which cannot be completely scattered by the portion 85 of the outer circumferential surface of the lens L3 and the portion 87 of the lens L3 which projects from the lens support member 39.

As described above, in the endoscope of the seventeenth configuration example, it is possible to further prevent the occurrence of stray light by providing the rough surface portion 73 in the edge portion 55 of the lens L3 without using other members.

(Second Embodiment)

Hereinafter, the endoscope 111 of a second embodiment will be described.

Figure 19:
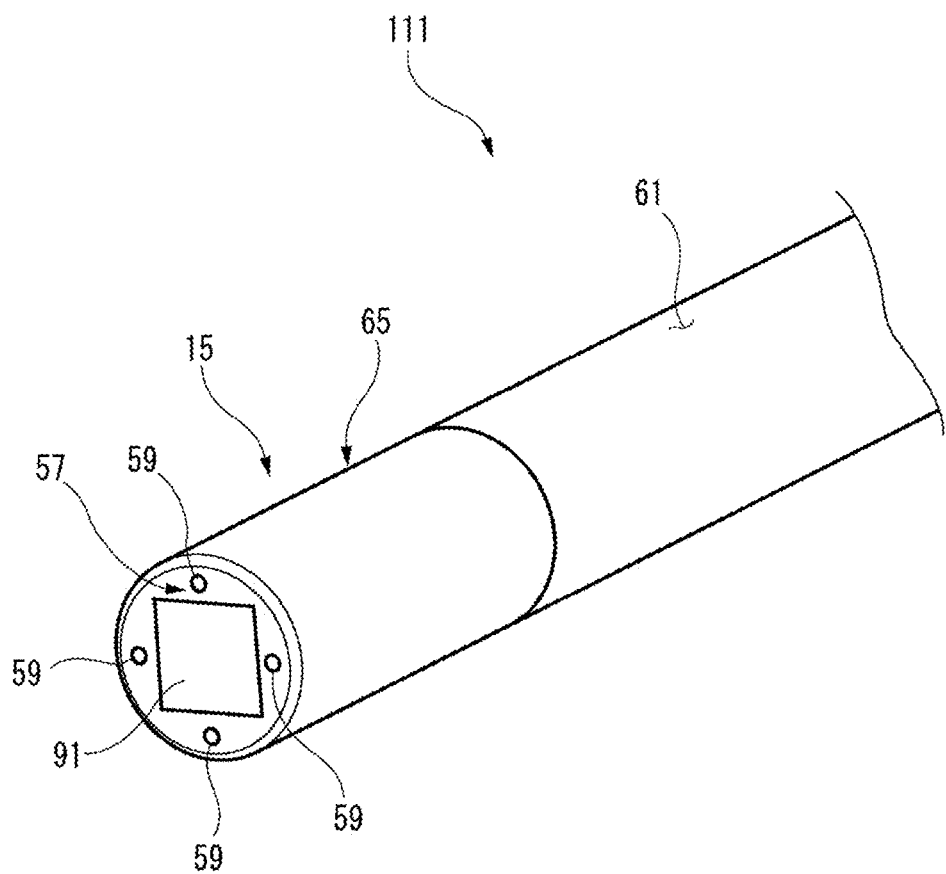
FIG. 19 is a perspective view of the distal portion of an endoscope of a second embodiment which is viewed from the front side.
Figure 20:
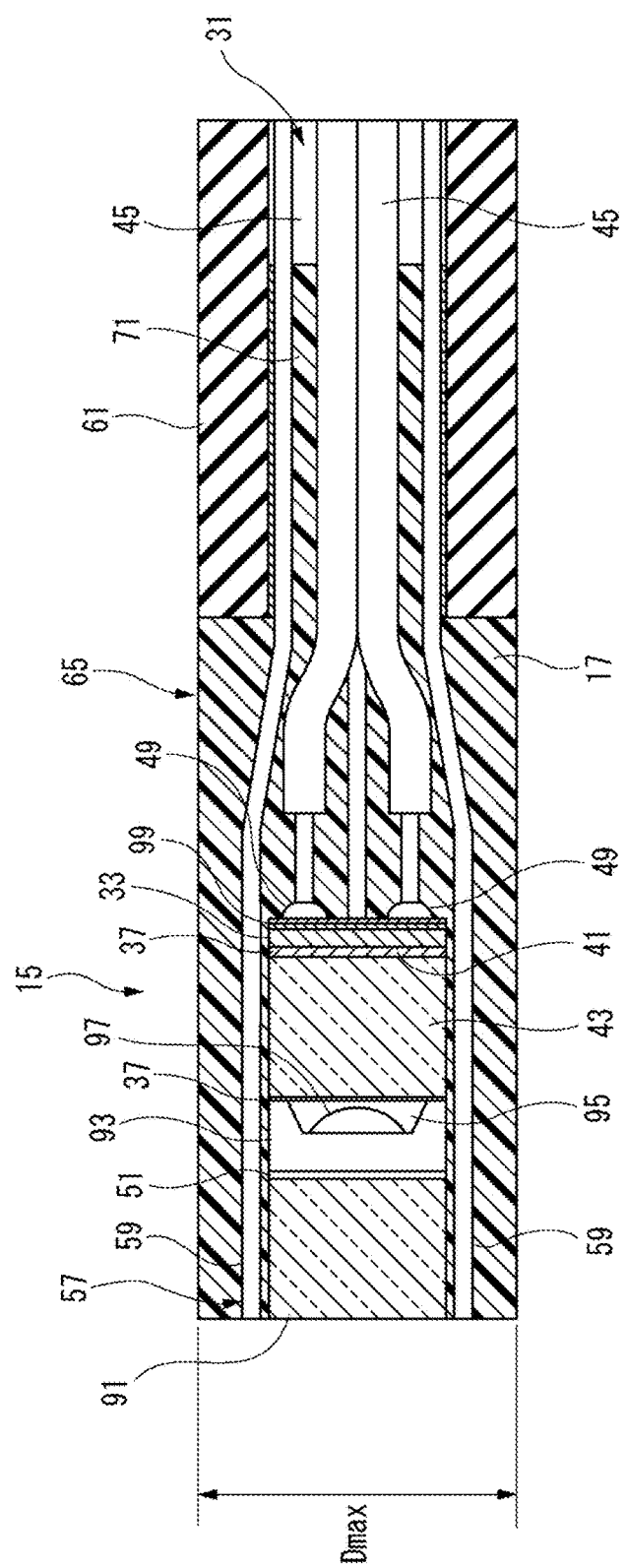
FIG. 20 is a sectional view illustrating an example of the distal portion of the endoscope of the second embodiment.
Figure 21:
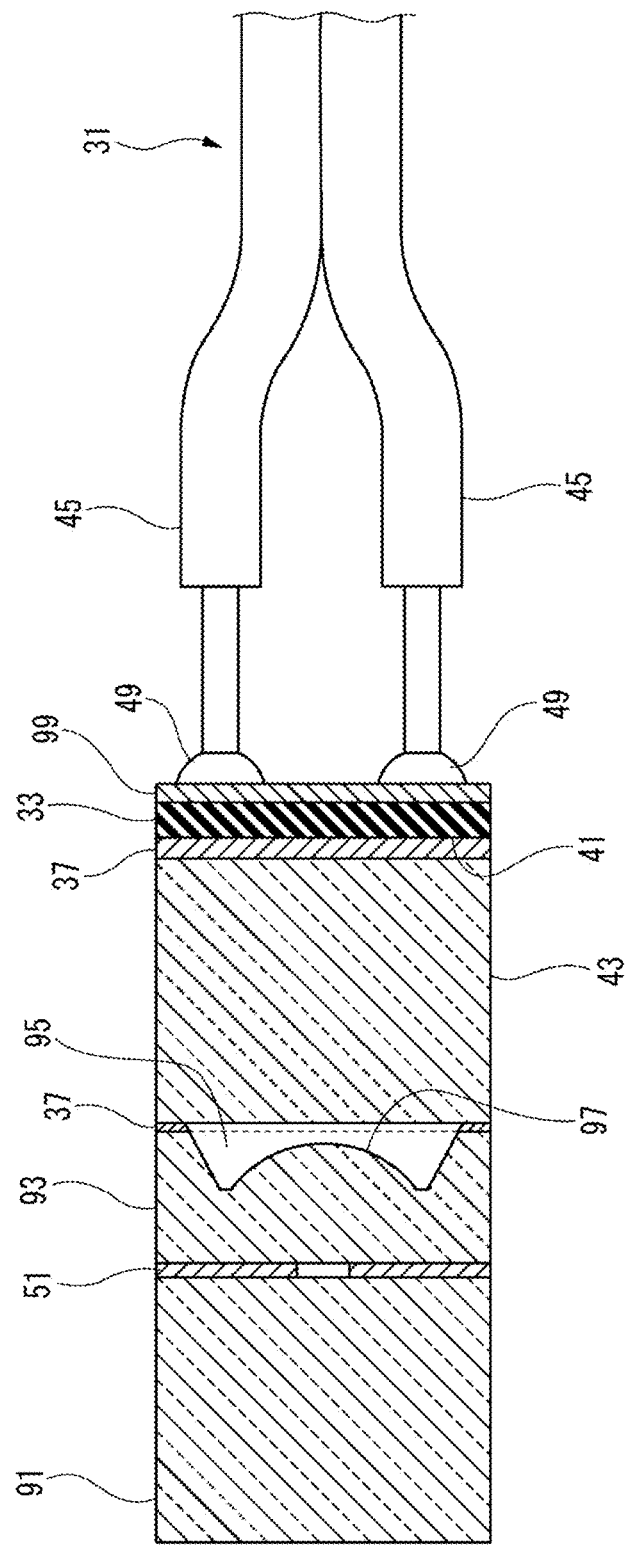
FIG. 21 is a sectional view illustrating an example of a state in which the lenses are directly attached to the image sensor via bonding resin in the endoscope of the second embodiment.
Figure 22:
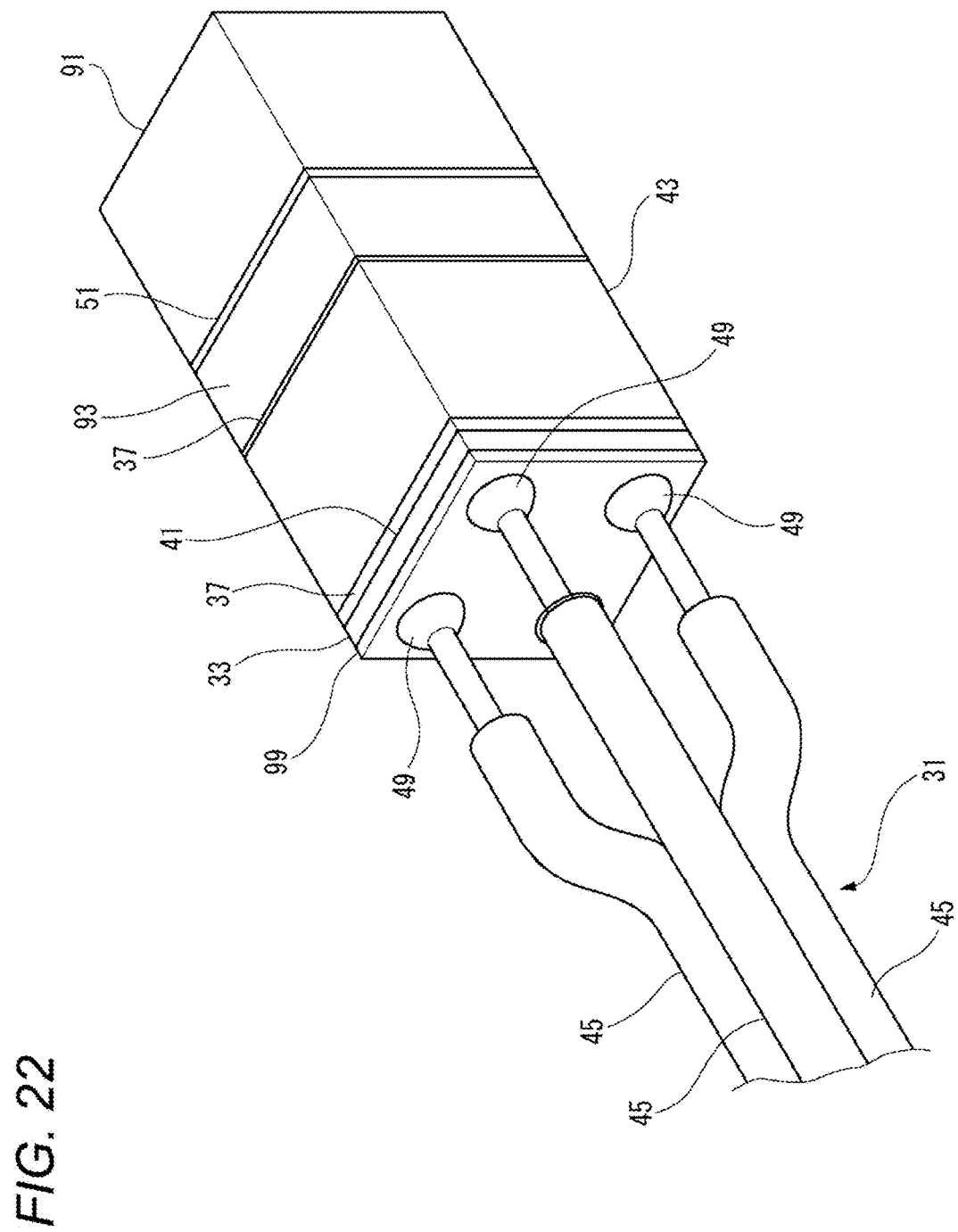
FIG. 22 is a perspective view of the image sensor which is viewed from the rear side, which illustrates a state in which the transmission cable is connected to the conductor connection part of the endoscope of the second embodiment.

FIG. 19 is a perspective view of the distal portion of the endoscope 111 of the second embodiment which is viewed from the front side. FIG. 20 is a sectional view illustrating an example of the distal portion of the endoscope 111 of the second embodiment. FIG. 21 is a sectional view illustrating an example of a state in which the lenses are directly attached to the image sensor via the bonding resin in the endoscope of the second embodiment. FIG. 22 is a perspective view of a side of the image sensor which is opposite to the lens unit, which illustrates a state in which the transmission cable is connected to the conductor connection part of the endoscope of the second embodiment. In the second embodiment, the same reference signs are assigned to the same members as those in the first embodiment, and duplicated description will be omitted.

<Eighteenth Configuration Example>

In the endoscope 111 illustrated in FIG. 19, the maximum outer diameter Dmax of the distal portion 15 illustrated in FIG. 20 may be set to a range from 1.0 mm to a finite diameter equivalent to the diameter of the circumscribed circle of the substrate of the image sensor 33 which can be obtained via dicing.

In the endoscope 111 of the embodiment, an image sensor, one side of which has a dimension of 0.5 mm is used as the image sensor 33 having a square section in the direction perpendicular to the optical axis. As a result, the image sensor 33 has a diagonal dimension of approximately 0.7 mm, and the maximum outer diameter Dmax of the endoscope 111 including the light guide 57 (for example, having 50 microns ϕ) as an illuminator may be set to 1.0 mm or less.

As described above, since the maximum outer diameter Dmax is set to less than 1.0 mm, the endoscope 111 of the eighteenth configuration example can be more easily inserted into a blood vessel of a human body.

<Nineteenth Configuration Example>

In the endoscope 111 of the nineteenth configuration example in the embodiment, as illustrated in FIG. 22, the substrate of the image sensor 33 is formed into a square shape, and the conductor connection parts 49 are disposed at four corners of the substrate of the image sensor 33. Each one of the conductor connection parts 49 is formed into a circular shape. Since the four conductor connection parts 49 are disposed at the four corners of the square shape, the four conductor connection parts 49 can be disposed while spaced the maximum distance from each other.

A conductor of each of the electric power cables and the signal cables, which are the electric cables 45 of the transmission cable 31, is covered with an insulation coating. One transmission cable 31 is formed by disposing two sets of the four electric cables 45 on the right and left sides and in two stages in the upward and downward direction, and binding outer circumferences of the insulation coatings with an outer cover. In a state where the insulation coatings are peeled from four conductors, the four conductors are formed straight while being parallel to each other. A distal end of the conductor of the electric cable 45 is connected to the conductor connection part 49 via soldering. As illustrated in FIG. 20, the image sensor 33 and the transmission cable 31 are covered with the molded resin 17. As a result, the conductor connection parts 49, the conductors, the insulation coatings of the electric cables 45, and the outer cover of the transmission cable 31 are embedded in the molded resin 17.

As described above, in the endoscope 111 of the nineteenth configuration example, since the four conductor connection parts 49 can be disposed at the four corners of the substrate of the image sensor 33, as illustrated in FIG. 22, the four conductor connection parts 49 can be disposed on the substrate of the square image sensor 33 while spaced equally and the maximum distance from each other. Accordingly, it is possible to easily ensure an insulation distance without causing adjacent two conductor connection parts 49 to be connected to each other via soldering in a soldering step. As a result, it is possible to easily thin the distal portion 15. As illustrated in FIG. 22, the four conductor connection parts 49 may be disposed at the four corners of the substrate of the image sensor 33 in the endoscope 11 of the first embodiment.

<Twentieth Configuration Example>

As illustrated in FIG. 21, the endoscope 111 of the twentieth configuration example includes objective cover glass 91; the sensor cover glass 43; the image sensor 33, the imaging area 41 of which is covered with the sensor cover glass 43; a lens 93 which is interposed between the objective cover glass 91 and the sensor cover glass 43, and the optical axis of which coincides with the center of the imaging area 41; the aperture stop 51 interposed between the objective cover glass 91 and the lens 93; the bonding resin 37 with which the lens 93 is fixed to the sensor cover glass 43; and an air layer 95 provided between the lens 93 and the sensor cover glass 43.

In the endoscope 11 of the first embodiment, the bonding resin 37 is applied to the separation part 47 having a finite width between the final lens L3 of three lenses and the sensor cover glass 43, and thus, the lens L3 is directly attached to the sensor cover glass 43. In contrast, in the endoscope 111 of the second embodiment, the lens 93 is directly attached to the sensor cover glass 43 via the bonding resin 37. As a result, in the endoscope 111, the bonding resin 37 has substantially a line shape in a side view (refer to FIG. 22). In the endoscope 111 of the second embodiment, both end side edge portions of the lens 93 are directly attached to the sensor cover glass 43 with the bonding resin 37. The bonding resin 37 is applied to only the edge portions.

The lens 93 is a single lens, has the same square columnar exterior shape as that of the image sensor 33, and has a square section in the direction perpendicular to the optical axis. Light, which is incident from a subject and passes through the objective cover glass 91, is imaged on the imaging area 41 of the image sensor 33 via the sensor cover glass 43 by the lens 93. A recessed portion is formed in a sensor cover glass 43 side surface of the lens 93. A convex curved surface portion 97 is formed on a bottom surface of the recessed portion in such a way as to protrude and form a substantially spherical surface. Owing to the convex curved surface portion 97, the lens 93 acts as an optical sensor that converges light. A protrusion distal end of the convex curved surface portion 97 is slightly spaced from the sensor cover glass 43. In contrast, a rectangular annular end surface of the lens 93 surrounding the recessed portion is bonded to the sensor cover glass 43 via the bonding resin 37. Accordingly, air is sealed in the recessed portion between the lens 93 and the sensor cover glass 43. Air sealed in the recessed portion, which becomes a sealed space, preferably is dry air. Nitrogen may be sealed in the recessed portion. As such, the air layer 95 having the recessed portion as an inner volume is formed between the lens 93 and the sensor cover glass 43. The convex curved surface portion 97 is disposed in the air layer 95. That is, a light emitting surface of the convex curved surface portion 97 of the lens 93 is in contact with air.

An important factor in the thinning of the endoscope 111 having the maximum outer diameter Dmax of 1.0 mm is whether the number of lenses is reduced. Accordingly, in a case where the lens 93 is provided as a single lens in the endoscope 111, the magnitude of a refractive index difference between the lens 93 and a very small area, which is positioned in a width direction parallel to the direction of the optical axis, is important. In the endoscope 111 of the twentieth configuration example, an air layer is provided on an optical sensor surface such that a large refractive index difference between the lens 93 and the air layer can be obtained.

As described above, in the endoscope 111 of the twentieth configuration example, since the recessed portion is formed in the lens 93, the convex curved surface portion 97 is formed on the bottom surface of the recessed portion, and the rectangular annular end surface is bonded to the sensor cover glass 43, the air layer 95 for increasing a refractive index difference with respect to the lens 93 can be ensured in a very small area. At the same time, it is possible to easily align the optical axis of the lens 93 with respect to the imaging area 41. Since it is possible to ensure the air layer 95, it is possible to obtain a large lens power between the lens 93 and the air layer 95. Accordingly, it is possible to reduce the number of lenses to one in the endoscope 111. As a result, it is possible to reduce the size and the cost of the endoscope 111.

<Twenty-first Configuration Example>

Figure 23:
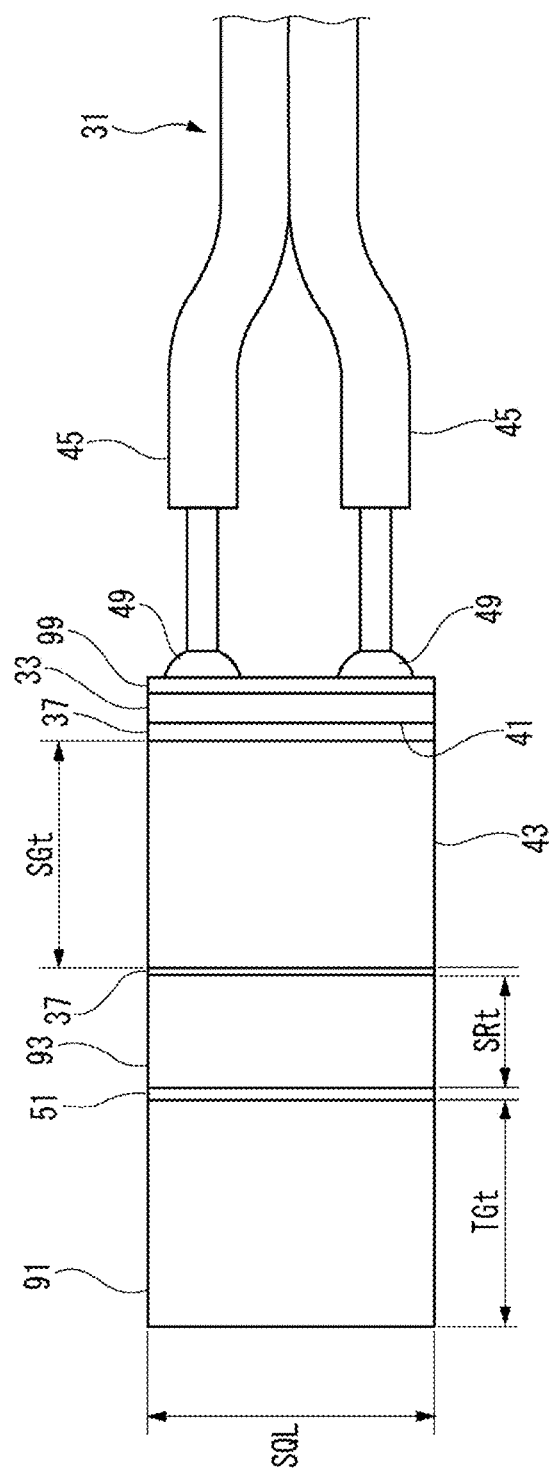
FIG. 23 is a side view illustrating an example of the dimensions of objective cover glass, the lens, and sensor cover glass.

FIG. 23 is a side view illustrating an example of the dimensions of the objective cover glass, the lens, and the sensor cover glass. In the endoscope 111 of the twenty-first configuration example in the embodiment, a thickness TGt of the objective cover glass 91 in a direction along the optical axis, a thickness SRt of the lens 93, and a thickness SGt of the sensor cover glass 43 are set to a range from 0.1 mm to 0.5 mm. The shape of the objective cover glass 91, the lens 93, the sensor cover glass 43, and the image sensor 33 is a square having one side length SQL of 0.5 mm. In the image sensor 33 illustrated in FIGS. 20 to 23, an electric circuit 99 with a thickness is illustrated. The bonding resin 37 with a thickness, with which the sensor cover glass 43 is bonded to the image sensor 33, is illustrated.

The sensor cover glass 43 acts to hold a distance between the lens 93 and the imaging area 41 according to the focal length and the optical characteristics of the lens 93. Since the thickness SGt of the sensor cover glass 43 is set to a range from 0.1 mm to 0.5 mm, the adjustment thereof is easy.

Since the thickness SRt is set to a range from 0.1 mm to 0.5 mm, the lens 93 is capable of acting as an optical sensor, and it is possible to ensure the air layer 95.

Since the thickness TGt is set to a range from 0.1 mm to 0.5 mm, the objective cover glass 91 can be used alone without the use of other reinforcement members. It is possible to prevent the reduction of the angle of view caused by the kicking of light beams which results from an unnecessary thickness increase.

As described above, in the endoscope 111 of the twenty-first configuration example, it is possible to prevent the reduction of the angle of view, and to prevent the increase of dimensions from the objective cover glass 91 to the image sensor 33 in the direction along the optical axis while holding an adequate distance between the lens 93 and the image sensor 33, and easily ensuring the air layer 95.

<Twenty-second Configuration Example>

As illustrated in FIG. 20, the endoscope 111 of the twenty-second configuration example in the embodiment includes the molded part 65, in which an outer circumferential surface of the objective cover glass 91 apart from an objective surface, an outer circumferential surface of the lens 93, and the image sensor 33 are coated with and are fixed by the molded resin 17, and which forms an outer shell of the distal portion 15 and is exposed to the outside; and the tubular sheath 61 that is formed to have the same outer diameter as that of the distal portion 15, covers at least a portion of the molded part 65, and is connected to the molded part 65.

As described above, the sheath 61 is made of a resin material having flexibility. As described above, for the purpose of imparting strength to the sheath 61, a single cable, multiple cables, a braided tensile strength cable may be provided on the inner circumferential side of the sheath 61. The tensile strength cable is made of the aforementioned same material.

In the endoscope 111, the objective cover glass 91, the lens 93, the sensor cover glass 43, the entire image sensor 33, a portion of the transmission cable 31, and a portion of the light guides 57 are coated with and are fixed by the molded resin 17. The molded resin 17 is exposed to the outside. The distal portion 15 of the endoscope 111 may involve a radiopaque marker. As a result, it is possible to easily confirm a distal end position of the endoscope 111 in radioscopy.

In the endoscopes 111, since the objective cover glass 91, the lens 93, the sensor cover glass 43, the image sensor 33, a portion of the transmission cable 31, and a portion of the light guides 57 (image unit) are coated with and are fixed by the molded resin 17, the number of interposed members required to fix the members is small. Accordingly, it is possible to reduce the diameter of the distal portion 15 of the endoscope 111. Also, in a case where a further thinning of the distal portion 15 is attempted, it is possible to configure the distal portion 15 with the minimum dimensions. In addition, it is possible to reduce component costs. It is possible to realize the endoscope 111 capable of capturing an image of a very thin target lesion such as a blood vessel of a human body. As a result, it is possible to reduce the size and the cost of the endoscope 111.

The molded resin 17 is molded so as to cover a region from the image sensor 33 to the objective cover glass 91, thereby contributing to an increase in the fixing strength of the image unit. The molded resin 17 increases the air tightness (that is, there are not many small gaps), the water tightness, and the light shielding properties of the air layer 95. The molded resin 17 also increases the light shielding properties when the optical fibers 59 for the light guides 57 are embedded.

Since the molded resin 17 is molded over the light guides 57, the light guides 57 act as a structural member in the distal portion 15 of the endoscope 111, and it is possible to improve connection strength between the soft portion 29 and the distal portion 15 in the thin endoscope 111. Since the objective cover glass 91 of the distal portion 15 and the four optical fibers 59 are coated with the molded resin 17, when the distal portion 15 is viewed from an insertion side outermost surface (refer to FIG. 19), there is no clearance on the circumference (that is, gap on the circumference) of each of the objective cover glass 91 and the four optical fibers 59 in the endoscope 111. As a result, when the endoscope 111 is sterilized (that is, is cleaned) after use in an examination or surgery, it is possible to reduce the amount of adherence of cleaning residuals such as unwanted liquid to the endoscope 111, and the endoscope 111 is capable of providing a higher level of convenience from the perspective of sanitation when the endoscope 111 will be used in a next examination or surgery compared to the endoscope 11 of the first embodiment.

In the endoscope 533 in the related art disclosed in WO2013/146091, the axial line of the distal portion is offset from the optical axis of the lens unit 547. For this reason, a distance to a subject is likely to change according to the rotational angle of the distal portion, and it is difficult to stably obtain a good quality image. If the axial line of the distal portion is offset from the optical axis of the lens unit 547, the state of interference between a duct inner wall and the distal portion is changed according to the rotational angle of the distal portion, and particularly, when the endoscope 533 is put into a thin hole, operability deteriorates. In contrast, in the endoscope 111, the objective cover glass 91, the lens 93, the sensor cover glass 43, and the image sensor 33 are coaxially continuous with each other. That is, the objective cover glass 91 is disposed concentrically with the distal portion 15. As a result, it is possible to easily thin the endoscopes 111 of the twenty-second configuration example, to stably obtain a good quality image, and to improve ease of insertion.

<Twenty-third Configuration Example>

In the endoscope 111 of the twenty-third configuration example, the thickness of the sheath 61 is preferably set to a range from 0.1 mm to 0.3 mm.

The molded part 65 of the endoscope 111 includes the small-diameter extension portion 71 illustrated in FIG. 20 which extends rearward from a rear end covering the image sensor 33. The small-diameter extension portion 71 is molded into a columnar shape, and the four optical fibers 59 are embedded in the small-diameter extension portion 71. The transmission cable 31 is embedded in the small-diameter extension portion 71 while being positioned inside the four optical fibers 59. The inner diameter side of the sheath 61 is fixed to the outer circumference of the small-diameter extension portion 71 with a bonding agent or the like. That is, the molded part 65 and the sheath 61 are coaxially continuous with each other with the maximum outer diameter Dmax set to 1.0 mm.

As described above, in the endoscope 111 of the twenty-third configuration example, since the thickness of the sheath 61 can be set up to 0.3 mm, it is possible to easily increase the tensile strength of the sheath 61. The minimum outer diameter of the existing transmission cable 31 is approximately 0.54 mm. If the maximum outer diameter Dmax of the distal portion 15 is set to 1.0 mm, the thickness of the sheath 61 is 0.23 mm. Since the thickness of the sheath 61 is set to the range from 0.1 mm to 0.3 mm, it is possible to set the maximum outer diameter Dmax of the distal portion 15 of the endoscope 111 to 1.0 mm.

Hereinafter, a method of manufacturing the endoscopes having the configurations in the embodiments (a step of manufacturing a distal portion) will be described. Hereinafter, a method of manufacturing the endoscope 11 of the first embodiment will be described as a representative example.

Figure 24A:
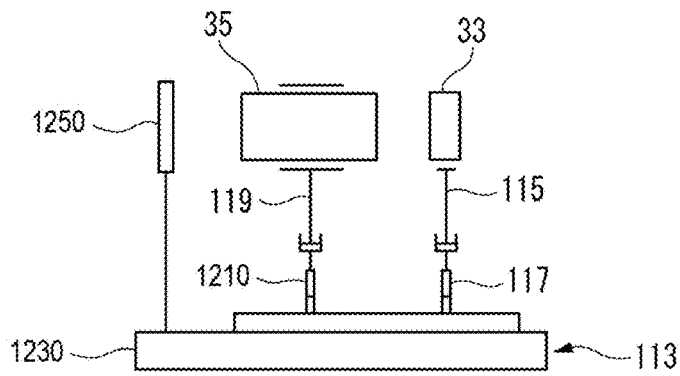
FIG. 24A is a view illustrating the configuration of a position adjustment jig.
Figure 24B:
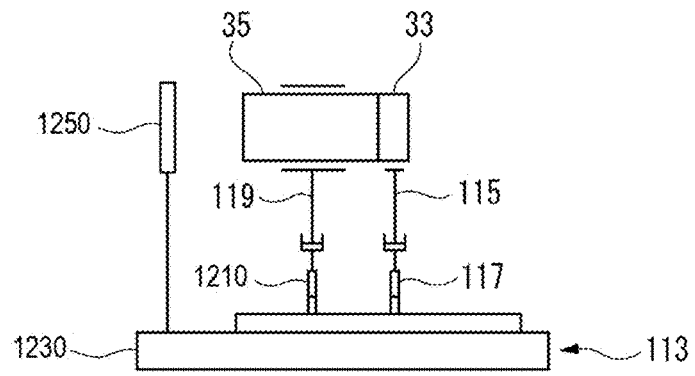
FIG. 24B is a side view when the lens unit is fixed to the image sensor.
Figure 24C:
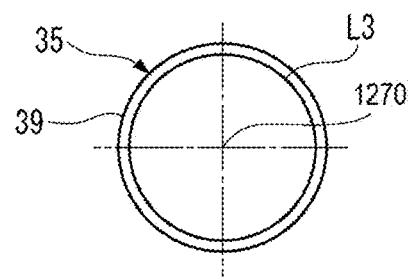
FIG. 24C is a video when position alignment in X and Y directions is performed.
Figure 24D:
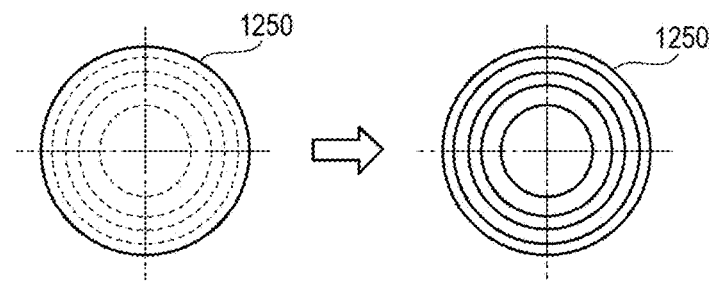
FIG. 24D is a video when position alignment in a Z direction is performed.

FIGS. 24A to 24D are views illustrating a first example of the endoscope manufacturing method. FIG. 24A is a view illustrating the configuration of a position adjustment jig. FIG. 24B is a side view when the lens unit is fixed to the image sensor. FIG. 24C is a video when position alignment in X and Y directions is performed. FIG. 24D is a video when position alignment in a Z direction is performed. The X and Y directions respectively refer to the rightward and leftward direction and the upward and downward direction illustrated in FIG. 1. The Z direction refers to the forward and rearward direction illustrated in FIG. 1.

In the first example of the endoscope manufacturing method, a rear end of the lens unit 35 is blocked by and is fixed to the image sensor 33 via a position adjustment jig 113. The position adjustment jig 113 includes a sensor support portion 115; a first XYZ stage 117; a lens unit support portion 119; a second XYZ stage 1210; a flat platen 1230; and a test chart 1250.

The sensor support portion 115 supports a lower surface of the image sensor 33. The first XYZ stage 117 holds the sensor support portion 115, and is capable of adjusting the position of the sensor support portion 115 in the forward and rearward direction and the upward and downward direction (it is desired to use a macro stage). The lens unit support portion 119 horizontally supports the lens unit 35 via both side surfaces. The second XYZ stage 1210 holds the lens unit support portion 119, and is capable of adjusting the position of the lens unit support portion 119 in the forward and rearward direction and the upward and downward direction. The test chart 1250 is a subject of the lens unit 35. The test chart 1250 includes a pattern which can be referred to for vignetting and the focus of a subject image when an image of the subject is captured. The flat platen 1230 supports all of the test chart 1250, the sensor support portion 115, and the lens unit support portion 119.

The assembly of the distal portion 15 is performed via the position adjustment jig 113, and basically, is manually performed by a worker via a microscope.

First, the bonding resin 37 is applied to at least one of the lens unit 35 and the image sensor 33 in advance. With reference to an image captured by the image sensor 33, the optical axis of the lens unit 35 is positionally aligned with the center of the imaging area 41 of the image sensor 33 while the lens unit 35 is supported and the image sensor 33 supported by the first XYZ stage 117 is moved. Specifically, as illustrated in FIG. 24C, the center of the lens support member 39 and the lens L3 is positionally aligned with a video center 1270. A video of the image sensor 33 is obtained by connecting a probe (not illustrated) to a terminal of the image sensor 33, reading a video signal, and displaying an image on the display apparatus (not illustrated).

Subsequently, the lens unit 35 is positionally aligned with the image sensor 33 in the direction along the optical axis. In a position alignment step, as illustrated in FIG. 24D, light incident from the test chart 1250 is focused on the imaging area 41 of the image sensor 33 by adjusting the position of the lens unit 35 in the forward and rearward direction. That is, as illustrated in FIG. 24B, focusing is performed by adjusting the position of the lens unit 35 in the direction of an optical axis LC.

When the position of the lens unit 35 is adjusted, the transmission cable 31 may be or may not be connected to the conductor connection parts 49. If the transmission cable 31 is not connected to the conductor connection parts 49, as described above, a probe is connected to the terminal of the image sensor 33, a video signal is read, and an image of the subject for test is displayed on the display apparatus.

If the transmission cable 31 is connected to the image sensor 33, an output of the image sensor 33 may be processed by the video processor 19, and may be displayed on the display apparatus. It is possible to easily adjust the position of the lens unit 35 and to reduce the length of time required for the position alignment step by using the test chart (for example, resolution chart) 125 which is a predetermined subject.

When the position alignment between the lens unit 35 and the image sensor 33 is complete, desirably, the bonding resin 37 is slightly exposed between the lens unit 35 and the image sensor 33. If the amount of the bonding resin 37 is insufficient, the bonding resin 37 is injected between the lens unit 35 and the image sensor 33. A gap between the lens unit 35 and the image sensor 33 is filled with the injected bonding resin 37 due to a capillary phenomenon.

After the image sensor 33 is positionally aligned with the rear end of the lens unit 35, the bonding resin 37 is hardened via ultraviolet light illumination, and the lens unit 35 is temporarily fixed to the image sensor 33 with the bonding resin 37. In a state where the positions of the lens unit 35 and the image sensor 33 relative to each other in the forward and rearward direction are maintained, ultraviolet light illumination is applied to the exposed bonding resin 37. If the bonding resin 37 is hardened via the ultraviolet light illumination, the image sensor 33 is temporarily fixed to the vicinity of the rear end of the lens unit 35. Since the bonding resin 37 is hardened within a short time of approximately several seconds via ultraviolet light illumination, it is possible to reduce the length of time required for the step. The lens unit 35 and the image sensor 33 which are temporarily fixed together are detached from the position adjustment jig 113.

Thereafter, the bonding resin 37 is further hardened via a heat treatment, and the lens unit 35 is permanently fixed to the image sensor 33 with the bonding resin 37. If the bonding resin 37 is hardened via a heat treatment, the lens unit 35 is firmly fixed to the image sensor 33.

Subsequently, the molded resin 17 is molded over the distal portion 15 such that a rear portion of the lens unit 35 and the image sensor 33 are covered with the molded resin 17. In a molding step, a sealing portion is configured by applying and firmly fixing the molded resin 17 to the lens unit 35, at least the image sensor 33, the conductor connection parts 49, and a distal end (portion electrically connected to the image sensor 33) of the transmission cable 31 which are positioned rearward from the rear end of the lens unit 35.

At this time, the molded resin 17 is applied so as to exceed a front surface of the image sensor 33 and to cover the rear end of the lens unit 35, and thus, the separation part 47 is reliably blocked. The molded resin 17 used has a high viscosity to the extent that at least the image sensor 33, the conductor connection parts 49, the distal end of the transmission cable 31, and gaps are covered with the molded resin 17. For the main purpose of sealing, the molded resin 17 is applied and prevents the infiltration of moisture into the distal portion 15 from the rear side of the image sensor 33 and the separation part 47.

The sealing portion may be formed via a resin die so as to easily form the molded resin 17 into the illustrated shape. In this case, the resin die (not illustrated) is disposed in advance so as to cover a region from the rear end of the lens unit 35 to the distal end of the transmission cable 31. The molded resin 17 is allowed to flow into the resin die, and is hardened, and the resin die is detached.

Various well-known bonding agents may be used as the molded resin 17. For example, a bonding agent formed of thermosetting resin such as epoxy resin and acrylic resin may be used. In addition, black resin containing carbon particles is desirably adopted. As a result, it is possible to prevent the incidence of stray light to the imaging area 41 of the image sensor 33 from the outside.

Thereafter, the distal portion 15 is placed in an environment of 60° C. to 80° C. for approximately 30 minutes. As a result, the molded resin 17 covering the image sensor 33, the conductor connection parts 49, the distal end of the transmission cable 31, and the separation part 47 is completely hardened. If the molding step is complete, the assembly of the distal portion 15 to the endoscope 11 is complete.

Figure 25A:
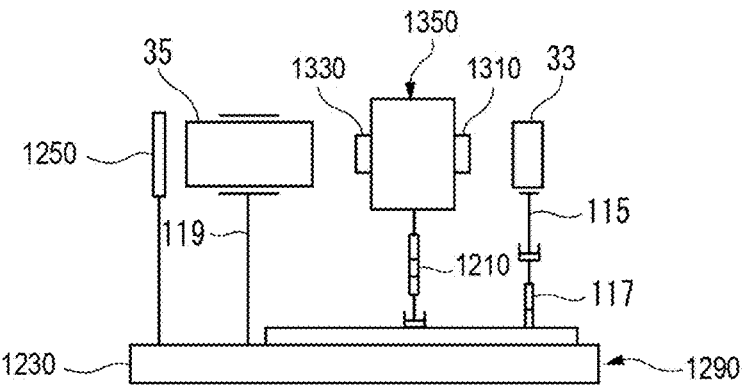
FIG. 25A is a view illustrating the configuration of a camera-mounted position adjustment jig.
Figure 25B:
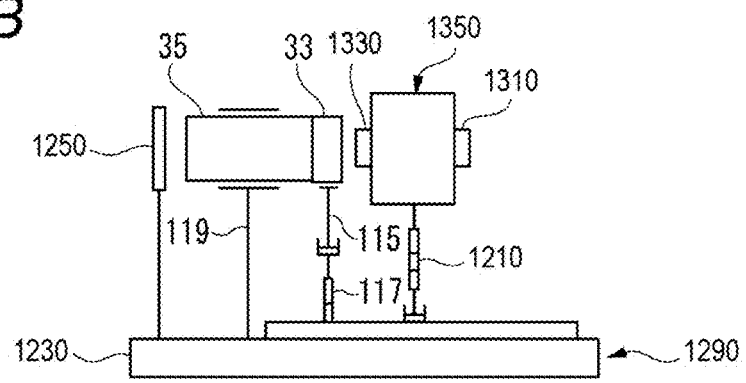
FIG. 25B is a side view when the lens unit is fixed to the image sensor.
Figure 25C:
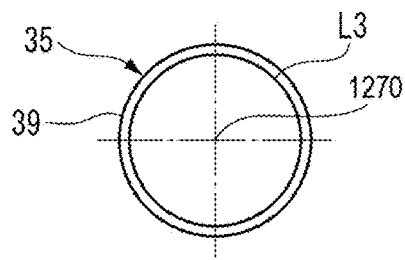
FIG. 25C is a video when position alignment is performed via a second camera.
Figure 25D:
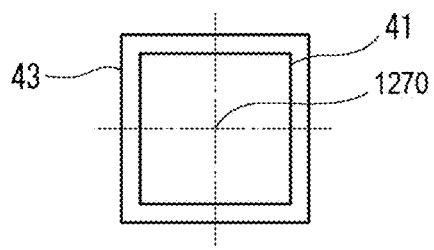
FIG. 25D is a video when position alignment is performed via a first camera.
Figure 25E:
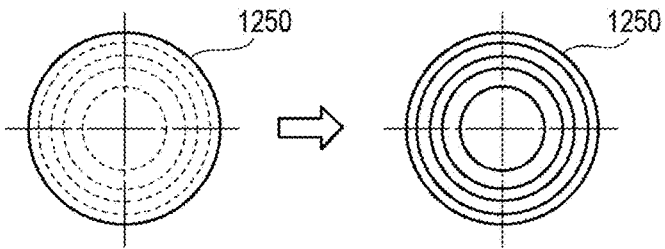
FIG. 25E is a video when position alignment in the Z direction is performed.

FIGS. 25A to 25E are views illustrating a second example of the endoscope manufacturing method. FIG. 25A is a view illustrating the configuration of a camera-mounted position adjustment jig. FIG. 25B is a side view when the lens unit is fixed to the image sensor. FIG. 25C is a video when position alignment is performed via a second camera. FIG. 25D is a video when position alignment is performed via a first camera. FIG. 25E is a video when position alignment in the Z direction is performed. The same reference signs are assigned to the same members as those illustrated in FIGS. 24A to 24D, and duplicated description will be omitted. Similar to the first example, the X and Y directions respectively refer to the rightward and leftward direction and the upward and downward direction illustrated in FIG. 1. The Z direction refers to the forward and rearward direction illustrated in FIG. 1.

In the second example of the endoscope manufacturing method, the rear end of the lens unit 35 is blocked by and is fixed to the image sensor 33 via a camera-mounted position adjustment jig 1290. The camera-mounted position adjustment jig 1290 includes a first video camera-mounted microscope (hereinafter, referred to as a "first camera 1310") which observes the image sensor 33 from the front side, and a second video camera-mounted microscope (hereinafter, referred to as a "second camera 1330") which observes the lens unit 35 from the rear side.

The first camera 1310 and the second camera 1330 are configured in an integrated manner, and are configured to be capable of capturing images of the right and left sides (or, upper and lower sides, front and rear sides) at the same time. Hereinafter, an integral camera is referred to as a "right and left camera 135". The imaging directions of the first camera 1310 and the second camera 1330 are 180 degrees opposed to each other in a state where the optical axes of the first camera 1310 and the second camera 1330 are aligned with each other with very high accuracy. The right and left camera 1350 is attached to the second XYZ stage 1210, and is disposed between the sensor support portion 115 and the lens unit support portion 119 of the camera-mounted position adjustment jig 1290. The sensor support portion 115 is supported by the first XYZ stage 117. The first XYZ stage 117, the second XYZ stage 1210, and the lens unit support portion 119 are provided on the flat platen 1230. The test chart 1250 is attached to the flat platen 1230.

In the camera-mounted position adjustment jig 1290, a parallelism between the sensor support portion 115 supported by the first XYZ stage 117 and the lens unit support portion 119 is adjusted in advance, and alignment therebetween is performed with high accuracy. In the mounting of the image sensor 33, a bottom surface of the image sensor 33 is temporarily fastened to the sensor support portion 115. In an example of a temporary fastening method, many fine holes may be provided in the sensor support portion 115, the fine holes may be connected to a vacuum pump, and the image sensor 33 may be vacuum-suctioned.

The assembly of the distal portion 15 is performed via the camera-mounted position adjustment jig 1290, and basically, is manually performed by a worker via a microscope. First, the bonding resin 37 is applied to at least one of the lens unit 35 and the image sensor 33 in advance.

As illustrated in FIG. 25A, the right and left camera 135 including the first camera 1310 and the second camera 1330 having the coincident optical axis is disposed between the image sensor 33 and the lens unit 35. Subsequently, as illustrated in FIG. 25D, with reference to a video captured by the first camera 1310, the center of the imaging area 41 of the image sensor 33 is moved to the video center 1270. As illustrated in FIG. 25C, with reference to a video captured by the second camera 1330, the center of the lens unit 35 is moved to the video center 1270. Thereafter, after the right and left camera 135 is retracted as illustrated in FIG. 25B, as illustrated in FIG. 25E, with reference to a video captured by the image sensor 33, a distance between the lens unit 35 and the image sensor 33 in the direction along the optical axis is adjusted.

In a position alignment step, the right and left camera 135 (precisely, optical axis of the right and left camera 135) is aligned with the center (central position in the radial direction) of the lens unit 35 by adjusting the position of the second XYZ stage 1210 with reference to the video of the rear end of the lens unit 35 captured by the second camera 1330. With reference to the video captured by the first camera 1310, the position of the first XYZ stage 117 in the rightward and leftward direction is adjusted, and the center of the imaging area 41 of the image sensor 33 supported by the sensor support portion 115 is moved to the center of an XY coordinate on a screen, that is, to the central position of the lens unit 35. As a result, even if the center of the imaging area 41 of the image sensor 33, that is, the optical axis LC varies due to a solid, the lens unit 35 can be positionally aligned with the image sensor 33 with respect to the optical axis LC which is a datum.

The right and left camera 135 is retracted from a position between the sensor support portion 115 and the lens unit support portion 119, the position of the first XYZ stage 117 in the forward and rearward direction is adjusted, and the image sensor 33 supported by the sensor support portion 115 is brought into contact with the rear end of the lens unit 35.

After the image sensor 33 is positionally aligned with the rear end of the lens unit 35 in the aforementioned operations, similar to the first example, the bonding resin 37 is hardened by irradiating an exposed coating portion of the bonding resin 37 with ultraviolet light, and the lens unit 35 is temporarily fixed to the image sensor 33 with the bonding resin 37. As such, the image sensor 33 is mounted to the rear end of the lens unit 35 after position alignment.

Thereafter, similar to the first example, the lens unit 35 is permanently fixed to the image sensor 33 with the bonding resin 37 via a heat treatment. Subsequently, similar to the first example, a molding process is performed, and the assembly of the distal portion 15 to the endoscope 11 is complete.

(Third Embodiment)

Hereinafter, an endoscope 121 of a third embodiment will be described.

FIG. 26 is a sectional view illustrating an example of a distal portion of the endoscope 121 of the third embodiment. In the third embodiment, the same reference signs are assigned to the same members as those described in the first embodiment and the second embodiment, and duplicated description will be omitted.

A feature of the endoscope 121 of the third embodiment is that the cover tube 69 is not provided. In the endoscope 121, the maximum outer diameter Dmax of the distal portion 15 is 1.8 mm. The molded part 65 includes the small-diameter extension portion 71 that extends toward an opposite side of the distal flange portion 63 from a large-diameter molded body 123.

The sheath 61 has flexibility, and covers the lenses L1, L2, and L3, the image sensor 33, a portion of the illuminator (for example, light guides 57), and the transmission cable 31 so as to protect the distal portion 15 of the endoscope 121. The sheath 61 is formed to have the same outer diameter (that is, maximum outer diameter Dmax) as that of the distal flange portion 63. In contrast, an inner circumferential portion of the sheath 61, which covers the small-diameter extension portion 71, has a small diameter. An inner circumferential portion of the sheath 61, which covers the molded body 123, has a large diameter. As a result, the portion of the sheath 61, which covers the small-diameter extension portion 71, becomes a thick wall portion 125, and the portion of the sheath 61, which covers the molded body 123, becomes a thin wall portion 127. A stepped portion 129 is formed between the thick wall portion 125 and the thin wall portion 127 on the inner circumference of the sheath 61. The stepped portion 129 is filled with a sheath bonding agent 131.

Similar to the endoscope 11 of the first embodiment, it is possible to realize a further thinning of the distal portion 15 of the endoscope 121. Since the endoscope 121 does not require the cover tube 69, it is possible to reduce the number of components. Since the distal portion 15 of the endoscope 121 is soft in comparison with that of the endoscope 11 including the cover tube 69 made of metal such as stainless steel (for example, SUS316), the endoscope 121 is capable of absorbing an impact applied when the endoscope 121 is inserted into a body or the like. Since the endoscope 121 absorbs an impact well in comparison with that in a case where the distal portion 15 is made of metal, an operator can easily perform an operation. That is, it is possible to improve operability.

<Twenty-fourth Configuration Example>

Figure 27:
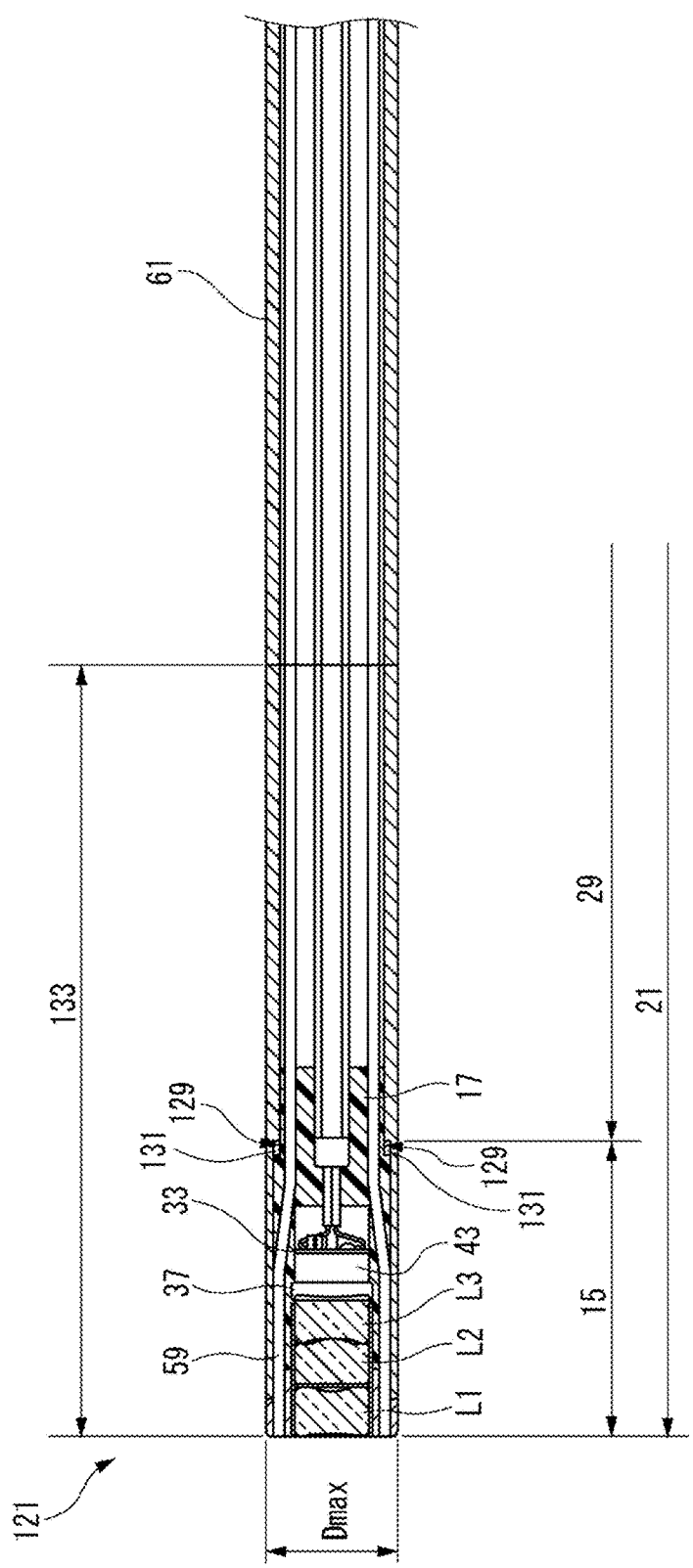
FIG. 27 is a sectional view illustrating an example of the distal portion of the endoscope in which the hardness of a sheath differs in a stepwise manner.
Figure 28:
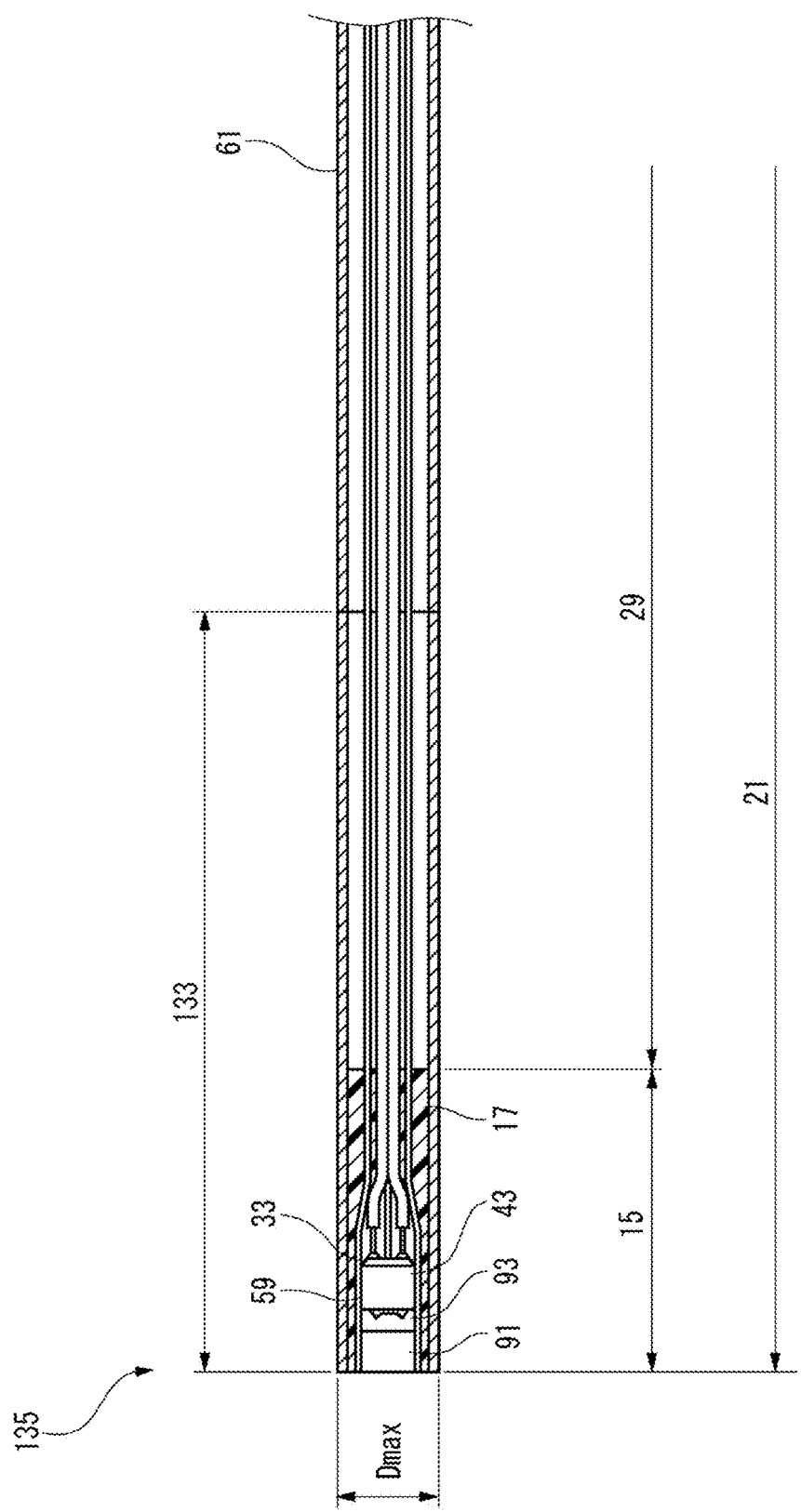
FIG. 28 is a sectional view illustrating another example of a distal portion of an endoscope in which the hardness of the sheath differs in a stepwise manner.

FIG. 27 is a sectional view illustrating an example of the distal portion of the endoscope 121 in which the hardness of the sheath 61 differs in a stepwise manner. FIG. 28 is a sectional view illustrating another example of a distal portion of an endoscope 135 in which the hardness of the sheath differs in a stepwise manner.

The hardness of the sheath 61 may differ according to positions on the insertion part 21 of the endoscope 121. That is, the sheath 61 of the endoscope 121 includes a distal low hardness portion 133 having a low hardness on a distal side of the insertion part 21. The hardness of other portion (that is, a rear end side portion or a portion other than the portion on the distal side) further increases in a stepwise manner than that of the distal low hardness portion 133. This configuration can be similarly applied to the endoscope 121 having the maximum outer diameter Dmax of 1.8 mm illustrated in FIG. 27, and the endoscope 135 having the maximum outer diameter Dmax of 1.0 mm illustrated in FIG. 28.

When using the endoscope 121 or 135, an operator inserts the distal portion 15 of the endoscope 121 into an insertion opening (not illustrated) of a catheter acting as an insertion guide. At this time, the operator holds a portion (positioned a predetermined length rearward from the distal portion 15) of the endoscope 121 or 135 with fingers, and inserts the distal portion 15 into the insertion opening. If the distal portion 15 is inserted into the insertion opening, thereafter, the endoscope 121 or 135 is quickly inserted. The strong holding of the endoscope 121 or 135 has to be prevented from causing damage to the endoscope 121 or 135 for a particularly thin blood vessel. Since the endoscopes 121 and 135 include the distal low hardness portion 133 having a predetermined length from the distal end, and the hardness of other portion (that is, a rear end side portion or a portion other than the portion on the distal side) further increases in a stepwise manner than that of the distal low hardness portion 133, it is possible to ensure operability of and to prevent damage to the endoscopes 121 and 135.

The length of the distal low hardness portion 133 may be set to 50 mm to 300 mm. If the length of the distal low hardness portion 133 is 50 mm or greater, it is possible to ensure operability. If the length of the distal low hardness portion 133 is 300 mm or less, it is possible to reduce a risk of damage.

<Twenty-fifth Configuration Example>

Figure 29:
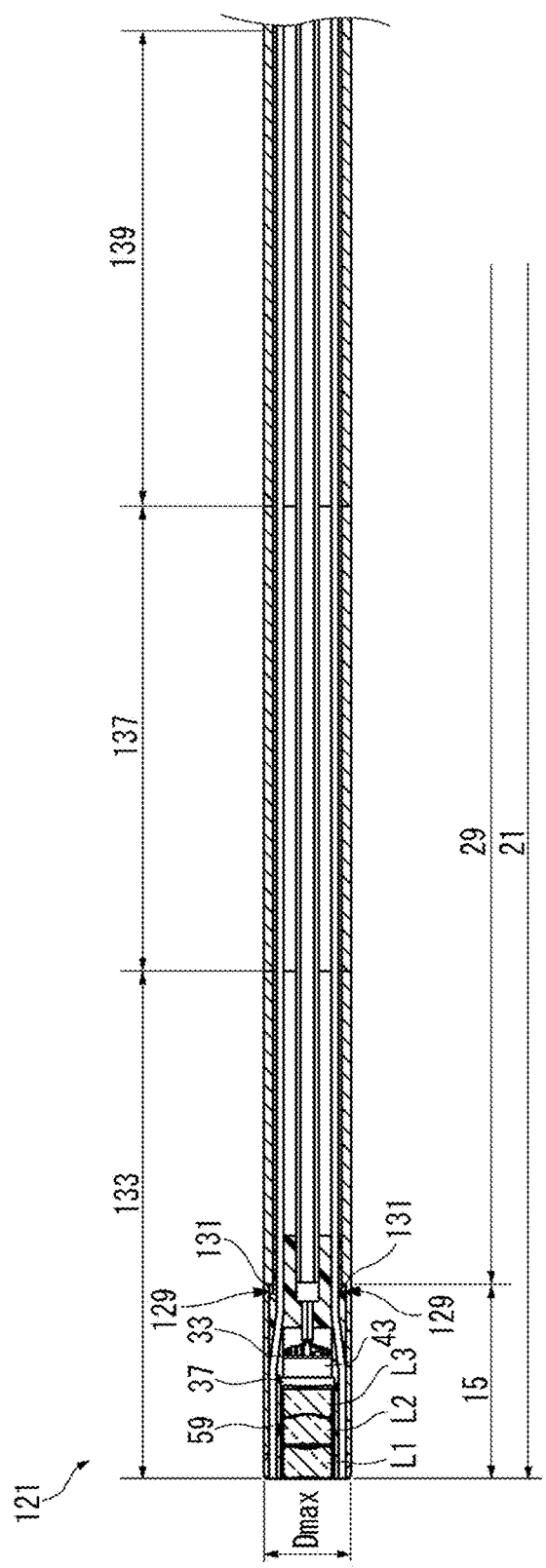
FIG. 29 is a sectional view illustrating an example of the distal portion of the endoscope in which the hardness of the sheath differs in a stepwise manner, that is, in three stages.
Figure 30:
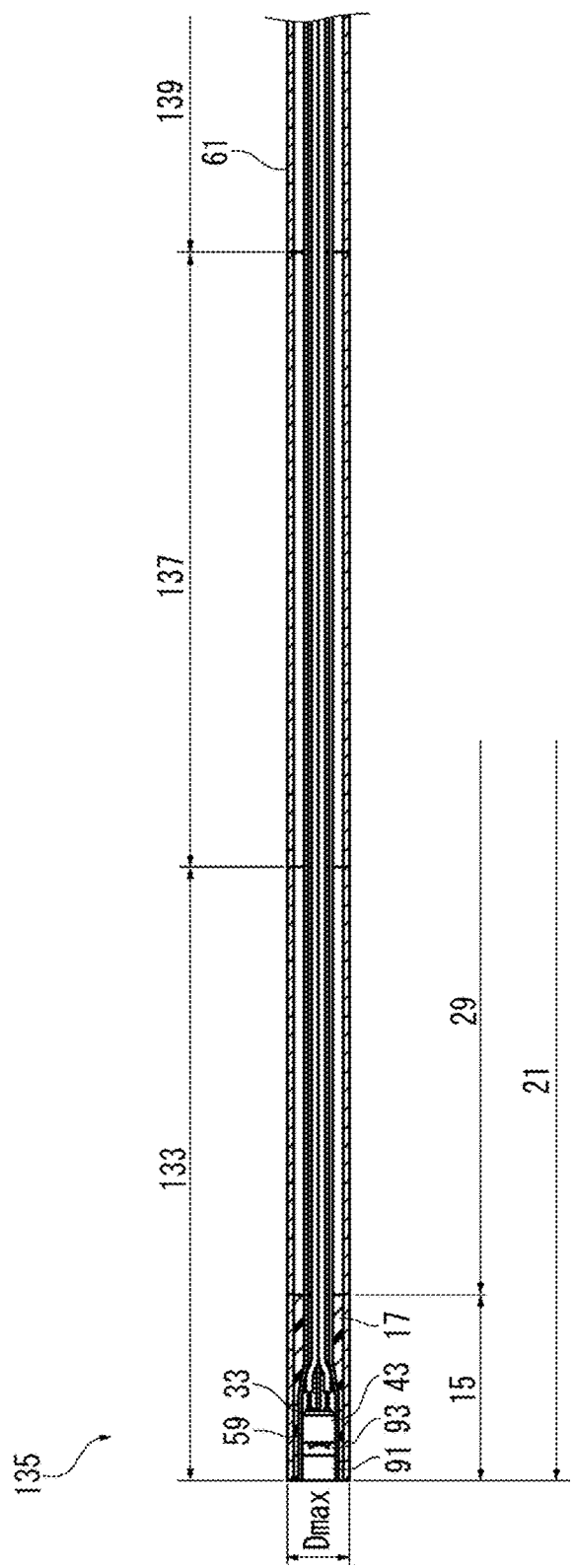
FIG. 30 is a sectional view illustrating another example of the distal portion of the endoscope in which the hardness of the sheath differs in a stepwise manner, that is, in three stages.

FIG. 29 is a sectional view illustrating an example of the distal portion of the endoscope 121 in which the hardness of the sheath 61 differs in a stepwise manner, that is, in three stages. FIG. 30 is a sectional view illustrating another example of the distal portion of the endoscope 135 in which the hardness of the sheath differs in a stepwise manner, that is, in three stages. The hardness of the sheath 61 of the endoscope 121 may differ in three stages. In this case, the sheath 61 of the endoscope 121 includes the distal low hardness portion 133 having a low hardness on the distal side of the insertion part 21. The distal low hardness portion 133 is connected to a connection medium hardness portion 137 having a hardness higher than that of the distal low hardness portion 133 in a stepwise manner. A high hardness portion 139 having a hardness, which is higher than that of the connection medium hardness portion 137 in a stepwise manner, is connected to a side of the connection medium hardness portion 137 opposite to the distal low hardness portion 133. This configuration can be similarly applied to the endoscope 121 having the maximum outer diameter Dmax of 1.8 mm illustrated in FIG. 29, and the endoscope 135 having the maximum outer diameter Dmax of 1.0 mm illustrated in FIG. 30.

FIG. 31 is a table illustrating an example of hardness values at positions on the insertion part. In the endoscopes 121 and 135 in which the hardness of the sheath 61 differs in three stages, the hardness values of the distal low hardness portion 133, the connection medium hardness portion 137, and the high hardness portion 139 are preferably set to ranges illustrated in FIG. 31. That is, the Shore D hardness of the distal low hardness portion 133 is preferably set to 25 to 55. The Shore D hardness of the connection medium hardness portion 137 is preferably set to 40 to 65. The Shore D hardness of the high hardness portion 139 is preferably set to 60 to 75. If the distal low hardness portion 133 is softer than a Shore D hardness of 25, a risk of damage increases.

If the high hardness portion 139 is harder than a Shore D hardness of 75, a risk of damage increases.

If portions of the sheath 61 have different hardnesses, the melting points of the portions are different from each other. In this case, the joining of both is performed at a high melting temperature. A resin material having a low melting point is heated at a temperature considerably exceeding the melting point. Due to the overheating, sinks or voids are likely to occur in the resin material, a bonding surface becomes unstable, and bonding strength decreases. In the endoscopes 121 and 135, the connection medium hardness portion 137 is interposed between the distal low hardness portion 133 and the high hardness portion 139. The connection medium hardness portion 137 is capable of reducing a difference in melting points. Accordingly, in the endoscopes 121 and 135 in which the hardness of the sheath 61 differs in three stages, it is possible to prevent the overheating of the resin materials when connection is performed.

In the endoscopes 121 and 135, since the distal end has necessary softness, a hand side has necessary hardness, and the connection medium hardness portion 137 is interposed therebetween, it is possible to solve the aforementioned manufacturing problem (that is, a decrease in the bonding strength of the bonding surface).

<Twenty-sixth Configuration Example>

In the endoscope 121, the molded body 123 includes the small-diameter extension portion 71 illustrated in FIG. 26. As a result, the sheath 61 includes the thick wall portion 125 and the thin wall portion 127. In the endoscope 121, an extension end surface 141 of the small-diameter extension portion 71 is disposed in the thick wall portion 125 of the sheath 61. A cavity 143 is formed inside the sheath 61, and is positioned opposite to the molded body 123 with respect to the extension end surface 141.

Figure 32:
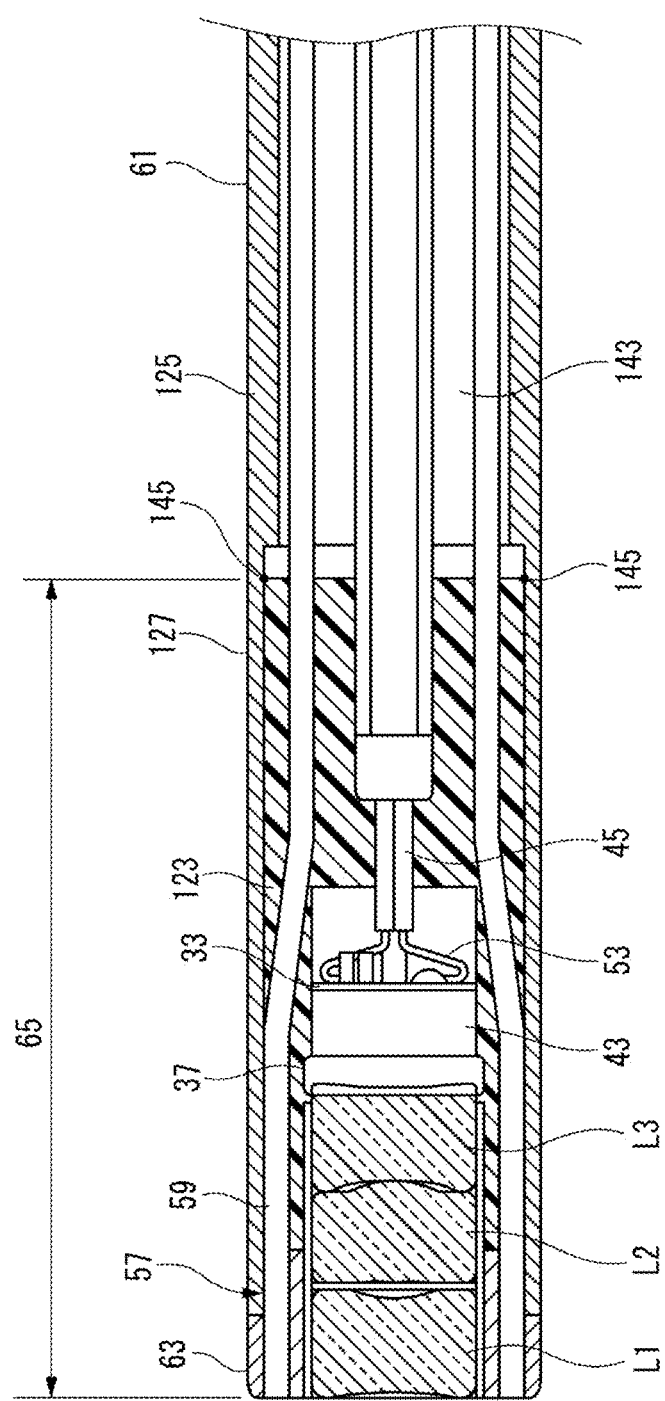
FIG. 32 is a sectional view illustrating a configuration in which a small-diameter extension portion is not formed in a mold.
Figure 33:
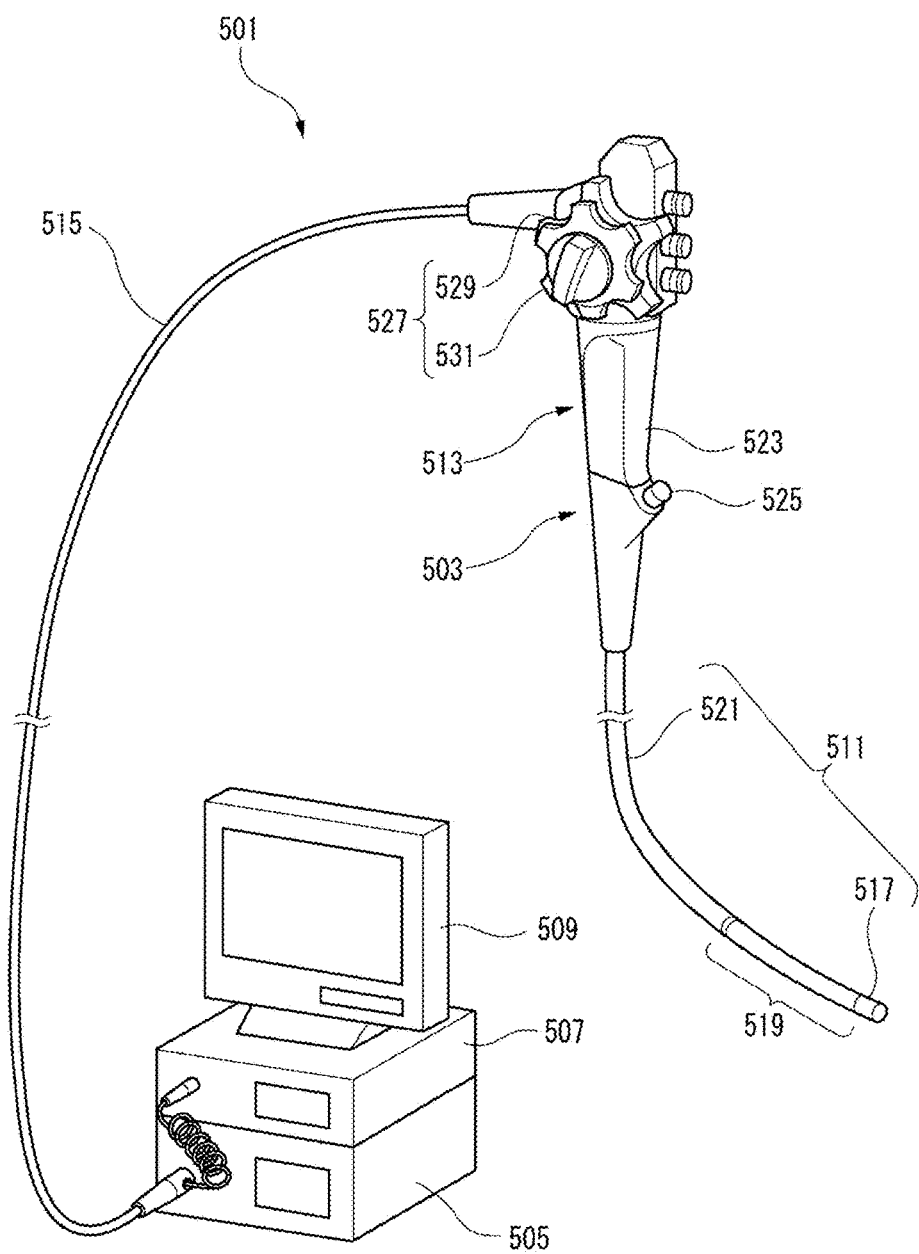
FIG. 33 is a view illustrating the entire configuration of an electronic endoscopic system including an endoscope in the related art.
Figure 34:
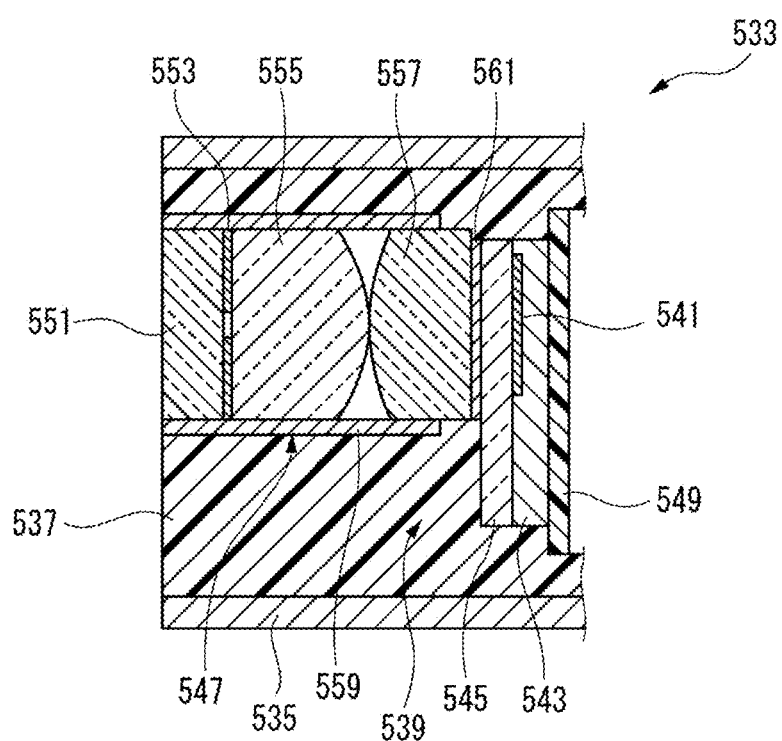
FIG. 34 is a partial sectional view illustrating the structure of an end portion of the endoscope in the related art.

FIG. 32 is a sectional view illustrating a configuration in which the small-diameter extension portion 71 is not formed in the molded part 65. In a case where the extension end surface 141 is not provided in an endoscope, if the sheath 61 is bent, as illustrated in FIG. 32, stress occurring due to the bending of the sheath 61 concentrates at a body rear end portion 145 of the molded body 123. That is, stress concentrates at the thin wall portion 127. In contrast, in the configuration in which the extension end surface 141 is provided in the endoscope 121 illustrated in FIG. 26, the extension end surface 141 is disposed in the thick wall portion 125, and thus, when the sheath 61 is bent, stress occurring due to the bending of the sheath 61 concentrates in the thick wall portion 125 of the sheath 61. Accordingly, the concentration of stress at the thin wall portion 127 is avoided in the endoscope 121. As a result, damage to the sheath 61 may not be likely to occur. This approach is effective in main portions of a particularly thin endoscope in many thin wall members are used.

Various embodiments have been described with reference to the accompanying drawings; however, the present invention is not limited to the examples. It is apparent to persons skilled in the art that the persons can conceive various change or modification examples within the scope of the claims. It is ascertained that the various change or modification examples are naturally included in the technical scope of the present invention. Various configuration elements in the embodiments may be arbitrarily combined together insofar as the combinations do not depart from the concept of the invention.

According to the present invention, there is provided an endoscope including: a single lens having a square exterior shape in a direction perpendicular to an optical axis; an image sensor that has same exterior shape as the exterior shape of the single lens in the direction perpendicular to the optical axis; sensor cover glass that covers an imaging area of the image sensor, and has same exterior shape as the exterior shape of the single lens in the direction perpendicular to the optical axis; bonding resin with which the sensor cover glass is fixed to the single lens, the optical axis of which coincides with a center of the imaging area; a transmission cable including four electric cables which are respectively connected to four conductor connection parts provided on the image sensor; and multiple illuminators that are provided along the optical axis, and are disposed equally spaced along an outer circumference of the single lens. The four conductor connection parts are collectively provided on a surface of the image sensor opposite to the imaging area, and the maximum outer diameter of a distal portion including the single lens and the illuminator is 1.0 mm.

According to the present invention, there is provided the endoscope in which the conductor connection parts are respectively disposed at four corners of the image sensor.

According to the present invention, there is provided the endoscope in which a central portion of the single lens includes a convex curved surface on an image side which forms a convex lens surface and protrudes in such a way as to form a substantially spherical surface, an end surface of a circumferential edge portion of the single lens is a flat surface, and the entire end surface has a bonding surface with respect to the sensor cover glass.

According to the present invention, there is provided the endoscope in which at least a portion of the single lens, the image sensor, a portion of the transmission cable, and a portion of the illuminator are coated with and are fixed by molded resin.

According to the present invention, there is provided an endoscope including: at least one lens having a circular exterior shape in a direction perpendicular to an optical axis; an image sensor that has a square exterior shape in the direction perpendicular to the optical axis, and has one side whose length is same as length of a diameter of the lens; a sensor cover that covers an imaging area of the image sensor, has a square exterior shape in the direction perpendicular to the optical axis, and has one side whose length is same as one side length of the image sensor; a bonding resin portion that fixes the sensor cover to the lens, the optical axis of the lens coinciding with a center of the imaging area; a transmission cable connected to the image sensor; an illuminator provided along the lens and the transmission cable; a tubular sheath that covers a portion of the illuminator and the transmission cable; and a cover tube that covers the lens, the image sensor, and a portion of the illuminator, is coaxially connected to the tubular sheath in a state that outer circumferential surface of the cover tube is flush and continuous with outer circumferential surface of the tubular sheath, and forms a distal portion. The cover tube is smaller in thickness than the tubular sheath, and the distal portion including the lens, the illuminator, and the cover tube has a maximum outer diameter of 1.8 mm.

According to the present invention, there is provided an endoscope including: a single lens having a square exterior shape in a direction perpendicular to an optical axis; an image sensor that has an exterior shape which is same as an exterior shape of the single lens, in the direction perpendicular to the optical axis; a sensor cover that covers an imaging area of the image sensor, and has an exterior shape which is same as the exterior shape of the single lens, in the direction perpendicular to the optical axis; a bonding resin portion that fixes the sensor cover to the single lens, the optical axis of the lens coinciding with a center of the imaging area; a transmission cable connected to the image sensor; an illuminator provided along the single lens and the transmission cable; a tubular sheath that covers a portion of the illuminator and the transmission cable; and a molded portion that covers and fixes the single lens, the image sensor, and a portion of the illuminator, and forms a distal portion. The molded portion is coaxially and continuously connected to the tubular sheath, and the distal portion including the single lens, the illuminator, and the molded portion has a maximum outer diameter of 1.0 mm.

According to the present invention, there is provided the endoscope in which the tubular sheath has a thickness of 0.1 mm to 0.3 mm.

According to the present invention, there is provided the endoscope in which multiple illuminators are provided along the lens and the transmission cable. Each illuminator is equiangularly disposed in a circumferential direction.

According to the present invention, there is provided an endoscope including: a single lens having a square exterior shape in a direction perpendicular to an optical axis; an image sensor that has same exterior shape as the exterior shape of the single lens in the direction perpendicular to the optical axis; sensor cover glass that covers an imaging area of the image sensor, and has same exterior shape as the exterior shape of the single lens in the direction perpendicular to the optical axis; and bonding resin with which the sensor cover glass is fixed to the single lens, the optical axis of which coincides with a center of the imaging area. The image sensor has a diagonal length dimension of approximately 0.7 mm. An air layer is provided between the single lens and the sensor cover glass. A central portion of the single lens includes a convex curved surface on an image side which forms a convex lens surface and protrudes to form a substantially spherical surface, an end surface of a circumferential edge portion of the single lens is a flat surface, and the entire end surface has a bonding surface with respect to the sensor cover glass.

According to the present invention, there is provided the endoscope in which the thicknesses of the single lens and the sensor cover glass in a direction along the optical axis are set to a range from 0.1 mm to 0.5 mm.

According to the present invention, there is provided the endoscope further including: a molded part in which an outer circumferential surface of the single lens and the image sensor are coated with and are fixed by molded resin, and which forms an outer shell of a distal portion including the single lens and is exposed to the outside; and a tubular sheath that is formed to have the same outer diameter as that of the distal portion, covers at least a portion of the molded part, and is connected to the molded part.

According to the present invention, there is provided the endoscope in which the thickness of the sheath is in a range from 0.1 mm to 0.3 mm.

According to the present invention, there is provided an endoscope including: a lens unit in which a front group lens and a rear group lens, which have a circular exterior shape in a direction perpendicular to an optical axis, are accommodated in a lens support member, and an aperture stop is disposed between the front group lens and the rear group lens; an image sensor that has a square exterior shape in the direction perpendicular to the optical axis, and has same one side length as a diameter of the front group lens and the rear group lens; sensor cover glass that covers an imaging area of the image sensor, has a square exterior shape in the direction perpendicular to the optical axis, and has same one side length as the one side length of the image sensor; bonding resin with which the lens unit is fixed to the sensor cover glass in a state where the optical axes of the front group lens and the rear group lens coincide with a center of the imaging area; and a rough surface portion that is formed in an outer circumferential surface of the rear group lens, and prevents the outer circumferential surface from totally reflecting light propagating through the rear group lens. The diagonal length dimension of the image sensor is approximately 1.4 mm.

According to the present invention, there is provided the endoscope in which the surface roughness of the rough surface portion is in a range from 0.1 µm to 10 µm.

According to the present invention, there is provided the endoscope in which the rough surface portion is formed in an end surface surrounding an image light emitting effective surface of an image side final surface of the rear group lens.

According to the present invention, there is provided an endoscope including: at least one lens; an image sensor that has a square exterior shape in a direction perpendicular to an optical axis, and has the same one side length as the diameter of the lens; sensor cover glass that covers an imaging area of the image sensor, has a square exterior shape in the direction perpendicular to the optical axis, and has the same one side length as that of the image sensor; a transmission cable connected to the image sensor; an illuminator provided along the lens and the transmission cable; a tubular sheath that has flexibility, and covers the lens, the image sensor, a portion of the illuminator, and the transmission cable. The sensor cover glass is fixed to the lens, the optical axis of which coincides with a center of the imaging area, with bonding resin.

According to the present invention, there is provided the endoscope in which the sheath includes a distal low hardness portion having a low hardness on a distal side of an insertion part, and the hardness of a portion other than the portion on the distal side of the insertion part is higher than that of the distal low hardness portion.

According to the present invention, there is provided the endoscope in which the distal low hardness portion is connected to a connection medium hardness portion having a hardness higher than that of the distal low hardness portion, and a high hardness portion having a hardness, which is higher than that of the connection medium hardness portion, is connected to a side of the connection medium hardness portion opposite to the distal low hardness portion.

According to the present invention, there is provided the endoscope further including a molded part that covers and fixes the lens, the image sensor, and a portion of the illuminator, and forms a distal portion. A small-diameter extension portion extending from a molded body is formed in the molded part. The sheath includes a stepped portion between a thick wall portion covering the molded body and a thin wall portion covering the small-diameter extension portion on an inner circumference of the sheath, and an extension end surface of the small-diameter extension portion is disposed in the thick wall portion of the sheath.

According to the present invention, it is possible to reduce the size and the cost of an endoscope. The present invention is effectively applied to a thin endoscope or the like used in a medical surgery.

In addition, this application is based on Japanese patent applications (Japanese Patent Application No. 2015-171550, 2015-171551, 2015-171552, 2015-171554) filed on Aug. 31, 2015 and a Japanese patent application (Japanese Patent Application No. 2016-076172) filed on Apr. 5, 2016, and contents thereof are incorporated herein by reference.

What is claimed is:

1. An endoscope comprising:
a lens unit that accommodates a front group lens and a rear group lens, an aperture stop being disposed between the front group lens and the rear group lens;
an image sensor that has an imaging area covered with a sensor cover; and
a bonding resin portion that fixes the lens unit to the sensor cover, each optical axis of the front group lens and the rear group lens coinciding with a center of the imaging area,
wherein an end surface of an image side surface of the rear group lens and an outer circumferential surface of the rear group lens is formed by a rough surface portion.

2. The endoscope according to claim 1,
wherein average surface roughness of the rough surface portion falls within a range from 0.1 μm to 10 μm.

3. The endoscope according to claim 1,
wherein the rough surface portion formed in the end surface surrounds an image light emitting effective surface of an image side final surface of the rear group lens.

4. The endoscope according to claim 1, further comprising;
a molded resin portion that covers the bonding resin portion and sensor cover.

5. The endoscope according to claim 1,
wherein the bonding resin portion fixes the rear group lens and an end surface portion of the lens unit to the sensor cover respectively.

6. The endoscope according to claim 5, further comprising;
a molded resin portion that covers the bonding resin portion and sensor cover.

7. An endoscope comprising;
a lens unit that accommodates a front group lens and a rear group lens having an circular exterior shape in a direction perpendicular to an optical axis of each of the front group lens and the rear group lens, an aperture stop being disposed between the front group lens and the rear group lens;
an image sensor that has a square exterior shape in the direction perpendicular to the optical axis, and has one side whose length is the same as a diameter of one of the front group lens and the rear group lens;
a sensor cover that covers an imaging area of the image sensor, has a square exterior shape in the direction perpendicular to the optical axis, and has one side whose length is the same as the length of the one side of the image sensor; and
a bonding resin portion that fixes the lens unit to the sensor cover, each optical axis of the front group lens and the rear group lens coinciding with a center of the imaging area,
wherein an end surface of an image side surface of the rear group lens and an outer circumferential surface of the rear group lens is formed by a rough surface portion.

8. The endoscope according to claim 7,
wherein a diagonal length dimension of the image sensor is 1.4 mm.

* * * * *